United States Patent
Dyvorne et al.

(10) Patent No.: US 11,986,282 B2
(45) Date of Patent: May 21, 2024

(54) SYSTEM AND METHODS FOR DETECTING ELECTROMAGNETIC INTERFERENCE IN PATIENTS DURING MAGNETIC RESONANCE IMAGING

(71) Applicant: Hyperfine Operations, Inc., Guilford, CT (US)

(72) Inventors: Hadrien A. Dyvorne, New York, NY (US); Laura Sacolick, Guilford, CT (US); Carole Lazarus, Paris (FR); Eddy B. Boskamp, Shelton, CT (US); Jeremy Christopher Jordan, Cromwell, CT (US)

(73) Assignee: Hyperfine Operations, Inc., Guilford, CT (US)

( * ) Notice: Subject to any disclaimer, the term of this patent is extended or adjusted under 35 U.S.C. 154(b) by 145 days.

(21) Appl. No.: 17/065,356

(22) Filed: Oct. 7, 2020

(65) Prior Publication Data

US 2021/0103017 A1 Apr. 8, 2021

Related U.S. Application Data

(60) Provisional application No. 62/925,744, filed on Oct. 24, 2019, provisional application No. 62/912,393, filed on Oct. 8, 2019.

(51) Int. Cl.
*A61B 5/055* (2006.01)
*A61B 5/00* (2006.01)
(Continued)

(52) U.S. Cl.
CPC .............. *A61B 5/055* (2013.01); *A61B 5/702* (2013.01); *G01R 33/288* (2013.01);
(Continued)

(58) Field of Classification Search
CPC ..... A61B 5/055; G01R 33/288; G01R 33/422
See application file for complete search history.

(56) References Cited

U.S. PATENT DOCUMENTS

| 5,184,074 A | 2/1993 | Kaufman et al. |
| 5,986,531 A | 11/1999 | Carrozzi |

(Continued)

FOREIGN PATENT DOCUMENTS

| DE | 69931325 T2 | 4/2007 |
| EP | 0995397 A2 | 4/2000 |

(Continued)

OTHER PUBLICATIONS

International Search Report and Written Opinion for International Application No. PCT/US2019/060871 dated Jul. 1, 2020.

(Continued)

*Primary Examiner* — Dixomara Vargas
(74) *Attorney, Agent, or Firm* — Foley & Lardner LLP

(57) ABSTRACT

A magnetic resonance (MR) imaging system, comprising a magnetics system having a plurality of magnetics components configured to produce magnetic fields for performing magnetic resonance imaging, and a sensor configured to detect electromagnetic interference conducted by a patient into an imaging region of the MR imaging system. The sensor may comprise at least one electrical conductor configured for electrically coupling to the patient. The MR imaging system may further comprise a noise reduction system configured to receive the electromagnetic interference from the sensor and to suppress electromagnetic interference in detected MR signals received by the MR imaging system based on the electromagnetic interference detected by the sensor.

20 Claims, 29 Drawing Sheets

(51) Int. Cl.
- *G01R 33/28* (2006.01)
- *G01R 33/422* (2006.01)
- *G01R 33/565* (2006.01)
- *G01R 33/58* (2006.01)
- G01R 29/08 (2006.01)
- G01R 33/34 (2006.01)
- G01R 33/36 (2006.01)
- G01R 33/381 (2006.01)
- G01R 33/385 (2006.01)
- G01R 33/44 (2006.01)

(52) U.S. Cl.
CPC ..... *G01R 33/422* (2013.01); *G01R 33/56518* (2013.01); *G01R 33/583* (2013.01); *A61B 5/0042* (2013.01); *G01R 29/0814* (2013.01); *G01R 33/34007* (2013.01); *G01R 33/34084* (2013.01); *G01R 33/36* (2013.01); *G01R 33/381* (2013.01); *G01R 33/3854* (2013.01); *G01R 33/445* (2013.01)

(56) References Cited

U.S. PATENT DOCUMENTS

| | | | |
|---|---|---|---|
| 6,346,814 B1 | 2/2002 | Carozzi et al. | |
| 6,377,830 B1 | 4/2002 | Carozzi et al. | |
| 6,437,567 B1 * | 8/2002 | Schenck | G01R 33/3415 324/318 |
| 6,801,038 B2 | 10/2004 | Carozzi et al. | |
| 7,529,575 B2 | 5/2009 | Rezzonico et al. | |
| 8,970,217 B1 * | 3/2015 | Kadin | G01R 33/546 324/318 |
| 9,541,616 B2 | 1/2017 | Rothberg et al. | |
| 9,547,057 B2 | 1/2017 | Rearick et al. | |
| 9,625,543 B2 | 4/2017 | Rearick et al. | |
| 9,625,544 B2 | 4/2017 | Poole et al. | |
| 9,638,773 B2 | 5/2017 | Poole et al. | |
| 9,645,210 B2 | 5/2017 | McNulty et al. | |
| 9,797,971 B2 | 10/2017 | Rearick et al. | |
| 9,817,093 B2 | 11/2017 | Rothberg et al. | |
| 10,139,464 B2 | 11/2018 | Rearick et al. | |
| 10,145,913 B2 | 12/2018 | Hugon et al. | |
| 10,145,922 B2 | 12/2018 | Rothberg et al. | |
| 10,222,433 B2 | 3/2019 | Leussler et al. | |
| 10,222,434 B2 | 3/2019 | Poole et al. | |
| 10,222,435 B2 | 3/2019 | Mileski et al. | |
| 10,241,177 B2 | 3/2019 | Poole et al. | |
| 10,274,561 B2 | 4/2019 | Poole et al. | |
| 10,281,540 B2 | 5/2019 | Mileski et al. | |
| 10,281,541 B2 | 5/2019 | Poole et al. | |
| 10,295,628 B2 | 5/2019 | Mileski et al. | |
| 10,310,037 B2 | 6/2019 | McNulty et al. | |
| 10,324,147 B2 | 6/2019 | McNulty et al. | |
| 10,330,755 B2 | 6/2019 | Poole et al. | |
| 10,353,030 B2 | 7/2019 | Poole et al. | |
| 10,371,773 B2 | 8/2019 | Poole et al. | |
| 10,379,186 B2 | 8/2019 | Rothberg et al. | |
| 10,398,345 B2 * | 9/2019 | Strommer | A61B 5/06 |
| 10,416,264 B2 | 9/2019 | Sofka et al. | |
| 10,444,310 B2 | 10/2019 | Poole et al. | |
| 10,466,327 B2 | 11/2019 | Rothberg et al. | |
| 10,488,482 B2 | 11/2019 | Rearick et al. | |
| 10,495,712 B2 | 12/2019 | Rothberg et al. | |
| 10,502,802 B1 * | 12/2019 | Kadin | G01R 33/543 |
| 10,520,566 B2 | 12/2019 | Poole et al. | |
| 10,527,692 B2 | 1/2020 | McNulty et al. | |
| 10,534,058 B2 | 1/2020 | Sofka et al. | |
| 10,539,637 B2 | 1/2020 | Poole et al. | |
| 10,545,207 B2 | 1/2020 | Poole et al. | |
| 10,551,452 B2 | 2/2020 | Rearick et al. | |
| 10,564,239 B2 | 2/2020 | Poole et al. | |
| 10,591,561 B2 | 3/2020 | Sacolick et al. | |
| 10,709,387 B2 | 7/2020 | Poole et al. | |
| D912,822 S | 3/2021 | Hugon | |
| 11,061,089 B2 * | 7/2021 | Boskamp | G01R 33/4215 |
| 2001/0010464 A1 * | 8/2001 | Takamori | G01R 33/3854 324/318 |
| 2001/0037063 A1 * | 11/2001 | Albert | G01R 33/445 600/420 |
| 2002/0057088 A1 | 5/2002 | Carozzi et al. | |
| 2004/0243015 A1 * | 12/2004 | Smith | A61B 5/344 600/511 |
| 2005/0049491 A1 | 3/2005 | Rezzonico et al. | |
| 2008/0060843 A1 | 3/2008 | Ginanneschi | |
| 2011/0270077 A1 * | 11/2011 | Kang | G01T 1/1603 600/411 |
| 2012/0065536 A1 * | 3/2012 | Causevic | A61B 5/30 600/544 |
| 2012/0232609 A1 * | 9/2012 | Tyers | A61N 1/3752 607/37 |
| 2014/0191757 A1 * | 7/2014 | Randell | G01R 33/34007 324/322 |
| 2014/0235989 A1 * | 8/2014 | Wodlinger | A61B 5/283 600/374 |
| 2014/0300358 A1 * | 10/2014 | Rapoport | G01R 33/565 324/322 |
| 2016/0029969 A1 * | 2/2016 | Assif | A61B 5/055 600/411 |
| 2016/0033601 A1 * | 2/2016 | Assif | G01R 33/4814 600/411 |
| 2016/0069968 A1 | 3/2016 | Rothberg et al. | |
| 2016/0069970 A1 | 3/2016 | Rearick et al. | |
| 2016/0069971 A1 | 3/2016 | Mcnulty et al. | |
| 2016/0069972 A1 | 3/2016 | Poole et al. | |
| 2016/0069975 A1 | 3/2016 | Rothberg et al. | |
| 2016/0128592 A1 | 5/2016 | Rosen et al. | |
| 2016/0131727 A1 | 5/2016 | Sacolick et al. | |
| 2016/0139224 A1 * | 5/2016 | Assif | A61B 5/055 600/411 |
| 2016/0169992 A1 | 6/2016 | Rothberg et al. | |
| 2016/0169993 A1 | 6/2016 | Rearick et al. | |
| 2016/0209486 A1 | 7/2016 | Nisznansky et al. | |
| 2016/0223631 A1 | 8/2016 | Poole et al. | |
| 2016/0231399 A1 | 8/2016 | Rothberg et al. | |
| 2016/0231402 A1 | 8/2016 | Rothberg et al. | |
| 2016/0231403 A1 | 8/2016 | Rothberg et al. | |
| 2016/0231404 A1 | 8/2016 | Rothberg et al. | |
| 2016/0299203 A1 | 10/2016 | Mileski et al. | |
| 2016/0320463 A1 | 11/2016 | O'Neill et al. | |
| 2016/0334479 A1 | 11/2016 | Poole et al. | |
| 2017/0102443 A1 | 4/2017 | Rearick et al. | |
| 2017/0108569 A1 * | 4/2017 | Harvey | G01R 33/36 |
| 2017/0227616 A1 | 8/2017 | Poole et al. | |
| 2017/0276747 A1 | 9/2017 | Hugon et al. | |
| 2017/0276749 A1 | 9/2017 | Hugon et al. | |
| 2017/0307701 A1 | 10/2017 | Leussler et al. | |
| 2017/0307703 A1 * | 10/2017 | Wiesinger | G01R 33/3854 |
| 2018/0024208 A1 | 1/2018 | Rothberg et al. | |
| 2018/0028092 A1 | 2/2018 | Okamoto et al. | |
| 2018/0038931 A1 | 2/2018 | Rearick et al. | |
| 2018/0088193 A1 | 3/2018 | Rearick et al. | |
| 2018/0092557 A1 * | 4/2018 | Bickford | A61B 5/375 |
| 2018/0143274 A1 | 5/2018 | Poole et al. | |
| 2018/0143275 A1 | 5/2018 | Sofka et al. | |
| 2018/0143280 A1 | 5/2018 | Dyvorne et al. | |
| 2018/0143281 A1 | 5/2018 | Sofka et al. | |
| 2018/0144467 A1 | 5/2018 | Sofka et al. | |
| 2018/0156881 A1 | 6/2018 | Poole et al. | |
| 2018/0164390 A1 | 6/2018 | Poole et al. | |
| 2018/0168527 A1 | 6/2018 | Poole et al. | |
| 2018/0210047 A1 | 7/2018 | Poole et al. | |
| 2018/0224512 A1 | 8/2018 | Poole et al. | |
| 2018/0238978 A1 | 8/2018 | McNulty et al. | |
| 2018/0238980 A1 | 8/2018 | Poole et al. | |
| 2018/0238981 A1 | 8/2018 | Poole et al. | |
| 2018/0284175 A1 * | 10/2018 | Bickford | G01R 29/0878 |
| 2019/0004130 A1 | 1/2019 | Poole et al. | |
| 2019/0011510 A1 | 1/2019 | Hugon et al. | |
| 2019/0011513 A1 | 1/2019 | Poole et al. | |
| 2019/0011514 A1 | 1/2019 | Poole et al. | |
| 2019/0011521 A1 | 1/2019 | Sofka et al. | |
| 2019/0018094 A1 | 1/2019 | Mileski et al. | |

(56) References Cited

U.S. PATENT DOCUMENTS

| | | |
|---|---|---|
| 2019/0018095 A1 | 1/2019 | Mileski et al. |
| 2019/0018096 A1 | 1/2019 | Poole et al. |
| 2019/0025389 A1 | 1/2019 | McNulty et al. |
| 2019/0033402 A1 | 1/2019 | McNulty et al. |
| 2019/0033414 A1 | 1/2019 | Sofka et al. |
| 2019/0033415 A1 | 1/2019 | Sofka et al. |
| 2019/0033416 A1 | 1/2019 | Rothberg et al. |
| 2019/0038233 A1 | 2/2019 | Poole et al. |
| 2019/0041476 A1* | 2/2019 | Otake .................. G01R 33/343 |
| 2019/0086497 A1 | 3/2019 | Rearick et al. |
| 2019/0101607 A1 | 4/2019 | Rothberg et al. |
| 2019/0162806 A1 | 5/2019 | Poole et al. |
| 2019/0178962 A1 | 6/2019 | Poole et al. |
| 2019/0178963 A1 | 6/2019 | Poole et al. |
| 2019/0227133 A1 | 7/2019 | Leussler et al. |
| 2019/0227136 A1 | 7/2019 | Mileski et al. |
| 2019/0227137 A1 | 7/2019 | Mileski et al. |
| 2019/0250227 A1 | 8/2019 | McNulty et al. |
| 2019/0250228 A1 | 8/2019 | McNulty et al. |
| 2019/0257903 A1 | 8/2019 | Poole et al. |
| 2019/0324098 A1 | 10/2019 | McNulty et al. |
| 2019/0353720 A1 | 11/2019 | Dyvorne et al. |
| 2019/0353723 A1 | 11/2019 | Dyvorne et al. |
| 2019/0353726 A1 | 11/2019 | Poole et al. |
| 2019/0353727 A1 | 11/2019 | Dyvorne et al. |
| 2020/0011952 A1 | 1/2020 | Rothberg et al. |
| 2020/0018806 A1 | 1/2020 | Rothberg et al. |
| 2020/0022611 A1 | 1/2020 | Nelson et al. |
| 2020/0022612 A1 | 1/2020 | McNulty et al. |
| 2020/0022613 A1 | 1/2020 | Nelson et al. |
| 2020/0025846 A1 | 1/2020 | Nelson et al. |
| 2020/0025851 A1 | 1/2020 | Rearick et al. |
| 2020/0033431 A1 | 1/2020 | Schlemper et al. |
| 2020/0034998 A1 | 1/2020 | Schlemper et al. |
| 2020/0041588 A1 | 2/2020 | O'Halloran et al. |
| 2020/0045112 A1 | 2/2020 | Sacolick et al. |
| 2020/0058106 A1 | 2/2020 | Lazarus et al. |
| 2020/0200844 A1 | 6/2020 | Boskamp et al. |
| 2020/0209334 A1 | 7/2020 | O'Halloran et al. |
| 2020/0249292 A1* | 8/2020 | Biber .................. G01R 33/3692 |
| 2020/0289019 A1 | 9/2020 | Schlemper et al. |
| 2020/0289022 A1 | 9/2020 | Coumans et al. |
| 2020/0294229 A1 | 9/2020 | Schlemper et al. |
| 2020/0294282 A1 | 9/2020 | Schlemper et al. |
| 2020/0294287 A1 | 9/2020 | Schlemper et al. |
| 2020/0337587 A1 | 10/2020 | Sacolick et al. |
| 2020/0355765 A1 | 11/2020 | Chen et al. |
| 2021/0048498 A1 | 2/2021 | Dyvorne et al. |
| 2021/0100474 A1* | 4/2021 | Dyvorne .............. G01R 33/422 |
| 2021/0103017 A1 | 4/2021 | Dyvorne et al. |
| 2021/0311143 A1 | 10/2021 | Boskamp et al. |

FOREIGN PATENT DOCUMENTS

| | | |
|---|---|---|
| EP | 0995397 A3 | 5/2000 |
| EP | 1004269 A1 | 5/2000 |
| EP | 0995397 B1 | 5/2006 |
| EP | 1004269 B1 | 3/2011 |
| ES | 2260874 T3 | 11/2006 |
| ES | 2359543 T3 | 5/2011 |

OTHER PUBLICATIONS

Invitation to Pay Additional Fees for International Application No. PCT/US2019/060871, dated Mar. 3, 2020.

Boskamp et al., Water-cooling in the space between RF body coil and RF shield. Proceedings of the International Society of Magnetic Resonance in Medicine. 2005;13:937.

Handa et al., Development of a local electromagnetic shielding for an extremity magnetic resonance imaging system. Review of scientific instruments. Nov. 24, 2008;79(11):113706.

Invitation to Pay Additional Fees for International Application No. PCT/US2020/054564 dated Mar. 3, 2021.

International Search Report and Written Opinion for International Application No. PCT/US2020/054564 dated Apr. 28, 2021.

U.S. Appl. No. 16/680,992, filed Nov. 12, 2019, Boskamp et al..

U.S. Appl. No. 17/065,344, filed Oct. 7, 2020, Dyvorne et al.

PCT/US2019/060871, Mar. 3, 2020, Invitation to Pay Additional Fees.

PCT/US2019/060871, Jul. 1, 2020, International Search Report and Written Opinion.

Invitation to Pay Additional Fees for Application No. PCT/US2019/060871, mailed Mar. 3, 2020.

Invitation to Pay Additional Fees for International Application No. PCT/US2020/054564 mailed Mar. 3, 2021.

* cited by examiner

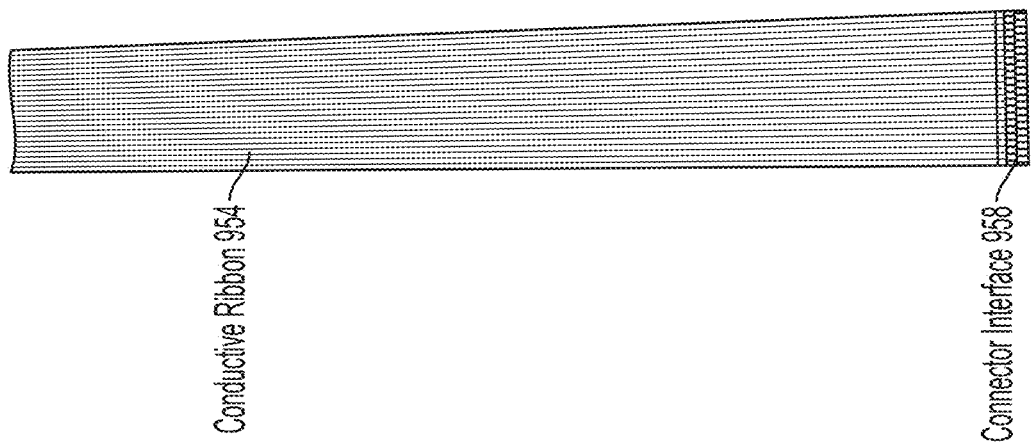

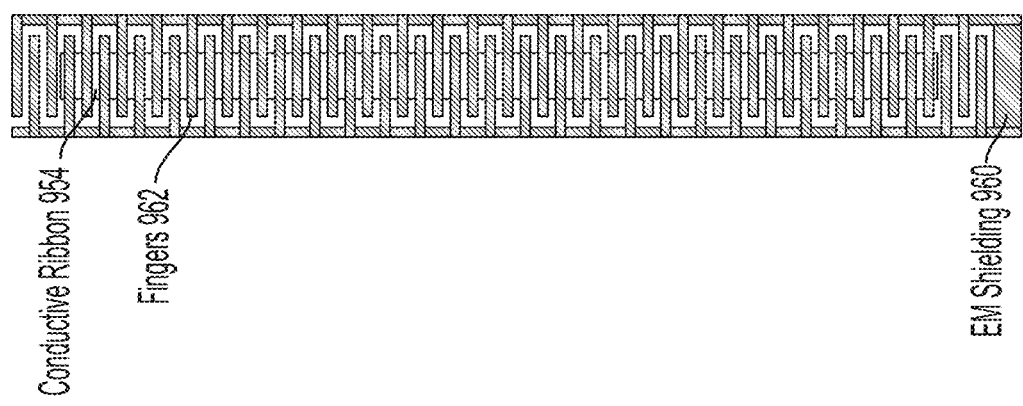

SYSTEM AND METHODS FOR DETECTING ELECTROMAGNETIC INTERFERENCE IN PATIENTS DURING MAGNETIC RESONANCE IMAGING

CROSS REFERENCE TO RELATED APPLICATIONS

This application claims the benefit of priority under 35 U.S.C. § 119(e) to U.S. Provisional Application Ser. No. 62/925,744, filed Oct. 24, 2019, and entitled, "SYSTEM AND METHODS FOR DETECTING ELECTROMAGNETIC INTERFERENCE IN PATIENTS DURING MAGNETIC RESONANCE IMAGING," and to U.S. Provisional Application Ser. No. 62/912,393, filed Oct. 8, 2019, and entitled, "SYSTEM AND METHODS FOR DETECTING ELECTROMAGNETIC NOISE IN PATIENTS DURING MAGNETIC RESONANCE IMAGING," each of which is incorporated by reference herein in its entirety.

BACKGROUND

Magnetic resonance imaging (MRI) provides an important imaging modality for numerous applications and is widely utilized in clinical and research settings to produce images of the inside of the human body. MRI is based on detecting magnetic resonance (MR) signals, which are electromagnetic waves emitted by atoms in response to state changes resulting from applied electromagnetic fields. For example, nuclear magnetic resonance (NMR) techniques involve detecting MR signals emitted from the nuclei of excited atoms upon the re-alignment or relaxation of the nuclear spin of atoms in an object being imaged (e.g., atoms in the tissue of the human body). Detected MR signals may be processed to produce images, which in the context of medical applications allows for the investigation of internal structures and/or biological processes within the body for diagnostic, therapeutic and/or research purposes.

MRI provides an attractive imaging modality for biological imaging due to the ability to produce non-invasive images having relatively high resolution and contrast without the safety concerns of other modalities (e.g., without needing to expose the subject to ionizing radiation, e.g., x-rays, or introducing radioactive material to the body). Additionally, MRI is particularly well suited to provide soft tissue contrast, which can be exploited to image subject matter that other imaging modalities are incapable of satisfactorily imaging. Moreover, MR techniques are capable of capturing information about structures and/or biological processes that other modalities are incapable of acquiring. However, there are a number of drawbacks to MRI that, for a given imaging application, may involve the relatively high cost of the equipment, limited availability and/or difficulty in gaining access to clinical MRI scanners and/or the length of the image acquisition process.

The trend in clinical MRI has been to increase the field strength of MRI scanners to improve one or more of scan time, image resolution, and image contrast, which, in turn, continues to drive up costs. The vast majority of installed MRI scanners operate at 1.5 or 3 tesla (T), which refers to the field strength of the main magnetic field $B_0$. A rough cost estimate for a clinical MRI scanner is approximately one million dollars per tesla, which does not factor in the substantial operation, service, and maintenance costs involved in operating such MRI scanners.

Additionally, conventional high-field MRI systems typically require large superconducting magnets and associated electronics to generate a strong uniform static magnetic field ($B_0$) in which an object (e.g., a patient) is imaged. The size of such systems is considerable with a typical MRI installment including multiple rooms for the magnet, electronics, thermal management system, and control console areas. The size and expense of MRI systems generally limits their usage to facilities, such as hospitals and academic research centers, which have sufficient space and resources to purchase and maintain them. The high cost and substantial space requirements of high-field MRI systems results in limited availability of MRI scanners.

SUMMARY

Some aspects of the present disclosure relate to a magnetic resonance (MR) imaging system, comprising a magnetics system having a plurality of magnetics components configured to produce magnetic fields for performing magnetic resonance imaging, a sensor configured to detect electromagnetic interference introduced by a patient into an imaging region of the MR imaging system, and circuitry configured to receive detected electromagnetic interference from the sensor and to suppress and/or compensate for the detected electromagnetic interference.

In some embodiments, the sensor comprises at least one electrical conductor configured for electrically coupling to the patient. In some embodiments, the at least one electrical conductor is configured for capacitively coupling to the patient.

In some embodiments, the sensor further comprises one or more printed circuit boards (PCBs) having the at least one electrical conductor thereon. In some embodiments, the one or more PCBs include a flexible PCB. In some embodiments, the one or more PCBs are coupled to a noise reduction system of the MR imaging system via at least one electrical connector.

In some embodiments, the plurality of magnetics components include a radio frequency (RF) component comprising at least one radio frequency coil. In some embodiments, the radio frequency component comprises a housing formed to accommodate a portion of the patient's anatomy, wherein the housing provides support for the at least one radio frequency coil and the at least one electrical conductor. In some embodiments, the sensor further comprises electromagnetic shielding positioned between the at least one radio frequency coil and the at least one electrical conductor. In some embodiments, the sensor comprises one or more printed circuit boards (PCBs) having the at least one electrical conductor and the electromagnetic shielding thereon.

In some embodiments, the housing is configured to accommodate a head of the patient therein, and wherein the at least one electrical conductor is configured for capacitively coupling to the head of the patient when the head is positioned within the housing. In some embodiments, the housing is shaped to fit a leg and/or foot of the patient therein, and the at least one electrical conductor is configured for capacitively coupling to the leg and/or foot of the patient when the leg and/or foot is positioned within the housing. In some embodiments, the housing includes a chamber having at least one interior surface, and the at least one electrical conductor is positioned on the at least one interior surface.

In some embodiments, the sensor includes at least a first flexible printed circuit board (PCB) elongated along the at least one interior surface in a first direction having a first electrical conductor of the at least one electrical conductor disposed thereon, and at least a second flexible PCB elongated on the interior surface in a second direction perpendicular to the first direction and having a second electrical conductor of the at least one electrical conductor disposed thereon. In some embodiments, the interior surface includes a cylindrical portion, the at least a first flexible PCB is elongated along an axis at least partially encircled by the cylindrical portion, and the at least a second flexible PCB at least partially encircles the axis.

In some embodiments, the at least a first flexible PCB includes a first plurality of electrically conductive strips elongated in parallel with one another, and the at least a second flexible PCB includes a second plurality of conductive strips elongated in parallel with one another. In some embodiments, the sensor further includes at least a third flexible PCB positioned between the first flexible PCB and the at least one radio frequency coil and/or between the second flexible PCB and the at least one radio frequency coil, and the third flexible PCB includes a third plurality of conductive strips configured to provide electromagnetic shielding between the first and/or second plurality of conductive strips and the at least one radio frequency coil. In some embodiments, the at least a first flexible PCB further includes a third plurality of electrically conductive strips configured to provide electromagnetic shielding between the first plurality of electrically conductive strips and the at least one radio frequency coil, and the at least a second flexible PCB further includes a fourth plurality of electrically conductive strips configured to provide electromagnetic shielding between the second plurality of electrically conductive strips and the at least one radio frequency coil.

In some embodiments, the at least one electrical conductor comprises a conductive pad. In some embodiments, the conductive pad is configured to be worn around a neck of the patient. In some embodiments, the MR imaging system further comprises a surface configured to support a patient during imaging, wherein the conductive pad is positioned on the surface. In some embodiments, the MR imaging system further comprises an electrically insulative layer positioned between the surface and the conductive pad.

In some embodiments, the at least one electrical conductor comprises a conductive patch configured for attaching to the patient. In some embodiments, the conductive patch is configured for adhering to the patient's skin.

In some embodiments, the MR imaging system further comprises a noise reduction system coupled to the sensor and configured to compensate for the electromagnetic interference during imaging of the patient. In some embodiments, the sensor further includes amplification circuitry configured to amplify the electromagnetic interference and provide the electromagnetic interference to the noise reduction system.

In some embodiments, the plurality of magnetics components include a radio frequency (RF) component comprising at least one radio frequency coil, and the sensor further comprises electromagnetic shielding positioned between the at least one electrical conductor and the at least one radio frequency coil, the electromagnetic shielding being electrically coupled to the amplification circuitry.

In some embodiments, the sensor includes a printed circuit board (PCB) having the amplification circuitry thereon, and the PCB is coupled between the at least one electrical conductor and the noise reduction system.

In some embodiments, the plurality of magnetics components include at least one radio frequency (RF) coil configured to, when operated, receive magnetic resonance signals emitted from a field of view of the MR imaging system, and the noise reduction system is configured to reduce an impact of the electromagnetic interference on the magnetic resonance signals.

In some embodiments, the plurality of magnetics components include at least one permanent $B_0$ magnet configured to produce a $B_0$ magnetic field for an imaging region of the MR imaging system, a plurality of gradient coils configured to, when operated, generate magnetic fields to provide spatial encoding of emitted magnetic resonance signals, and at least one radio frequency (RF) coil configured to, when operated, transmit radio frequency signals to a field of view of the MR imaging system and receive magnetic resonance signals emitted from the field of view. In some embodiments, the at least one permanent $B_0$ magnet is configured to produce a $B_0$ magnetic field having a field strength of less than 0.2 T. In some embodiments, the at least one permanent $B_0$ magnet is configured to produce a $B_0$ magnetic field having a field strength of greater than 50 mT and less than 0.1 T.

In some embodiments, the circuitry is configured to obtain samples of the electromagnetic interference from the sensor and subtract a version of the samples from MR signals received via the magnetics system. In some embodiments, the circuitry is configured to apply a transfer function to the samples and subtract transformed versions of the samples from the MR signals. In some embodiments, the circuitry is configured to obtain calibration noise measurements of the electromagnetic interference from the sensor and determine the transfer function using the calibration noise measurements. In some embodiments, the circuitry is configured to estimate an amplitude and phase of the transfer function for each of a plurality of frequency bins of the transfer function using the calibration noise measurements.

Some aspects of the present disclosure relate to a magnetic resonance (MR) imaging system comprising a magnetics system having a plurality of magnetics components configured to produce magnetic fields for performing magnetic resonance imaging and a noise reduction system configured to receive electromagnetic interference electrically coupled from a patient and compensate for the electromagnetic interference during imaging of the patient.

In some embodiments, the noise reduction system is electrically coupled to a sensor configured to electrically couple the electromagnetic interference from the patient to the noise reduction system. In some embodiments, the sensor comprises at least one electrical conductor configured for electrically coupling to the patient. In some embodiments, the at least one electrical conductor is configured for capacitively coupling to the patient.

In some embodiments, the sensor further comprises one or more printed circuit boards (PCBs) having the at least one electrical conductor thereon. In some embodiments, the one or more PCBs include a flexible PCB.

In some embodiments, the one or more PCBs are coupled to a noise reduction system of the MR imaging system via at least one electrical connector.

In some embodiments, the plurality of magnetics components include a radio frequency (RF) component, comprising at least one radio frequency coil and the at least one electrical conductor. In some embodiments, the sensor further comprises electromagnetic shielding positioned between the at least one radio frequency coil and the at least one electrical conductor. In some embodiments, the sensor comprises one or more printed circuit boards (PCBs) having the at least one electrical conductor and the electromagnetic shielding thereon.

In some embodiments, the radio frequency component comprises a housing formed to accommodate a portion of the patient's anatomy, wherein the housing provides support for the at least one radio frequency coil and the at least one electrical conductor. In some embodiments, the housing is configured to accommodate a head of the patient therein, and wherein the at least one electrical conductor is configured for capacitively coupling to the head of the patient when the head is positioned within the housing. In some embodiments, the housing is shaped to fit a leg and/or foot of the patient therein and the at least one electrical conductor is configured for capacitively coupling to the leg and/or foot of the patient when the leg and/or foot is positioned within the housing.

In some embodiments, the housing includes a chamber having at least one interior surface, and the at least one electrical conductor is positioned on the at least one interior surface. In some embodiments, the sensor includes at least a first flexible printed circuit board (PCB) elongated along the at least one interior surface in a first direction having a first electrical conductor of the at least one electrical conductor disposed thereon, and at least a second flexible PCB elongated on the interior surface in a second direction perpendicular to the first direction and having a second electrical conductor of the at least one electrical conductor disposed thereon. In some embodiments, the interior surface includes a cylindrical portion, the at least a first flexible PCB is elongated along an axis at least partially encircled by the cylindrical portion, and the at least a second flexible PCB at least partially encircles the axis.

In some embodiments, the at least a first flexible PCB includes a first plurality of electrically conductive strips elongated in parallel with one another, and the at least a second flexible PCB includes a second plurality of conductive strips elongated in parallel with one another. In some embodiments, the sensor further includes at least a third flexible PCB positioned between the at least a first flexible PCB and the at least one radio frequency coil and/or between the at least a second flexible PCB and the at least one radio frequency coil, and the third flexible PCB includes a third plurality of conductive strips configured to provide electromagnetic shielding between the first and/or second plurality of conductive strips and the at least one radio frequency coil.

In some embodiments, the at least a first flexible PCB further includes a third plurality of electrically conductive strips configured to provide electromagnetic shielding between the first plurality of electrically conductive strips and the at least one radio frequency coil, and the at least a second flexible PCB further includes a fourth plurality of electrically conductive strips configured to provide electromagnetic shielding between the second plurality of electrically conductive strips and the at least one radio frequency coil.

In some embodiments, the at least one electrical conductor comprises a conductive pad. In some embodiments, the conductive pad is configured to be worn around a neck of the patient. In some embodiments, the MR imaging system further comprises a surface configured to support a patient during imaging, wherein the conductive pad is positioned on the surface. In some embodiments, the MR imaging system further comprises an electrically insulative layer positioned between the surface and the conductive pad.

In some embodiments, the at least one electrical conductor comprises a conductive patch configured for attaching to the patient. In some embodiments, the conductive patch is configured for adhering to the patient.

In some embodiments, the MR imaging system further comprises amplification circuitry configured to amplify the electromagnetic interference and provide the electromagnetic interference to the noise reduction system. In some embodiments, the plurality of magnetics components include a radio frequency (RF) component comprising at least one radio frequency coil, and the MR imaging system further comprises electromagnetic shielding positioned between the at least one electrical conductor and the at least one radio frequency coil, the electromagnetic shielding being electrically coupled to the amplification circuitry. In some embodiments, the sensor includes a printed circuit board (PCB) having the amplification circuitry thereon, and the PCB is coupled between the at least one electrical conductor and the noise reduction system.

In some embodiments, the plurality of magnetics components include at least one radio frequency (RF) coil configured to, when operated, receive magnetic resonance signals emitted from a field of view of the MR imaging system, and the noise reduction system is configured to reduce an impact of the electromagnetic interference on the magnetic resonance signals.

In some embodiments, the plurality of magnetics components include at least one permanent $B_0$ magnet configured to produce a $B_0$ magnetic field for an imaging region of the MR imaging system, a plurality of gradient coils configured to, when operated, generate magnetic fields to provide spatial encoding of emitted magnetic resonance signals, and at least one radio frequency (RF) coil configured to, when operated, transmit radio frequency signals to a field of view of the MR imaging system and receive magnetic resonance signals emitted from the field of view. In some embodiments, the at least one permanent $B_0$ magnet is configured to produce a $B_0$ magnetic field having a field strength of less than 0.2 T. In some embodiments, the at least one permanent $B_0$ magnet is configured to produce a $B_0$ magnetic field having a field strength of greater than 50 mT and less than 0.1 T.

In some embodiments, the noise reduction system is configured to obtain samples of the electromagnetic interference and subtract a version of the samples from MR signals received via the magnetics system. In some embodiments, the noise reduction system is configured to apply a transfer function to the samples and subtract transformed versions of the samples from the MR signals. In some embodiments, the noise reduction system is configured to obtain calibration noise measurements of the electromagnetic interference and determine the transfer function using the calibration noise measurements. In some embodiments, the noise reduction system is configured to estimate an amplitude and phase of the transfer function for each of a plurality of frequency bins of the transfer function using the calibration noise measurements.

Some aspects of the present disclosure relate to an electric field detector (EFD) for a magnetic resonance (MR) imaging system, the EFD comprising at least one electrical conductor configured for electrically coupling electromagnetic interference from a patient to a noise reduction system of the MR imaging system.

In some embodiments, the at least one electrical conductor is configured for capacitively coupling to the patient. In some embodiments, the EFD further comprises one or more printed circuit boards (PCBs) having the at least one electrical conductor thereon. In some embodiments, the one or more PCBs include a flexible PCB. In some embodiments, the one or more PCBs are configured for coupling to a noise reduction system of the MR imaging system via at least one electrical connector.

In some embodiments, the at least one electrical conductor is configured for attaching to a magnetic component of the MRI imaging system. In some embodiments, the EFD further comprises electromagnetic shielding configured to be positioned between the magnetic component and the at least one electrical conductor. In some embodiments, the magnetic component comprises at least one radio frequency coil, and the electromagnetic shielding is configured to be positioned between the at least one radio frequency coil and the at least one electrical conductor. In some embodiments, the EFD comprises one or more printed circuit boards (PCBs) having the at least one electrical conductor and the electromagnetic shielding thereon.

In some embodiments, the magnetic component is a radio frequency component comprising a housing formed to accommodate a portion of the patient's anatomy, and the at least one electrical conductor is configured for attaching to the housing. In some embodiments, when attached to the housing, the at least one electrical conductor is configured for capacitively coupling to a head of the patient when the head is positioned within the housing. In some embodiments, when attached to the housing, the at least one electrical conductor is configured for capacitively coupling to a leg and/or foot of the patient when the leg and/or foot is positioned within the housing. In some embodiments, the at least one electrical conductor is configured for attaching to at least one interior surface of the housing.

In some embodiments, the EFD further comprises at least a first flexible printed circuit board (PCB) having a first electrical conductor of the at least one electrical conductor disposed thereon, and at least a second flexible PCB having a second electrical conductor of the at least one electrical conductor disposed thereon, and the at least a first flexible PCB and the at least a second flexible PCB are attached to one another such that the at least a first flexible PCB is elongated in a direction perpendicular to a direction in which the at least a second flexible PCB is elongated.

In some embodiments, the at least a first and the at least a second flexible PCBs each include a plurality of electrically conductive strips, the plurality of electrically conductive strips of the at least a first flexible PCB elongated parallel to one another and the plurality of electrically conductive strips of the at least a second flexible PCB elongated in parallel to one another. In some embodiments, the EFD further comprises a third flexible PCB configured to be positioned between the at least a first flexible PCB and the radio frequency component and/or between the at least a second flexible PCB and the at least one interior surface of the housing, and the third flexible PCB includes a third plurality of conductive strips configured to provide electromagnetic shielding between the first and/or second plurality of conductive strips and the radio frequency component.

In some embodiments, the at least a first flexible PCB further includes a third plurality of electrically conductive strips configured to provide electromagnetic shielding between the first plurality of electrically conductive strips and the radio frequency component, and the at least a second flexible PCB further includes a fourth plurality of electrically conductive strips configured to provide electromagnetic shielding between the second plurality of electrically conductive strips and the radio frequency component.

Some aspects of the present disclosure relate to a method of operating a magnetic resonance imaging (MRI) system, the MRI system comprising a magnetics system having a plurality of magnetics components configured to produce magnetic fields for performing MRI and a sensor, the method comprising detecting electromagnetic interference conducted by a patient using the sensor and suppressing and/or compensating for the detected electromagnetic interference in magnetic resonance signals.

In some embodiments, detecting electromagnetic interference conducted by the patient comprises electrically coupling the sensor to the patient. In some embodiments, electrically coupling the sensor to the patient comprises electrically coupling the patient to one or more electrical conductors of the sensor.

In some embodiments, electrically coupling the patient to the one or more electrical conductors comprises electrically coupling the patient to an electrically conductive pad. In some embodiments, electrically coupling the patient to the electrically conductive pad comprises positioning the patient to be in physical contact with the electrically conductive pad. In some embodiments, positioning the patient to be in physical contact with the electrically conductive pad comprises positioning the patient to be in physical contact with an electrically conductive portion on an outer surface of the electrically conductive pad. In some embodiments, electrically coupling the patient to the electrically conductive pad comprises positioning the patient within a capacitive coupling range of the electrically conductive pad. In some embodiments, positioning the patient within a capacitive coupling range of the electrically conductive pad comprises positioning the patient to be within a capacitive coupling range of an electrically conductive portion of the electrically conductive pad, the electrically conductive portion separated from the patient by one or more insulative layers.

In some embodiments, electrically coupling the patient to the one or more electrical conductors comprises electrically coupling the patient to an electrically conductive patch. In some embodiments, electrically coupling the patient to an electrically conductive patch comprises attaching the electrically conductive patch to the patient. In some embodiments, attaching the electrically conductive patch to the patient comprises positioning an electrically conductive portion of the electrically conductive patch in physical contact with the patient. In some embodiments, attaching the electrically conductive patch to the patient comprises positioning an electrically conductive portion of the electrically conductive patch in capacitive coupling range of the patient, electrically conducive portion separated from the patient by one or more insulative layers. In some embodiments, attaching the electrically conductive patch to the patient comprises adhering the electrically conductive patch to the patient's skin.

In some embodiments, imaging the patient using the MRI system comprises generating a magnetic resonance image of the patient's anatomy at least in part by generating magnetic fields in accordance with a pulse sequence and detecting, using at least one radio frequency coil, magnetic resonance signals emitted from the portion of the patient's anatomy.

In some embodiments, electrically coupling the sensor to the patient comprises electrically coupling an electric field detector (EFD) to the patient, the EFD comprising the one or more electrical conductors. In some embodiments, electrically coupling the EFD to the patient comprises positioning the patient within capacitive coupling range of the one or more electrical conductors of the EFD. In some embodiments, positioning the patient within capacitive coupling range of the one or more electrical conductors of the EFD comprises placing at least a portion of the patient's anatomy in an accommodation portion of a magnetic component of the plurality of magnetics components. In some embodiments, the magnetic component comprises a radio frequency (RF) coil having a housing, the housing supporting the one or more electrical conductors of the EFD. In some embodiments, the EFD comprises electromagnetic shielding positioned between the one or more electrical conductors and the RF coil.

In some embodiments, the suppressing and/or compensating comprises obtaining samples of the electromagnetic interference from the sensor and subtracting a version of the samples from MR signals received via the magnetics system. In some embodiments, the suppressing and/or compensating further comprises applying a transfer function to the samples and subtracting transformed versions of the samples from the MR signals. In some embodiments, the method further comprises obtaining calibration noise measurements of the electromagnetic interference from the sensor and determining the transfer function using the calibration noise measurements. In some embodiments, the method further comprises estimating an amplitude and phase of the transfer function for each of a plurality of frequency bins of the transfer function using the calibration noise measurements.

Some aspects of the present disclosure relate to a radio frequency component configured for use in magnetic resonance imaging, the radio frequency component comprising a housing configured to accommodate anatomy of a patient for imaging, the housing providing support for and/or housing at least one transmit coil configured to produce radio frequency magnetic fields that, when the patient is present, cause a magnetic resonance response in the anatomy of the patient, and at least one receive coil for detecting magnetic resonance imaging signals, and a sensor positioned to couple to the anatomy to detect electromagnetic radiation introduced by the patient, and circuitry configured to receive detected electromagnetic radiation and to suppress and/or compensate for the detected electromagnetic radiation in magnetic resonance imaging signals detected by the at least one receive coil.

In some embodiments, the sensor comprises at least one electrical conductor configured for electrically coupling to the patient. In some embodiments, the at least one electrical conductor is configured for capacitively coupling to the patient.

In some embodiments, the sensor further comprises one or more printed circuit boards (PCBs) having the at least one electrical conductor thereon. In some embodiments, the one or more PCBs include a flexible PCB. In some embodiments, the one or more PCBs are configured for coupling to a noise reduction system of a magnetic resonance imaging system via at least one electrical connector. In some embodiments, the housing provides support for the at least one electrical conductor.

In some embodiments, the sensor further comprises electromagnetic shielding positioned between the at least one receive coil and the at least one electrical conductor. In some embodiments, the sensor comprises one or more printed circuit boards (PCBs) having the at least one electrical conductor and the electromagnetic shielding thereon.

In some embodiments, the housing is configured to accommodate a head of the patient therein, and wherein the at least one electrical conductor is configured for capacitively coupling to the head of the patient when the head is positioned within the housing. In some embodiments, the housing is shaped to fit a leg and/or foot of the patient therein, and the at least one electrical conductor is configured for capacitively coupling to the leg and/or foot of the patient when the leg and/or foot is positioned within the housing. In some embodiments, the housing includes a chamber having at least one interior surface, and the at least one electrical conductor is positioned on the at least one interior surface.

In some embodiments, the sensor includes at least a first flexible printed circuit board (PCB) elongated along the at least one interior surface in a first direction having a first electrical conductor of the at least one electrical conductor disposed thereon, and at least a second flexible PCB elongated on the interior surface in a second direction perpendicular to the first direction and having a second electrical conductor of the at least one electrical conductor disposed thereon. In some embodiments, the interior surface includes a cylindrical portion, the at least a first flexible PCB is elongated along an axis at least partially encircled by the cylindrical portion, and the at least a second flexible PCB at least partially encircles the axis.

In some embodiments, the at least a first flexible PCB includes a first plurality of electrically conductive strips elongated in parallel with one another, and the at least a second flexible PCB includes a second plurality of conductive strips elongated in parallel with one another. In some embodiments, the sensor further includes at least a third flexible PCB positioned between the first flexible PCB and the at least one radio frequency coil and/or between the second flexible PCB and the at least one radio frequency coil, and the third flexible PCB includes a third plurality of conductive strips configured to provide electromagnetic shielding between the first and/or second plurality of conductive strips and the at least one radio frequency coil.

In some embodiments, the at least a first flexible PCB further includes a third plurality of electrically conductive strips configured to provide electromagnetic shielding between the first plurality of electrically conductive strips and the at least one radio frequency coil, and the at least a second flexible PCB further includes a fourth plurality of electrically conductive strips configured to provide electromagnetic shielding between the second plurality of electrically conductive strips and the at least one radio frequency coil.

In some embodiments, the at least one electrical conductor comprises a conductive pad. In some embodiments, the conductive pad is configured to be worn around a neck of the patient. In some embodiments, the radio frequency component further comprises a surface configured to support a patient during imaging, wherein the conductive pad is positioned on the surface. In some embodiments, the radio frequency component further comprises an electrically insulative layer positioned between the surface and the conductive pad.

In some embodiments, the at least one electrical conductor comprises a conductive patch configured for attaching to the patient. In some embodiments, the conductive patch is configured for adhering to the patient's skin.

In some embodiments, the sensor is configured for coupling to a noise reduction system, the noise reduction system being configured to compensate for the electromagnetic interference during imaging of the patient. In some embodiments, the sensor further includes amplification circuitry configured to amplify the electromagnetic interference and provide the electromagnetic interference to the noise reduction system. In some embodiments, the sensor further comprises electromagnetic shielding positioned between the at least one electrical conductor and the at least one receive coil, the electromagnetic shielding being electrically coupled to the amplification circuitry. In some embodiments, the sensor includes a printed circuit board (PCB) having the amplification circuitry thereon, and the PCB is configured for coupling the at least one electrical conductor to the noise reduction system.

Some aspects of the present disclosure relate to a method of compensating for electromagnetic interference introduced by a patient into an imaging region of a magnetic resonance (MR) imaging system, the method comprising using at least one electrical conductor of an electric field detector (EFD) to electrically couple the electromagnetic interference from the patient to a noise reduction system of the MR imaging system.

In some embodiments, using the at least one electrical conductor comprises capacitively coupling the at least one electrical conductor to the patient. In some embodiments, capacitively coupling the at least one electrical conductor to the patient comprises positioning the at least one electrical conductor in capacitive coupling range of the patient.

In some embodiments, positioning the at least one electrical conductor in capacitive coupling range of the patient comprises positioning one or more printed circuit boards (PCBs) having the at least one electrical conductor thereon in capacitive coupling range of the patient. In some embodiments, the one or more PCBs include a flexible PCB. In some embodiments, the method further comprises electrically coupling the electromagnetic interference from the one or more PCBs to a noise reduction system of the MR imaging system via at least one electrical connector.

In some embodiments, the at least one electrical conductor is attached to a magnetic component of the MRI imaging system. In some embodiments, the method further comprises blocking at least some electrical coupling between the magnetic component and the at least one electrical conductor using electromagnetic shielding. In some embodiments, blocking the at least some electrical coupling between the magnetic component and the at least one electrical conductor comprises blocking at least some electrical coupling between at least one radio frequency coil and the at least one electrical conductor using the electromagnetic shielding, wherein the electromagnetic shielding is positioned between the at least one radio frequency coil and the at least one electrical conductor. In some embodiments, the at least one electrical conductor and the electromagnetic shielding are positioned on one or more printed circuit boards (PCBs) of the EFD.

In some embodiments, the magnetic component is a radio frequency component, and positioning the at least one electrical conductor in capacitive coupling range of the patient comprises accommodating a portion of the patient's anatomy in a housing of the radio frequency component while the at least one electrical conductor is attached to the housing. In some embodiments, positioning the at least one electrical conductor in capacitive coupling range of the patient comprises positioning a head of the patient within the housing. In some embodiments, positioning the at least one electrical conductor in capacitive coupling range of the patient comprises positioning a leg and/or foot of the patient within the housing. In some embodiments, the at least one electrical conductor is attached to at least one interior surface of the housing.

In some embodiments, at least a first flexible printed circuit board (PCB) of the EFD having a first electrical conductor of the at least one electrical conductor disposed thereon is attached to at least a second flexible PCB of the EFD having a second electrical conductor of the at least one electrical conductor disposed thereon, such that the at least a first flexible PCB is elongated in a direction perpendicular to a direction in which the at least a second flexible PCB is elongated, and capacitively coupling the at least one electrical conductor comprises capacitively coupling electromagnetic interference from the patient to the first and second electrical conductors at first and second orthogonal electrical polarities, respectively. In some embodiments, the at least a first flexible PCB and the at least a second flexible PCB each include a plurality of electrically conductive strips, the plurality of electrically conductive strips of the at least a first flexible PCB elongated parallel to one another and the plurality of electrically conductive strips of the at least a second flexible PCB elongated in parallel to one another.

In some embodiments, the method comprises blocking at least some electrical coupling between the first and/or second plurality of conductive strips and the radio frequency component using a third plurality of conductive strips of a third flexible PCB positioned between the at least a first flexible PCB and the radio frequency component and/or between the at least a second flexible PCB and the radio frequency component.

In some embodiments, the method further comprises blocking at least some electrical coupling between the first plurality of electrically conductive strips and the radio frequency component using a third plurality of electrically conductive strips of the at least a first flexible PCB, and blocking at least some electrical coupling between the second plurality of electrically conductive strips and the radio frequency component using a fourth plurality of electrically conductive strips of the at least a second flexible PCB.

It should be appreciated that all combinations of the foregoing concepts and additional concepts described in greater detail below are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF DRAWINGS

Various aspects and embodiments of the disclosed technology will be described with reference to the following figures. It should be appreciated that the figures are not necessarily drawn to scale.

FIG. 9A is a drawing of a conductor formed from a flexible printed circuit board ribbon, in accordance with some embodiments.

FIG. 9C is a drawing of the conductor of FIG. 9A and electromagnetic shielding for the conductor, in accordance with some embodiments of the technology described herein.

DETAILED DESCRIPTION

Figure 1:
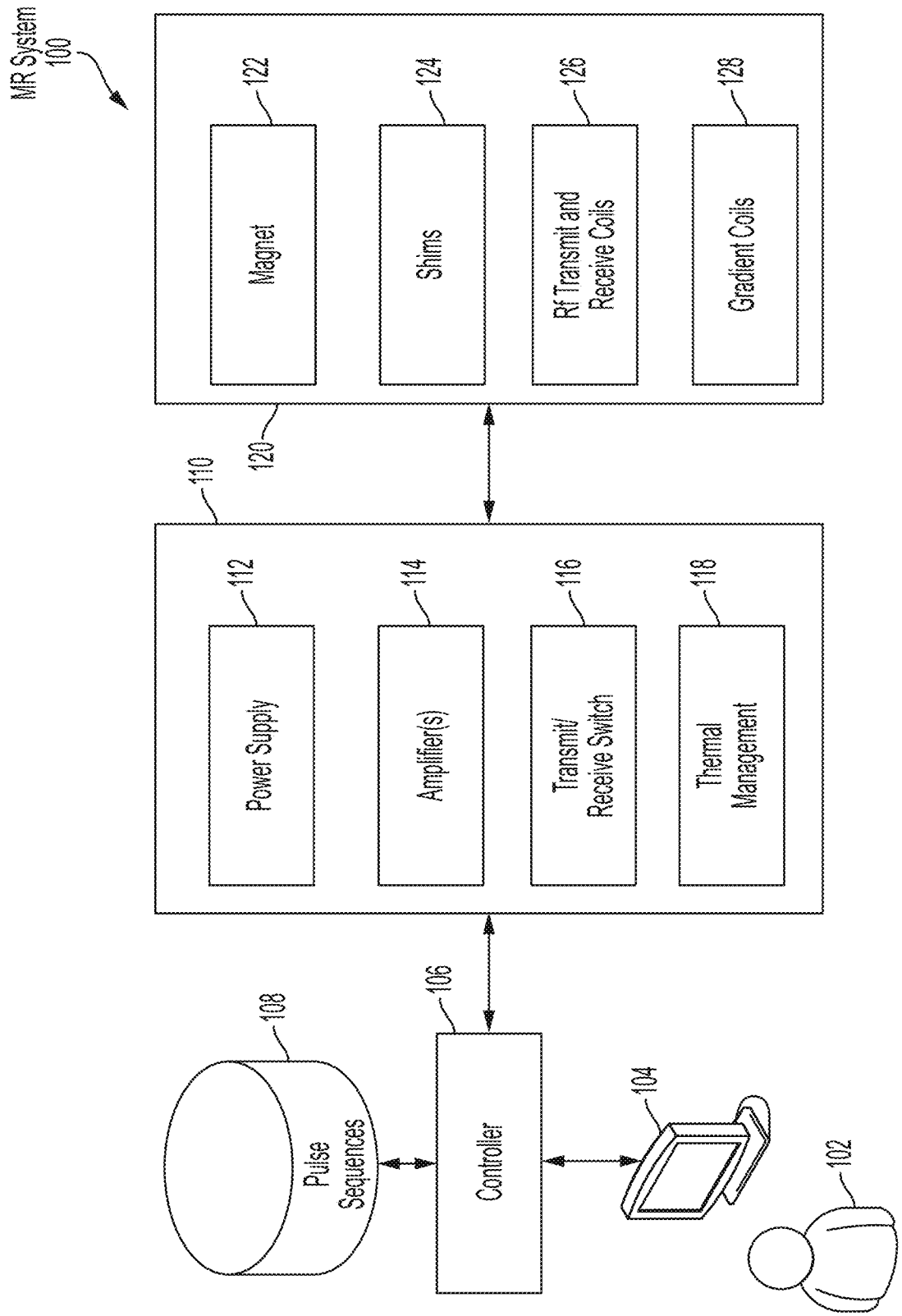
FIG. 1 is a drawing of an illustrative magnetics system on which techniques of detecting and suppressing electromagnetic noise conducted by a patient may be performed, in accordance with some embodiments of the technology described herein.

The MRI scanner market is overwhelmingly dominated by high-field systems, and particularly for medical or clinical MRI applications. As described above, the general trend in medical imaging has been to produce MRI scanners with increasingly greater field strengths, with the vast majority of clinical MRI scanners operating at 1.5 Tesla (T) or 3 T, with higher field strengths of 7 T and 9 T used in research settings. As used herein, "high-field" refers generally to MRI systems presently in use in a clinical setting and, more particularly, to MRI systems operating with a main magnetic field (i.e., a $B_0$ field) at or above 1.5 T, though clinical systems operating between 0.5 T and 1.5 T are often also characterized as "high-field." Field strengths between approximately 0.2 T and 0.5 T have been characterized as "mid-field" and, as field strengths in the high-field regime have continued to increase, field strengths in the range between 0.5 T and 1.0 T have also been characterized as mid-field. By contrast, "low-field" refers generally to MRI systems operating with a $B_0$ field of less than or equal to approximately 0.2 T, though systems having a $B_0$ field of between 0.2 T and approximately 0.3 T have sometimes been characterized as low-field as a consequence of increased field strengths at the high end of the high-field regime. Within the low-field regime, low-field MRI systems operating with a $B_0$ field of less than 0.1 T are referred to herein as "very low-field" and low-field MRI systems operating with a $B_0$ field of less than 10 milliTesla (mT) are referred to herein as "ultra-low field."

As described above, conventional MRI systems require specialized facilities. An electromagnetically shielded room is required for the MRI system to operate and the floor of the room must be structurally reinforced. Additional rooms must be provided for the high-power electronics and the scan technician's control area. Secure access to the site must also be provided. In addition, a dedicated three-phase electrical connection must be installed to provide the power for the electronics that, in turn, are cooled by a chilled water supply. Additional HVAC capacity typically must also be provided. These site requirements are not only costly, but significantly limit the locations where MRI systems can be deployed. Conventional clinical MRI scanners also require substantial expertise to both operate and maintain. These highly trained technicians and service engineers add large on-going operational costs to operating an MRI system. Conventional MRI, as a result, is frequently cost prohibitive and is severely limited in accessibility, preventing MRI from being a widely available diagnostic tool capable of delivering a wide range of clinical imaging solutions wherever and whenever needed. Typically, patient must visit one of a limited number of facilities at a time and place scheduled in advance, preventing MRI from being used in numerous medical applications for which it is uniquely efficacious in assisting with diagnosis, surgery, patient monitoring and the like.

As described above, high-field MRI systems require specially adapted facilities to accommodate the size, weight, power consumption and shielding requirements of these systems. For example, a 1.5 T MRI system typically weighs between 4-10 tons and a 3 T MRI system typically weighs between 8-20 tons. In addition, high-field MRI systems generally require significant amounts of heavy and expensive shielding. To accommodate this heavy equipment, rooms (which typically have a minimum size of 30-50 square meters) have to be built with reinforced flooring (e.g., concrete flooring), and must be specially shielded to prevent electromagnetic radiation from interfering with operation of the MRI system. Thus, available clinical MRI systems are immobile and require the significant expense of a large, dedicated space within a hospital or facility, and in addition to the considerable costs of preparing the space for operation, require further additional on-going costs in expertise in operating and maintaining the system. The many physical requirements of deploying conventional clinical MRI systems create a significant problem of availability, and severely restrict the clinical applications for which MRI can be utilized.

Accordingly, low-field MRI systems may be desirable for clinical use, for example, to provide point-of-care MRI outside specially shielded rooms, as described in further detail below. However, there are numerous challenges to developing a clinical MRI system in the low-field regime. As used herein, the term clinical MRI system refers to an MRI system that produces clinically useful images, which refers to images having sufficient resolution and adequate acquisition times to be useful to a physician or clinician for its intended purpose given a particular imaging application. As such, the resolutions/acquisition times of clinically useful images will depend on the purpose for which the images are being obtained.

Among the numerous challenges in obtaining clinically useful images in the low-field regime is the relatively low signal-to-noise ratio (SNR). Specifically, the relationship between SNR and $B_0$ field strength is approximately $B_0^{5/4}$ at field strength above 0.2 T and approximately $B_0^{3/2}$ at field strengths below 0.1 T. As such, the SNR drops substantially with decreases in field strength with even more significant drops in SNR experienced at very low field strength. This substantial drop in SNR resulting from reducing the field strength is a significant factor that has prevented development of clinical MRI systems in the very low-field regime. In particular, the challenge of the low SNR at very low field strengths has prevented the development of a clinical MRI system operating in the very low-field regime. As a result, clinical MRI systems that seek to operate at lower field strengths have conventionally achieved field strengths of approximately the 0.2 T range and above. These MRI systems are still large, heavy and costly, generally requiring fixed dedicated spaces (or shielded tents) and dedicated power sources.

The inventors have developed techniques for producing improved quality, portable and/or lower-cost low-field MRI systems that can improve the wide-scale deployability of MRI technology in a variety of environments beyond the large MRI installments at hospitals and research facilities. As such, low-field MRI presents an attractive imaging solution, providing a relatively low cost, and high availability alternative to high-field MRI. In particular, low-field MRI systems can be implemented as self-contained systems that are deployable in a wide variety of clinical settings where high-field MRI systems cannot, for example, by virtue of being transportable, cartable or otherwise generally mobile so as to be deployable where needed. As a result, such low-field MRI systems may be expected to operate in generally unshielded or partially shielded environments (e.g., outside of specially shielded rooms or encompassing cages) and handle the particular noise environment in which they are deployed.

Some aspects of the inventors' contribution derive from their recognition that performance of a flexible low-field MRI systems (e.g., a generally mobile, transportable or cartable system and/or a system that can be installed in a variety of settings such as in an emergency room, office or clinic) may be particularly vulnerable to noise, such as RF interference, to which many conventional high field MRI systems are largely immune due to being installed in specialized rooms with extensive shielding. In particular, such systems may be required to operate in unshielded or partially shielded environments, as well as in multiple environments that may have different and/or variable sources of noise to contend with. High levels of noise may cause the SNR of the system to further decline, compromising the quality of images obtained. Accordingly, aspects of the technology described herein relate to improving the performance of low-field MRI systems in environments where the presence of noise, such as RF interference, may adversely impact the performance of such systems.

The inventors have recognized that a patient's body may introduce electromagnetic radiation from the surrounding environment into a low-field MRI system (e.g., a partially-shielded low-field MRI system adapted to operate outside specially shielded rooms) as electromagnetic interference (EMI) or noise. For example, at an operational frequency range of a low-field MRI system, the patient's body may act like an antenna and capture electromagnetic radiation present in the environment of the low-field MRI system. In turn, the patient's body may conduct the electromagnetic radiation that couples to the body and introduce this energy into a portion of the low-field MRI system as electromagnetic noise that negatively impacts operation of the low-field MRI system (e.g., by decreasing SNR and reducing image quality). For example, the patient's body may conduct electromagnetic energy (e.g., electromagnetic radiation from the environment that couples to the patient's body) and radiate the electromagnetic energy into a region (e.g., the imaging region) where it will be detected as noise by one or more RF receive coils configured to detect MR signals, thus reducing the SNR of the system. Electromagnetic noise that is introduced into the MRI system by the patient may be distinguished from electromagnetic noise in the operating environment of the MRI system by detecting noise in a region (e.g., the imaging region) of the MRI system with and without a patient being positioned in the region. For example, noise introduced by the patient may be quantified by subtracting noise detected when the patient is not positioned in the region from noise detected when the patient is positioned in the region.

This introduction of electromagnetic noise into the MRI system by the patient does not typically occur in conventional high-field MRI systems because such systems are operated in specially shielded environments, and their specialized shielding prevents electromagnetic radiation from reaching and being conducted by the patient's body. Specifically, conventional high-field MRI systems are installed in tightly shielded rooms so that there is no electromagnetic radiation in the environment to couple to the patient's body. By contrast, low-field MRI systems developed by the inventors are configured to be operated outside of specially shielded environments (e.g., portable MRI systems developed by the inventors are designed to provide point-of-care MRI and therefore are capable of operating in arbitrary environments). In such settings, the patient's body may be generally exposed to the environment and is therefore susceptible to coupling with electromagnetic radiation that is noise from the perspective of the MRI system (e.g., environmental electromagnetic noise, noise generated by other devices in the environment of the low-field MRI system), which electromagnetic energy is effectively absent in the specially shielded environments of conventional high-field MRI systems. This electromagnetic noise introduced by the patient's body reduces the SNR of the low-field MRI system, which in turn adversely impacts the quality of the images obtained by the low-field MRI system.

It should be appreciated that the operational frequency range of the low-field MRI system may include frequencies at which electromagnetic noise may influence, impact, and/or degrade the ability of the MRI system to excite and detect an MR response. In general, the operational frequency range of an MRI system corresponds to a frequency range around a nominal operating frequency (i.e., the Larmor frequency) at a given $B_0$ magnetic field strength for which the receive system is configured to or capable of detecting. This frequency range is referred to herein as an operational frequency range for the MRI system. For example, for a $B_0$ magnetic field strength of 0.1 T, the nominal operating frequency may be approximately 4 MHz, and the operational frequency range of the MRI system may be 2 KHz-10 MHz. Thus, there may be a wide frequency range of electromagnetic radiation with the potential of negatively impacting low-field MRI, particularly point-of-care systems designed to be operated in arbitrary and unshielded environments.

The inventors have developed electromagnetic interference (also referred to herein as electromagnetic noise) detection and suppression techniques for use with low-field MRI systems to eliminate or mitigate electromagnetic radiation captured and conducted by the patient's body, thus eliminating or reducing its impact on the operation of the low-field MRI systems. By detecting noise conducted by the patient's body (e.g., electromagnetic radiation from the environment that couples to the patient), such as by electrically coupling to the patient using a sensor of the MRI system, the detected noise may be suppressed or compensated for. For example, detected noise may be provided to a noise reduction system of the MRI system, which may compensate for the detected noise when processing received MRI signals. Thus, the impact of this noise on the operation of a low-field MRI system may be reduced or eliminated. The techniques developed by the inventors for detecting and suppressing electromagnetic noise conducted by the patient during imaging by low-field MRI systems thereby improve low-field MRI technology by facilitating operation of low-field MRI systems in unshielded or partially shielded environments.

Another technique developed by the inventors to address electromagnetic noise that couples to and is introduced to an MRI system by a patient's body is to ground the patient. By grounding the patient, electromagnetic radiation that couples to the patient's body is provided a path to ground (or any suitable reference potential) to prevent at least some of electromagnetic radiation from being picked up by receive coils of the MR system. In contrast to patient grounding, detection and suppression techniques described herein do not necessarily provide a path to ground. Rather, as described herein, noise may be captured, processed, and suppressed from MR signals received during imaging. In some embodiments, patient grounding techniques and noise detection and suppression techniques may be used in combination, such as by providing a path to ground for some electromagnetic noise coupled from the patient and capturing some noise and suppressing the captured noise from MR signals received during imaging. Patient grounding techniques are described further in U.S. Pat. Application Publication No. 2020/0200844, titled "System and Methods for Grounding Patients During Magnetic Resonance Imaging," which is herein incorporated by reference in its entirety.

Noise detection and suppression techniques described herein include detecting electromagnetic noise conducted by a patient using a sensor of an MRI system. For example, the sensor may be positioned in or about an imaging region of the MRI system. By electrically coupling to electromagnetic noise conducted by the patient (e.g., via an electrical conductor, via capacitive or inductive coupling, or in any other suitable way), the electromagnetic noise may be measured or otherwise acquired or detected and provided to the MRI system for processing, facilitating suppression of the electromagnetic noise from received MRI signals, thereby improving the quality of images constructed using the received MRI signals. It should be appreciated that the noise detection and suppression techniques described herein are distinct from prior patient grounding techniques at least because electromagnetic noise is suppressed by first detecting or measuring electromagnetic radiation that couples to the patient's body, whereas patient grounding techniques suppress noise by providing a path to ground (or another suitable reference potential) without detecting, sensing or otherwise measuring the electromagnetic noise (e.g., without quantifying the noise or otherwise producing signals indicative of the electromagnetic noise introduced by the patient).

Sensors described herein for detecting electromagnetic interference or noise conducted by a patient (e.g., electromagnetic radiation in the environment that couples to the patient's body) may be configured to conductively couple (e.g., via an electrical conductor) to the patient, such as by being positioned to physically contact the patient. For example, a sensor may have an electrically conductive pad positioned on a surface of the MRI system which supports at least a portion of the patient during imaging, positioned on or within a radio frequency component of the MRI system that is used to excite and/or detect magnetic resonance signals and accommodate the patient's anatomy, etc. Alternatively or additionally, the electrically conductive pad may be configured to be worn by the patient during imaging (e.g., around the patient's neck during head imaging, around the patient's leg during foot imaging, etc.). In some cases, a sensor may include an electrically conductive patch (e.g., adhesive electrode) configured for attaching to the patient.

Moreover, some sensors described herein may be configured to couple to the patient capacitively, such as by being positioned within a capacitive coupling range of the patient. For example, a sensor may include an electric field detector (EFD) positioned in or around the imaging region of the MRI system such that the EFD is within capacitive coupling range of the patient during imaging. Capacitive coupling of electromagnetic noise may occur or be achieved at operational frequencies of the MRI system (e.g., the Larmor frequency) to facilitate detection of electromagnetic noise at such frequencies. Alternatively or additionally, such capacitive coupling may occur or be achieved at frequencies having high noise spectral density (e.g., above an average taken from DC to the highest frequency of the system) which may contribute substantially to the integrated noise power seen by the system. It should be appreciated that some sensors may be configured for both conductive and capacitive coupling to patients, such as some embodiments of electrically conductive pads and patches described further herein.

The noise detection and suppression techniques described herein may be used with any suitable low-field or high-field MRI systems deployed in virtually any facility, including portable and cartable MRI systems and/or any other type of point-of-care MRI system (e.g., MRI systems that can be transported to the patient, for example, moved to the bedside of the patient, MRI systems that are locally deployed so that a patient can be transported to the local installation, for example, the patient's bed can be moved to the MRI system and/or any other MRI system that is generally available at or near the point-of-care). While aspects of noise detection and suppression techniques described herein may be particularly beneficial in the low-field context where extensive shielding may be unavailable or otherwise not provided, it should be appreciated that the techniques described herein are also suitable in the high-field context and are not limited for use with any particular type of MRI system.

Following below are more detailed descriptions of various concepts related to, and embodiments of, isolating noise conducted by a patient during MR imaging. It should be appreciated that various aspects described herein may be implemented in any of numerous ways. Examples of specific implementations are provided herein for illustrative purposes only. In addition, the various aspects described in the embodiments below may be used alone or in any combination, and are not limited to the combinations explicitly described herein.

FIG. 1 is a drawing of exemplary components of an illustrative MRI system 100 for which techniques of detecting electromagnetic noise conducted by a patient may be applied, in accordance with some embodiments of the technology described herein. In the illustrative embodiment of FIG. 1, MRI system 100 includes control components, power system 110, and magnetics system 120.

As illustrated in FIG. 1, magnetics components 120 include $B_0$ magnet 122, shim coils 124, RF transmit and receive coils 126, and gradient coils 128. The $B_0$ magnet 122 may generate the main magnetic field $B_0$. The $B_0$ magnet 122 may be any suitable type or combination of magnetics components that can generate a desired main magnetic $B_0$ field. For example, the $B_0$ magnet 122 may be a permanent magnet, an electromagnet, or a hybrid magnet comprising at least one permanent magnet and at least one electromagnet. In some embodiments, $B_0$ magnet 122 may include one or more permanent magnets formed of ferromagnetic materials. For example, $B_0$ magnet 122 may include permanent magnet rings arranged in a circular pattern, such as concentric permanent magnet rings. In some embodiments, $B_0$ magnet 122 may include a bi-planar magnet structure positioned on opposite sides of an imaging region. In some embodiments, $B_0$ magnet 122 may include a hybrid magnet having permanent magnets and coils driven with electromagnetic signals. $B_0$ magnets are described further in U.S. Pat. Application Publication No. 2018/0143274, titled "Low-Field Magnetic Resonance Imaging Methods and Apparatus," which is herein incorporated by reference in its entirety.

In some embodiments, shims 124 may include one or more permanent magnet shims arranged to improve the profile of the $B_0$ magnetic field produced by $B_0$ magnet 122, and/or one or more shim coils driven with electromagnetic signals configured improve $B_0$ field homogeneity, thereby addressing the relatively low SNR characteristic of the low-field regime. In general, a $B_0$ magnet requires some level of shimming to produce a $B_0$ magnetic field with a profile (e.g., a $B_0$ magnetic field at the desired field strength and/or homogeneity) satisfactory for use in MRI. In particular, production factors such as design, manufacturing tolerances, imprecise production processes, environment, etc., give rise to field variation that produces a $B_0$ field having unsatisfactory profile after assembly/manufacture. For example, after production, $B_0$ magnet 122 described above may produce a $B_0$ field with an unsatisfactory profile (e.g., inhomogeneity in the $B_0$ field unsuitable for imaging) that needs to be improved or otherwise corrected, typically by shimming, to produce clinically useful images.

Shimming refers to any of various techniques for adjusting, correcting and/or improving a magnetic field, often the $B_0$ magnetic field of a magnetic resonance imaging device. Similarly, a shim refers to something (e.g., an object, component, device, system or combination thereof) that performs shimming (e.g., by producing a magnetic field). Further aspects of shim techniques for use in low-field MRI systems, such as shims 124 of MRI system 100, are described in U.S. Pat. Application Publication No. 2018/0164390 ('390 Publication), titled "Electromagnetic Shielding For Magnetic Resonance Imaging Methods and Apparatus," and U.S. Pat. No. 10,145,913 ('913 patent), each of which is herein incorporated by reference in its entirety.

In some embodiments, RF transmit and receive coils 126 are configured to transmit MR signals. MRI is performed by exciting and detecting emitted MR signals using transmit and receive coils, respectively (often referred to as radio frequency (RF) coils). Transmit/receive coils may include separate coils for transmitting and receiving, multiple coils for transmitting and/or receiving, or the same RF coil(s) for transmitting and receiving. Thus, a transmit/receive component may include one or more coils for transmitting, one or more coils for receiving, and/or one or more coils for transmitting and receiving. Transmit/receive coils are also often referred to as Tx/Rx or Tx/Rx coils to generically refer to the various configurations for the transmit and receive magnetics component of an MRI system. These terms are used interchangeably herein.

In FIG. 1, RF transmit and receive coils 126 include one or more transmit coils that may be used to generate RF pulses to induce an oscillating magnetic field $B_1$. The RF transmit coil(s) may be configured to generate any suitable types of RF pulses. Further aspects of RF transmit and/or receive coils for use in low-field systems, such as RF transmit and receive coils 126 of MRI system 100, are described in the '390 Publication.

In some embodiments, gradient coils 128 may be arranged to provide gradient fields and, for example, may be arranged to generate gradients in the $B_0$ field in three substantially orthogonal directions (X, Y, Z). Gradient coils 128 may be configured to encode emitted MR signals by systematically varying the $B_0$ field (the $B_0$ field generated by magnet 122 and/or shim coils 124) to encode the spatial location of received MR signals as a function of frequency and/or phase. For example, gradient coils 128 may be configured to vary frequency and/or phase as a linear function of spatial location along a particular direction, although more complex spatial encoding profiles may also be provided by using nonlinear gradient coils. For example, a first gradient coil may be configured to selectively vary the $B_0$ field in a first (X) direction to perform frequency encoding in that direction, a second gradient coil may be configured to selectively vary the $B_0$ field in a second (Y) direction substantially orthogonal to the first direction to perform phase encoding, and a third gradient coil may be configured to selectively vary the $B_0$ field in a third (Z) direction substantially orthogonal to the first and second directions to enable slice selection for volumetric imaging applications. Further aspects of gradient coils for use in low-field systems, such as gradient coils 128 of MRI system 100, are described in the '390 Publication.

In some embodiments, power system 110 includes electronics to provide operating power to one or more components of the low-field MRI system 100. As illustrated in FIG. 1, power system 110 includes power supply 112, power component(s) 114, transmit/receive switch 116, and thermal management components 118 (e.g., one or more air cooling components such as fans or forced air, one or more liquid cooling components, such as a water cooling system, etc.). Power supply 112 includes electronics to provide operating power to magnetic components 120 of MRI system 100. For example, power supply 112 may include electronics to provide operating power to one or more $B_0$ coils (e.g., $B_0$ magnet 122) to produce the main magnetic field for the low-field MRI system (e.g., in embodiments where the main magnetic field is produced at least in part by one or more electromagnets). Transmit/receive switch 116 may be used to select whether RF transmit coils or RF receive coils are being operated. Power component(s) 114 may include one or more RF receive (Rx) pre-amplifiers that amplify MR signals detected by one or more RF receive coils (e.g., coils 126), one or more RF transmit (Tx) power components configured to provide power to one or more RF transmit coils (e.g., coils 126), one or more gradient power components configured to provide power to one or more gradient coils (e.g., gradient coils 128), and/or one or more shim power components configured to provide power to one or more shim coils (e.g., for embodiments in which shims 124 include one or more shim coils).

As illustrated in FIG. 1, control components of MRI system 100 include controller 106 having control electronics to send instructions to and receive information from power system 110. Controller 106 may be configured to implement one or more pulse sequences, which are used to determine the instructions sent to power system 110 to operate magnetic components 120 in a desired sequence. For example, in MRI system 100, controller 106 may be configured to control power system 110 to operate the magnetic components 120 in accordance with a balance steady-state free precession (bSSFP) pulse sequence, a low-field gradient echo pulse sequence, a low-field spin echo pulse sequence, a low-field inversion recovery pulse sequence, fluid attenuation inversion recovery (FLAIR) pulse sequence, diffusion weighted imaging (DWI) pulse sequence, and/or any other suitable pulse sequence. Controller 106 may be implemented as hardware, software, or any suitable combination of hardware and software, as aspects of the disclosure provided herein are not limited in this respect.

In some embodiments, controller 106 may be configured to implement a pulse sequence by obtaining information about the pulse sequence from pulse sequences repository 108, which stores information for each of one or more pulse sequences. Information stored by pulse sequences repository 108 for a particular pulse sequence may be any suitable information that allows controller 106 to implement the particular pulse sequence. For example, information stored in pulse sequences repository 108 for a pulse sequence may include one or more parameters for operating magnetics components 120 in accordance with the pulse sequence (e.g., parameters for operating the RF transmit and receive coils 126, parameters for operating gradient coils 128, etc.), one or more parameters for operating power system 110 in accordance with the pulse sequence, one or more programs including instructions that, when executed by controller 106, cause controller 106 to control MRI system 100 to operate in accordance with the pulse sequence, and/or any other suitable information. Information stored in pulse sequences repository 108 may be stored on one or more non-transitory storage media.

As illustrated in FIG. 1, controller 106 also interacts with computing device 104 programmed to process received MR data. For example, computing device 104 may process received MR data to generate one or more MR images using any suitable image reconstruction process(es). Controller 106 may provide information about one or more pulse sequences to computing device 104 for the processing of data by the computing device. For example, controller 106 may provide information about one or more pulse sequences to computing device 104 and the computing device may perform an image reconstruction process based, at least in part, on the provided information.

In some embodiments, computing device 104 may process acquired MR data and generate one or more images of the subject being imaged. In some embodiments, computing device 104 may be a fixed electronic device such as a desktop computer, a server, a rack-mounted computer, or any other suitable fixed electronic device that may be configured to process MR data and generate one or more images of the subject being imaged. Alternatively, in some embodiments, computing device 104 may be a portable device such as a smart phone, a personal digital assistant, a laptop computer, a tablet computer, or any other portable device that may be configured to process MR data and generate one or images of the subject being imaged. In some embodiments, computing device 104 may include multiple computing devices of any suitable type, as the aspects are not limited in this respect. A user 102 may interact with workstation 104 to control aspects of MRI system 100 (e.g., program MRI system 100 to operate in accordance with a particular pulse sequence, adjust one or more parameters of MRI system 100, etc.) and/or view images obtained by MRI system 100.

Figure 2:
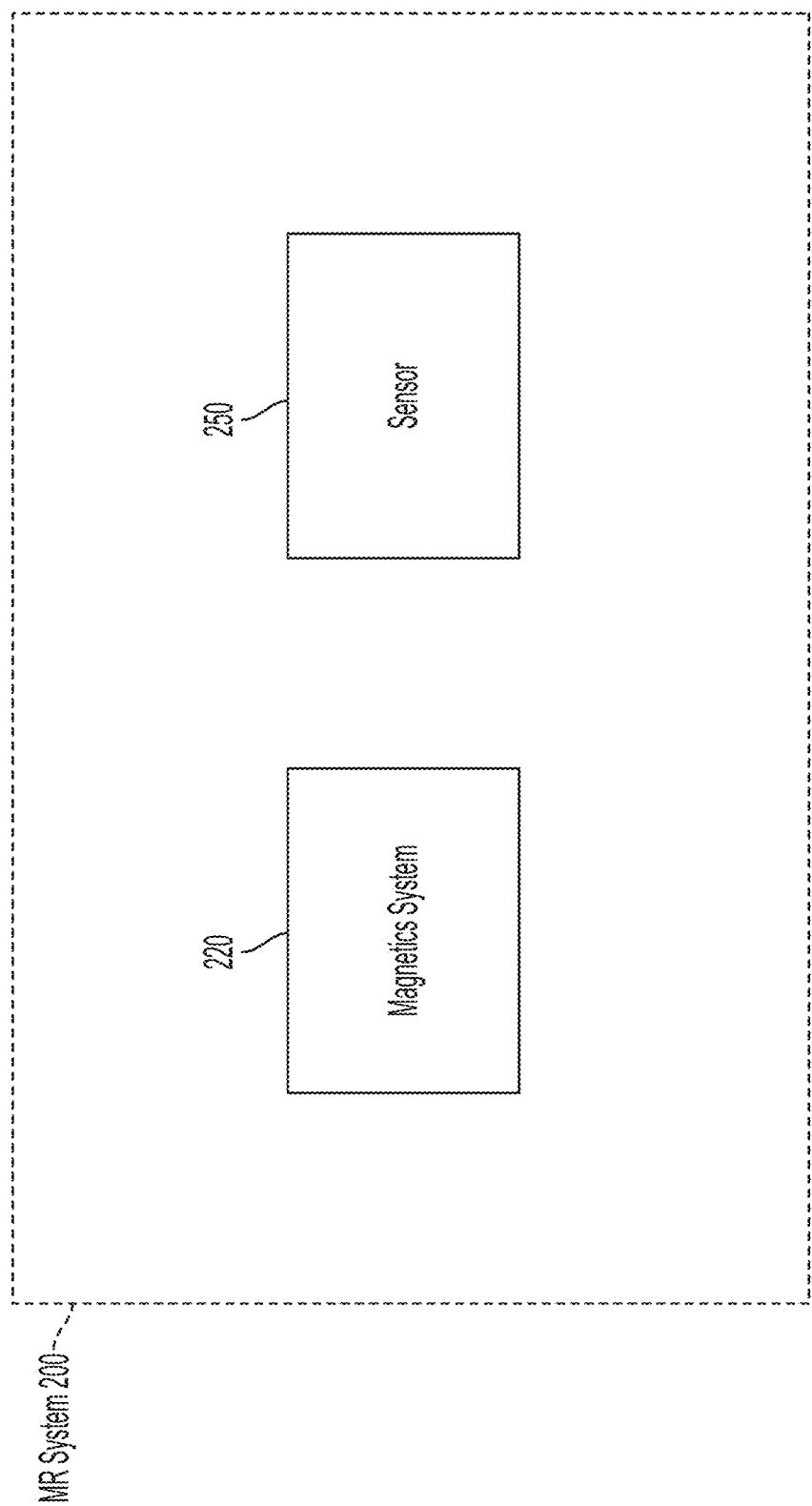
FIG. 2 is a drawing of an illustrative magnetic resonance imaging (MRI) system configured to detect electromagnetic noise conducted by a patient, in accordance with some embodiments of the technology described herein.

FIG. 2 is a system level schematic drawing of portions of an illustrative MRI system 200 configured to detect electromagnetic noise conducted by a patient, in accordance with some embodiments of the technology described herein. MRI system 200 includes magnetics system 220 and sensor 250. MRI system 200 may be any suitable type of MRI system and, in some embodiments, may be a low-field MRI system. For example, MRI system 200 may operate with a $B_0$ magnetic field having a field strength of less than or equal to approximately 0.2 T, less than or equal to approximately 0.1 T, and/or in the range of 0.5-0.1 T. The choice of magnetic field strength will depend on the requirements of the particular MRI system. For example, as field strength increases, the size, weight and cost of the system also generally increases along with the SNR. Thus, in the low-field context, MRI systems that tend toward the 0.2 T range may be more suitable for MRI systems that are permanently or semi-permanently installed within a facility (e.g., in an emergency room, operating room, etc.), while MRI systems in the 20 mT to 0.1 T range (e.g., a 20 mT, 50 mT, 64 mT, 72 mT, 0.1 T system, etc.) may be more suitable for MRI systems that are intended to be transported to different locations (e.g., moved to different points-of-care). Thus, the specific choice of field strength will depend on the intent, design and requirements of the particular MRI system.

In the illustrative embodiment of FIG. 2, MRI system 200 is configured to detect electromagnetic noise conducted by a patient using sensor 250. For example, magnetics system 220 may generate magnetic fields for imaging the patient (e.g., magnetics system 220 may include, but is not limited to, any one or combination of magnetics components described in connection with magnetic system 120 illustrated in FIG. 1), and sensor 250 may include one or more electrical conductors configured to capacitively and/or conductively couple to the patient to conduct electromagnetic noise introduced by the patient (e.g., by the patient's body coupling to electromagnetic radiation in the environment) during imaging. In some embodiments, detecting electromagnetic noise by sensor 250 may facilitate suppression of the detected electromagnetic noise in MRI signals detected by system 200, improving the quality of images produced by MRI system 200 in the presence of noise. For example, by sensing the amount of electromagnetic noise introduced by the patient, the detected electromagnetic noise may be used to modify or adjust magnetic resonance signals received by magnetics system 120, or signals derived therefrom, to compensate for the electromagnetic noise introduced by the patient.

In some embodiments, sensor 250 may include one or more electrical conductors configured to conductively couple to (e.g., physically contact) the patient, such that electromagnetic noise conducted by the patient is conductively coupled by the electrical conductor(s). For example, sensor 250 may include a conductive pad positioned on a surface of MRI system 200 to support the patient during imaging. During imaging, the patient may lie on the surface thereby contacting the conductive pad and conductively coupling to sensor 250. In another example, sensor 250 may include a conductive patch configured to attach to the patient, such as an adhesive electrode to be worn by the patient during imaging. The conductive patch may be attached to the patient prior to and/or during imaging such that sensor 250 is conductively coupled to the patient.

Alternatively or additionally, in some embodiments, the electrical conductor(s) may be configured to capacitively couple to the patient. For example, when one or more electrical conductors is positioned in close enough proximity to the patient, at least some electromagnetic noise from the patient (e.g., portions above a particular frequency defined by the capacitance) may couple to sensor 250 via the capacitive relationship between the patient and the sensor. Accordingly, the electrical conductor(s) may be configured to capacitively couple to the patient when positioned within a capacitive coupling range of the patient during imaging. It should be appreciated that capacitive coupling is frequency-dependent and so the minimum or maximum spacing between the patient and the electrical conductor(s) required to achieve meaningful levels of capacitive coupling may depend upon several factors including the operating frequency of the MRI system, the medium separating the electrical conductor(s) from the patient, the size (e.g., surface area) of the electrical conductor(s) and the patient, etc.

In some embodiments, sensor 250 may include an electric field detector (EFD), such as a near-field antenna, positioned for capacitively coupling to (e.g., within capacitive coupling range of) the patient during imaging. The EFD may be positioned such that when at least a portion of the patient is in an imaging region of the MRI system 200, the EFD is within capacitive coupling range of the patient. According to some embodiments, the EFD comprises at least one conductor (e.g., at least one strip of conductive material) provided within the MRI system so that when the patient is positioned for imaging, a sufficient capacitive relationship between the at least one conductor and the patient is established (e.g., the at least one conductor may be provided on or within a radio frequency component of the MRI system, provided on a surface within an imaging region of the MRI system or otherwise suitably arranged to capacitively couple to the patient, including by being attached to the patient).

In some embodiments, the EFD may include a printed circuit board (PCB) with electrical conductor(s) positioned (e.g., soldered, plated, etched, etc.) on a substrate layer of the PCB. In some embodiments, the PCB may be a flexible PCB, such as made using a plastic substrate (e.g., polyimide), which may facilitate placement of the PCB in, on or around components of MRI system 200 and/or proximate the imaging region of the MRI system. For example, the EFD may be supported by one of the MRI system's magnetics components, such as a radio frequency component (e.g., a head or foot coil, etc.), configured to accommodate a portion of the patient's anatomy (e.g., head, foot, etc.) during imaging. The EFD may capacitively couple to the portion of the patient's anatomy that is accommodated by the magnetics component during imaging.

It should be appreciated that some embodiments of sensor 250 may be adapted for conductive or capacitive coupling to the patient. For example, by placing an insulating layer over a conductive pad positioned on a patient support surface, such as for patient comfort, the conductive pad may capacitively couple to the patient through the insulating layer when the patient lies on the support surface. Alternatively or additionally, an insulating layer may be placed on a conductive patch to contact the patient, such that the conductive patch capacitively couples to the patient through the insulating layer when the conductive patch is worn by the patient.

Figure 3:
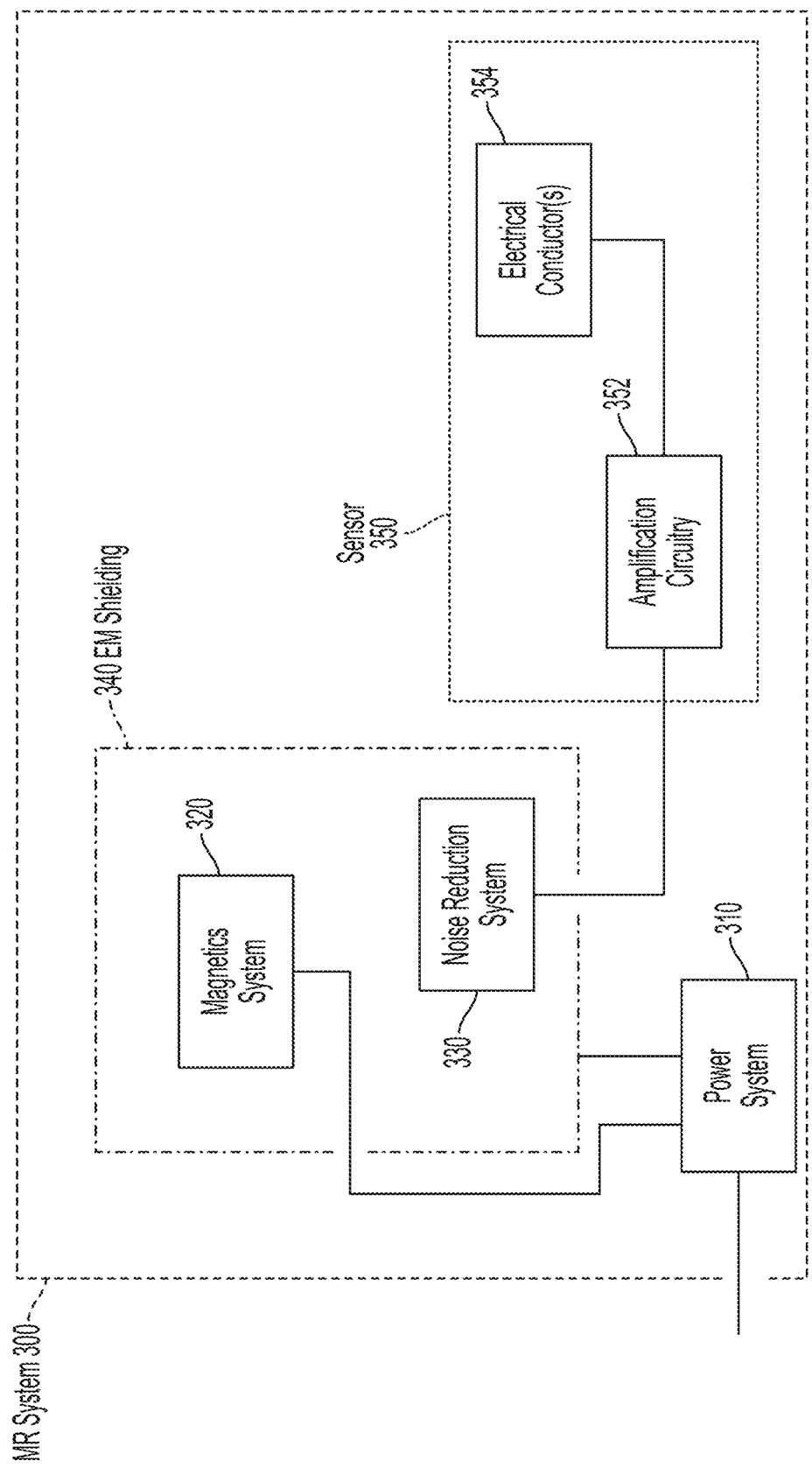
FIG. 3 is a drawing of an illustrative MRI system configured to detect and suppress electromagnetic noise conducted by a patient, in accordance with some embodiments of the technology described herein.

FIG. 3 is a system level schematic drawing of portions of an illustrative MRI system 300 configured to detect and suppress electromagnetic noise conducted by a patient, in accordance with some embodiments of the technology described herein. MRI system 300 may be configured in the manner described for MRI system 200 (e.g., MRI system may include magnetics system 320 and sensor 350, the latter facilitating detection of electromagnetic noise in the patient during imaging. MRI system 300 further includes power system 310 (e.g., a power system that may include, but is not limited to, any one or combination of components described in connection with power system 110 illustrated in FIG. 1), noise reduction system 330, and electromagnetic shielding 340. Noise reduction system 330 may be configured to suppress electromagnetic noise present in magnetic resonance signals received by magnetics system 310 during imaging based on electromagnetic noise detected by sensor 350 (e.g., by compensating for the detected electromagnetic noise by adjusting, modifying or otherwise augmenting magnetic resonance signals received by magnetics system 320). Such suppression may improve the quality of images produced by MRI system 300 in the presence of noise.

Magnetics system 320 may include one or more magnetics components configured to provide magnetic fields used in performing magnetic resonance imaging of a patient (e.g., performing MRI of a portion of the anatomy of the patient), for example, any one or combination of magnetics components described in connection with magnetics system 120 illustrated in FIG. 1, though magnetics system 320 is not limited in this respect. For example, magnetics system 320 may include one or more magnets that produce and/or are configured to produce a $B_0$ magnetic field for MRI system 300. Magnetics system 320 may include one or more gradient coils configured to generate magnetic fields to provide spatial encoding of emitted magnetic resonance signals.

Magnetics system 320 may include one or more radio frequency (RF) components comprising one or more coils configured to transmit RF signals to a field of view of MRI system 300, and/or to receive MRI signals emitted from the field of view. The one or more coils configured to transmit RF signals and/or receive MRI signals may be separate coils or may be the same coils for both transmitting and receiving. Thus, the term transmit/receive coil or coils refers herein to the set of one or more coils that transmit RF signals and receive RF signals, independent of whether the one or more coils perform transmit only, receive only and/or both transmit and receive. Magnetics system 320 may include one or more shim coils configured to improve homogeneity of the $B_0$ field.

As shown in FIG. 3, sensor 350 further includes amplification circuitry 352 and one or more electrical conductors 354. In some embodiments, electrical conductor(s) 354 may be configured for conductively and/or capacitively coupling to the patient, so as to couple electromagnetic noise conducted by the patient and provide detected magnetic noise to noise reduction system 330 via amplification circuitry 352. For example, electrical conductor(s) 354 may include one or more conductive strips (e.g., electrically conductive tape, flexible PCB, etc.), may include an electrically conductive pad, and/or may include an electrically conductive patch, examples of which are described in further detail below.

Amplification circuitry 352 is configured to receive electromagnetic noise detected by sensor 350 so that it can be suitably provided to noise reduction system 330. For example, amplification circuitry 352 may amplify the electromagnetic noise to facilitate suppression techniques employed by noise reduction system 330. For example, electromagnetic noise coupled from the patient to electrical conductor(s) 354 may have very low power (e.g., on the order of nano-Watts), which may be unsuitable or otherwise inadequate for desired processing by noise reduction system 330. Amplification circuitry 352 may multiply the power level of the electromagnetic noise (e.g., by 100, by 1,000, etc.) to a suitable amplitude for processing by noise reduction system 330. Exemplary embodiments of amplification circuitry are described further herein including with reference to FIGS. 10A-10B. It should be appreciated that some embodiments do not include amplification circuitry. For example, noise reduction system 330 may have low enough sensitivity to receive electromagnetic noise without amplification. In other embodiments, amplification circuitry performs other processing of electromagnetic noise detected by sensor 350 (e.g., signal conversion), with or without amplification, so that detected electromagnetic noise is suitably provided to noise reduction system 330.

Noise reduction system 330 may be configured to characterize noise in the environment of MRI system 300 and to suppress or remove the characterized noise from detected MR signals, or otherwise compensate for the detected electromagnetic noise characterized by the noise reduction system (e.g., electromagnetic noise characterized by signals generated by sensor 350). For instance, noise reduction system 330 may be configured to detect MR signals emitted by a patient during imaging using one or more of the RF coils of magnetics system 320. Noise reduction system 330 may be configured to analyze the detected electromagnetic noise and compensate for the noise in the detected MR signals. For example, based on analysis of the electromagnetic noise, noise reduction system 330 may generate a transfer function for applying to the detected MR signals which may remove at least some of the detected electromagnetic noise from the detected signals. Thus, by detecting electromagnetic noise using sensor 350, noise reduction system 330 may suppress noise present in the detected signals. In some embodiments, noise reduction system 330 may include a primary RF receive coil, tuning circuitry, an acquisition system and/or one or more auxiliary sensors.

The auxiliary sensors may be configured to detect electromagnetic noise in the environment, including ambient electromagnetic noise, electromagnetic noise produced by other sources in the environment (e.g., other medical device or equipment, electromagnetic noise from communication devices, broadcast sources, hubs, etc.), electromagnetic noise produced by the MRI system itself and/or electromagnetic noise couple to and introduced by the patient as is the case for sensor 350. The one or more auxiliary sensors then provide an indication, measure or other quantification of the detected electromagnetic noise to noise reduction system 330 to facilitate noise compensation (e.g., reduction or elimination). Noise reduction system 330 may be of any suitable type including, for example, the type described herein including with reference to FIG. 16. For example, noise reduction system 330 may be similar to any of the noise reduction systems described in U.S. Pat. No. 9,625,543 ('543 patent), titled "Noise Suppression Methods and Apparatus" issued Apr. 18, 2017. However, noise reduction system 330 may further include a channel corresponding to electromagnetic noise characterized by sensor 350.

Power system 310 may include one or more power components configured to provide power to operate MRI system 300. For example, power system 310 may include one or more power supplies, one or more power converters, power distribution and management controller, one or more amplifiers, one or more transmit/receive switches, and/or one or more thermal management components. Components of power system 310 are described further herein including with reference to FIG. 1.

Electromagnetic shielding 340 may include one or more electrically conductive surfaces at least partially surrounding an imaging region of MRI system 300. As used herein, the term electromagnetic shielding refers to conductive or magnetic material configured to attenuate electromagnetic noise at the operational frequency range of the MRI system and positioned or arranged to shield a space, object and/or component of interest. In the context of an MRI system, electromagnetic shielding may be used to shield the imaging region (e.g., the field of view) of the MRI system. For example, electromagnetic shielding 340 may be included in the form of moveable slides that can be opened and closed and positioned in a variety of configurations. In each of the variety of configurations, electromagnetic shielding 340 may be arranged or positioned to attenuate frequencies at least within the operational frequency range of MRI system 300 for at least a portion of the imaging region. Further aspects of electromagnetic shielding for use in low-field MRI systems, such as electromagnetic shielding 340 of MRI system 300, are described in U.S. Pat. Application Publication No. 2018/0164390, titled "Electromagnetic Shielding For Magnetic Resonance Imaging Methods and Apparatus", which is herein incorporated by reference in its entirety.

Figure 4:
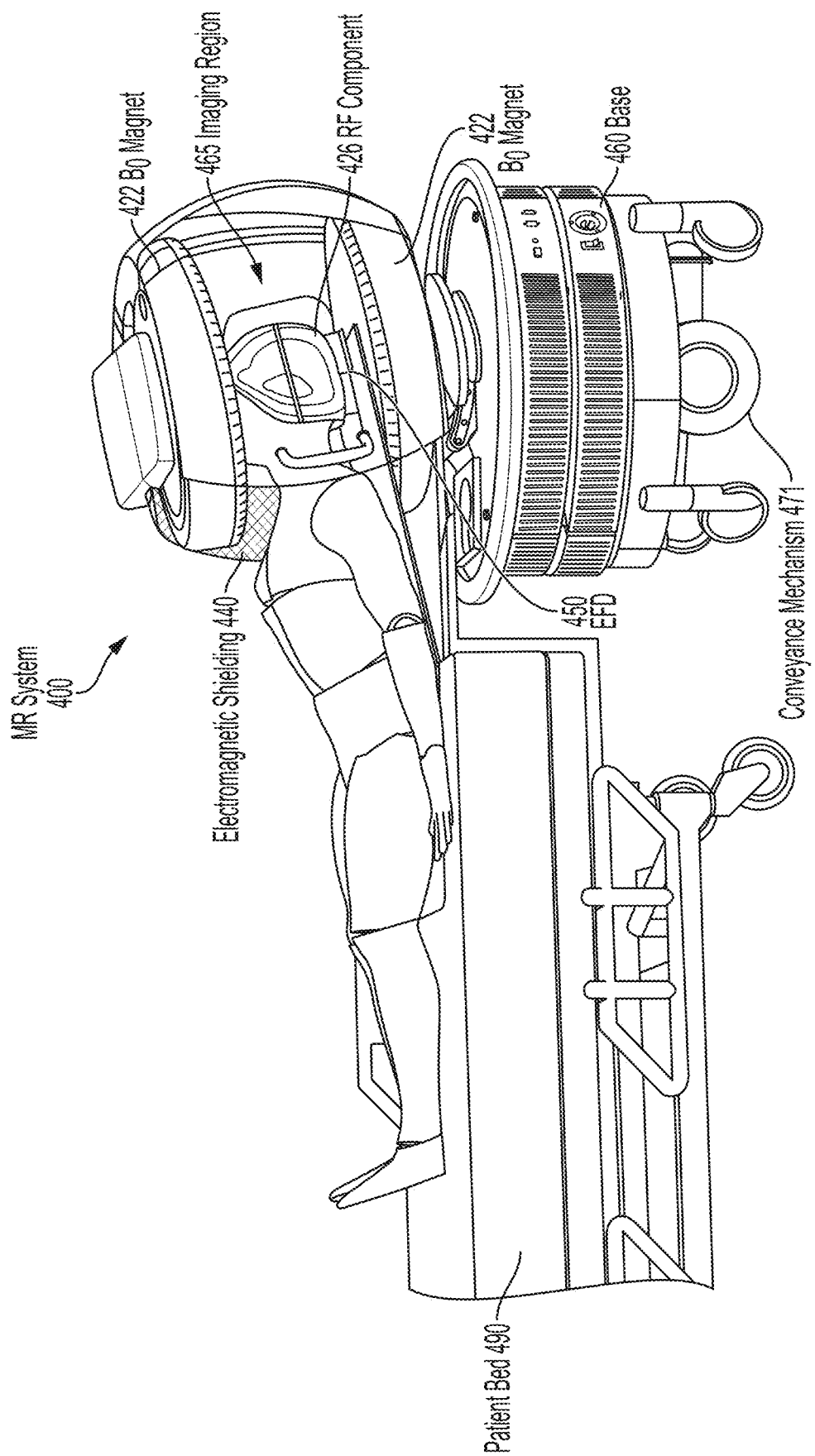
FIG. 4 is a drawing of an illustrative MRI system configured to detect electromagnetic noise conducted by a patient, in accordance with some embodiments of the technology described herein.

FIG. 4 is a drawing of illustrative MRI system 400 and components thereof. MRI system 400 is configured to detect and suppress electromagnetic noise conducted by a patient, in accordance with some embodiments of the technology described herein. In FIG. 4, MRI system 400 may include any one or combination of the components described in connection with FIGS. 1-3, such as a power system, for example, located within base 460, a magnetics system including $B_0$ magnet 422 and RF component 426, electromagnetic shielding 440, electric field detector (EFD) 450 (e.g., a sensor similar or the same as any one or combination of sensors described above in connection with FIGS. 2 and 3 and/or described in further detail below), and a noise reduction system (e.g., a noise reduction system implemented as part of one or more controllers located within base 460 or otherwise provided in connection with MRI system 400).

Exemplary MRI system 400 illustrated in FIG. 4 may be portable. For instance, MRI system 400 includes conveyance mechanism 471 which facilitates transporting the system, such as to a location where MRI is needed. The portability of MRI system 400 enables point-of-care imaging of patients, allowing for imaging without needing to transport the patient to a specialized MRI department (e.g., the MRI system 400 may be transported to the patient) or with relatively limited transportation of the patient (e.g., patient bed 490 may be transported to a locally deployed or nearby MRI system, such as an MRI installment in the same department or room as the patient (e.g., in an emergency room, operating room, ICU, etc.), or an MRI installment to which the patient may be transported without having to move the patient from the bed). As such, MRI system 400 may be used to image patients for which MRI would conventionally be unavailable, such as patients who are immobilized, suffering from painful conditions that restrict movement and/or conditions that preclude them from being transported to dedicated MRI spaces or facilities.

It should be appreciated that MRI system 400 may also be used to image patients with full mobility, providing convenient point-of-care imaging with increased availability relative to conventional fixed MRI installments in a dedicated facility or department. In some embodiments, conveyance mechanism 471 includes a motor coupled to drive wheels. Additional wheels not coupled to the motor may be provided for improved stability. Thus, conveyance mechanism 471 may provide motorized assistance in transporting MRI system 400 to desired locations. In some embodiments, motorized assistance may be controlled using a controller (e.g., a joystick or other controller that can be manipulated by a person) to guide the portable MRI system during transportation to desired locations.

MRI system 400 may further comprise electromagnetic shielding 440, which in the embodiment illustrated in FIG. 4 may include moveable shields that can be opened or closed, for example to facilitate positioning the patient in the imaging region of MRI system 400. Components of the magnetics system may be positioned above and/or below the imaging region and configured to perform MR imaging of the patient. For example, $B_0$ magnets 422 are positioned above and below the patient and may generate a $B_0$ magnetic field for imaging region 465. Other components of the magnetics system such as gradient coils, RF coils and shim coils may also be positioned above and/or below the imaging region to perform MR imaging of the patient. For example, RF component is shown within the imaging region for receiving and imaging the patient's head.

MRI system 400 is configured to image patients in environments that are not fully shielded, in contrast to conventional MRI systems that operate is specially shielded and dedicated MRI spaces (i.e., in specially shielded rooms dedicated for MRI). As such, MRI system 400 is configured to operate in environments that may have significantly more electromagnetic noise than fully shielded environments in which typical MRI systems are employed. Although electromagnetic shielding 440 may be positioned about the imaging region to detect and suppress at least some electromagnetic noise in the vicinity of the system, the inventors recognized that the patient may conduct electromagnetic noise from the surrounding environment into the imaging region, bypassing electromagnetic shielding 440 and introducing the electromagnetic noise into imaging region 465 of the MRI system.

To address patient introduction of electromagnetic noise, EFD 450 illustrated in FIG. 4 may be used to detect electromagnetic noise introduced by the patient so that it can be suppressed and/or compensated for, as described in further detail below. In some embodiments, EFD 450 may include one or more electrical conductors positioned to detect electromagnetic noise introduced by the patient. For example, EFD 450 may include electrical conductors configured for capacitively coupling to the patient to detect electromagnetic noise conducted by the patient to facilitate suppression of and/or compensation for the detected electromagnetic noise, examples of which are described in further detail below. It should be appreciated that an EFD configured to detect electromagnetic energy introduced by the patient may be used in connection with any type of RF component configured for any anatomical portion of the patient's body, as the aspects are not limited in this respect.

FIG. 4 illustrates MRI system 400 employed to image a patient's head. As such, EFD 450 is provided proximate radio frequency (RF) component 426 adapted to accommodate the patient's head and comprising one or more transmit/receive coils configured to produce excitation pulse sequences and detect magnetic resonance signals emitted by the patient in response to the transmitted pulse sequences. However, it should be appreciated that an EFD 450 may be configured to operate in conjunction with any type of RF component, including for example an RF component configured to accommodate and image a leg, arm, foot, body, etc. For example, EFD 450 may be configured to detect electromagnetic noise by being provided proximate to any of the exemplary RF components illustrated in U.S. application Ser. No. 16/516,373, filed on Jul. 19, 2019 and titled "Methods and Apparatus for Patient Positioning in Magnetic Resonance Imaging," which is herein incorporated by reference in its entirety.

Figure 5A:
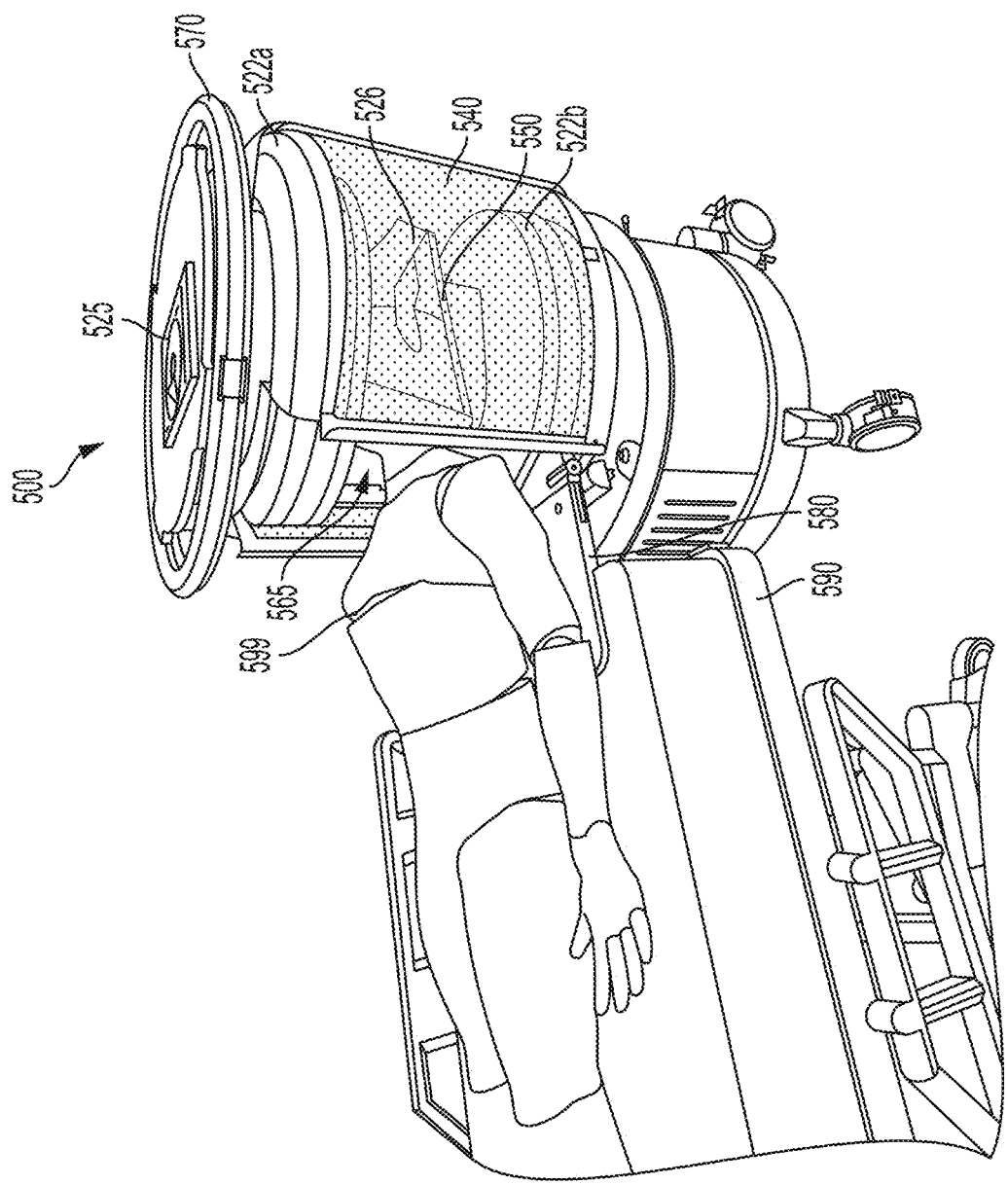
FIG. 5A is a drawing of an alternative illustrative MRI system configured to detect electromagnetic noise conducted by a patient, in accordance with some embodiments of the technology described herein.

FIG. 5A illustrates an exemplary point-of-care MRI system 500 employed to image a patient's head and configured with a noise reduction system for suppressing and/or compensating for noise introduced by a patient, in accordance with some embodiments. MRI system 500 may include a number of features similar to MRI system 400, including, for example electromagnetic shields 540 that can be moved about imaging region 565 formed by $B_0$ magnets 522a and 522b configured in a bi-planar arrangement. MRI system 500 further comprises a bridge 580 that can be folded down to overlap hospital bed 590 to provide support to patient 599 during positioning and imaging of the patient. EFD 550 is provided proximate radio frequency (RF) component 536 adapted to accommodate the patient's head and comprising one or more transmit/receive coils configured to produce excitation pulse sequences and detect magnetic resonance signals emitted by the patient in response. MRI system 500 further comprises a guard 570 that may be deployed to demarcate the physical boundary within which the magnetic field is above a specified field strength to provide a visual signal when the MRI system is being moved to a different location, examples of which are described in U.S. application Ser. No. 16/389,004, titled "Deployable Guard for Portable Magnetic Resonance Imaging Device," and filed on Apr. 19, 2019, which is herein incorporated by reference in its entirety.

Figure 5B:
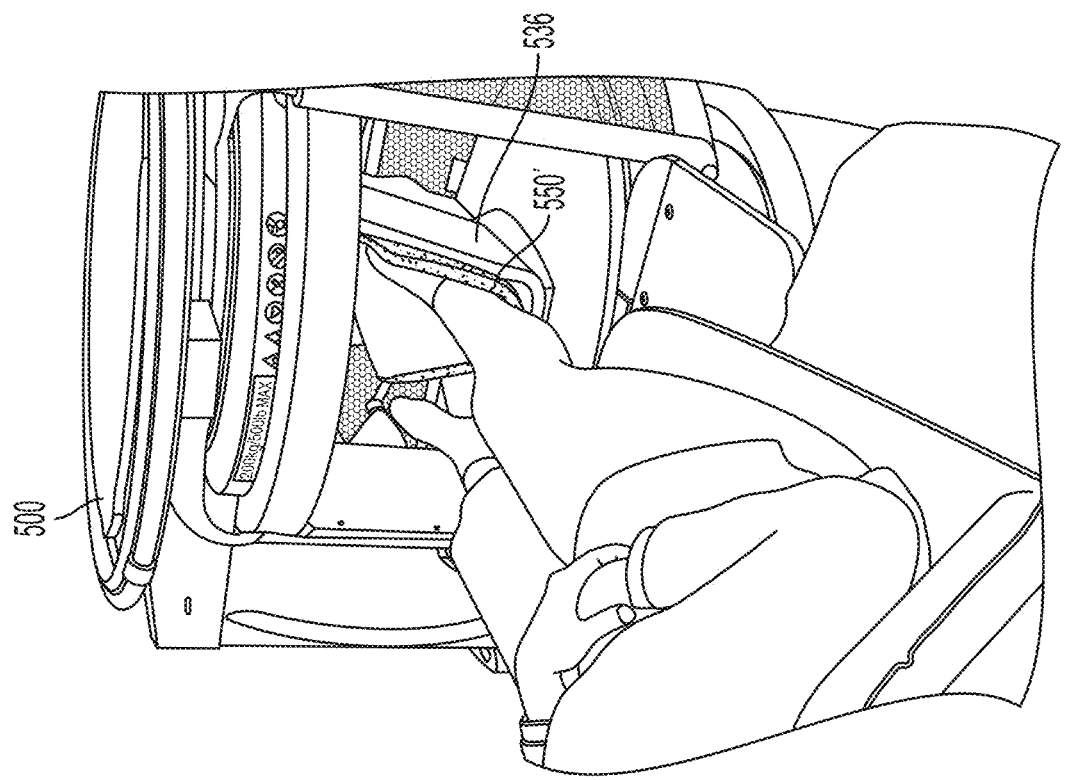
FIG. 5B is a drawing of a further alternative illustrative MRI system configured to detect electromagnetic noise conducted by a patient, in accordance with some embodiments of the technology described herein.

EFD 550 detects electromagnetic noise introduced by patient 599 as a result of electromagnetic radiation in the environment coupling to the patient and being conducted into imaging region 565 as noise (e.g., EFD 550 may comprise any of the capacitive and conductive coupling mechanisms and arrangements described above and in further detail below). MRI system 500 further includes a mobile or portable device 525 (e.g., a notepad, smartphone, etc.) configured to communicate with one or more controllers of the MRI system to initiate an imaging procedure and acquire one or more MRI images. FIG. 5B illustrates MRI system 500 in use with RF component 536 configured to accommodate a foot and transmit excitation pulse sequences and detect resulting MR signals. As such, exemplary EFD 550' may be positioned proximate (e.g., on, in or near) RF component 536 so that when the foot is positioned for imaging, EFD 550' is positioned to detect electromagnetic noise introduce into the system by the patient. Example arrangements and geometries for an EFD are described in further detail below.

FIGS. 4 and 5A illustrate the use of an EFD to detect electromagnetic interference introduced by a patient in connection with an RF component configured to image a patient's head, and FIG. 5B illustrates the use of an EFD to detect electromagnetic interference introduced by a patient in connection with an RF component configured to image a patient's foot. However, use of an EFD is not limited for use with any particular type of RF component or any particular imaging protocol. Techniques for detecting electromagnetic interference introduced by the patient may be used in connection with any type of RF component including, but not limited to, RF components configured to image a patient's head, foot, leg(s), arm(s), hand(s), torso, full body, etc., as the aspects are not limited in this respect. For example, electrical conductors configured to capacitively and/or conductively coupled to a patient may be positioned on or within any type of RF component (e.g., on or within a housing of an RF component configured to accommodate any anatomy or portion of anatomy of the patient), allowing for the techniques described herein to be employed for any type of MRI operation.

Figure 6:
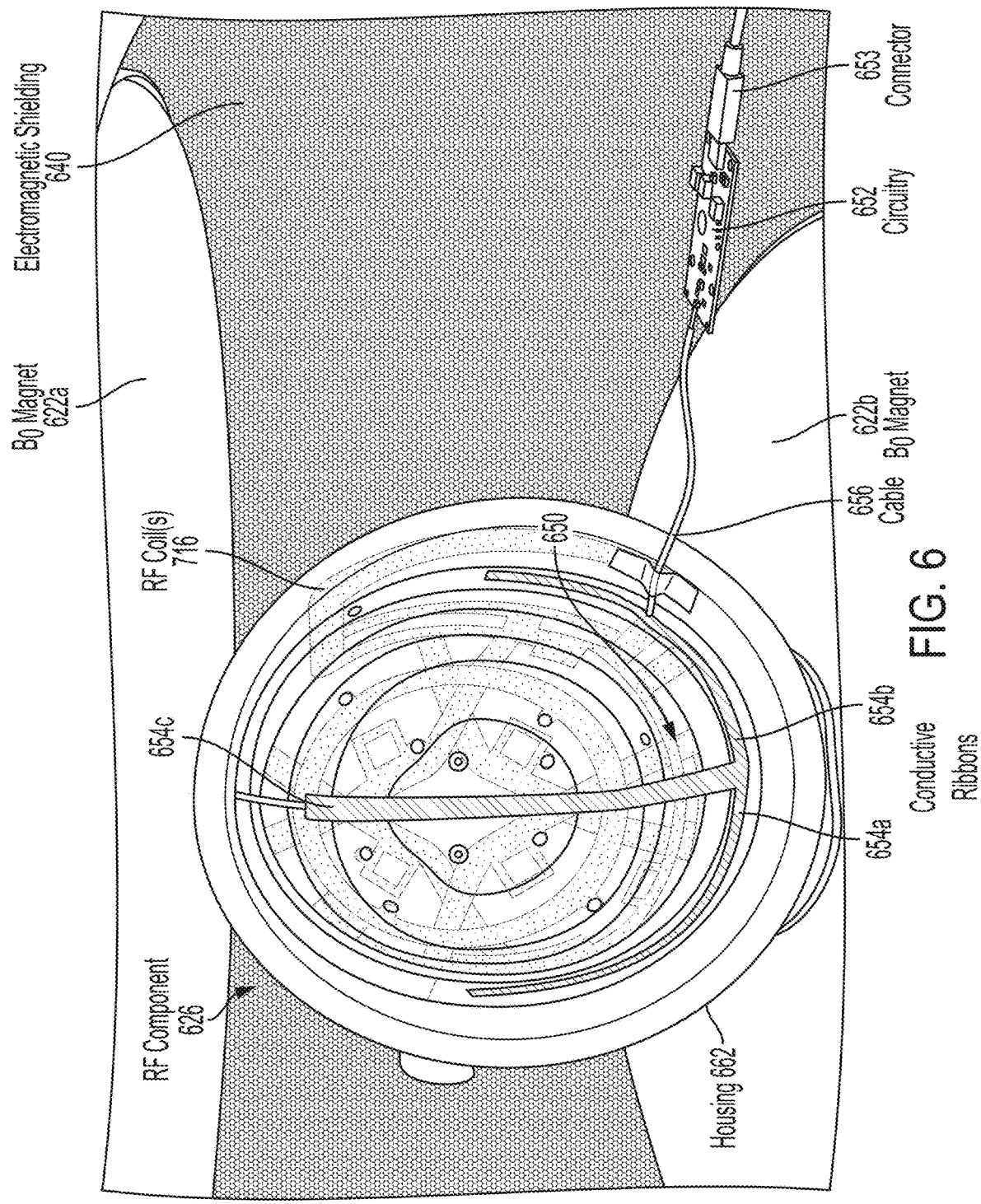
FIG. 6 is a drawing of an illustrative electric field detector (EFD) for an MRI system configured to detect electromagnetic noise conducted by a patient, in accordance with some embodiments of the technology described herein.

FIG. 6 illustrates a radio frequency (RF) component 626 (e.g., a helmet) comprising a housing 662 adapted to accommodate a patient's head and that supports RF coil(s) 716, for example, one or more transmit coils and/or one or more receive coils. As shown in the exemplary embodiment illustrated in FIG. 6, EFD 650 comprises conductive ribbons 654a-654c as electrical conductors, with conductive ribbons 654a-654b positioned within capacitive coupling range of a patient's head when the patient's head is positioned within housing 662 during imaging. For instance, conductive ribbons 654a-654c may be attached to housing 662 of RF component 626 such that, when the patient's head is positioned within housing 662, conductive ribbons 654a-654c capacitively couple to the patient (i.e., by being in close proximity to the patient's head). Thus, EFD 650 is configured to detect electromagnetic radiation introduced into MRI system 500 by the patient as noise from the environment via the coupling between conductive ribbons 654a-654c, for example, as capacitive coupling wherein conductors of the conductive ribbons and the patient's head function as terminals of a capacitor.

In the exemplary embodiment illustrated in FIG. 6, conductive ribbons 654a-654b may be attached or affixed (e.g., adhesively attached) to an inner surface of housing 662. Using the exemplary geometry illustrated in FIG. 6, conductive ribbons 654a-654c are configured to capacitively couple electromagnetic radiation having different (e.g., orthogonal) electrical polarities. For example, conductive ribbons 654a-654b are provided about a portion of the circumference of housing 662, whereas conductive ribbon 654c is provided generally in a perpendicular direction relative to circumferentially positioned conductive ribbons 654a-654b. As a result, EFD 650 is configured to couple with electromagnetic radiation introduced by the patient at different electrical polarities so as to detect electromagnetic noise more comprehensively.

It should be appreciated that the configuration of conductors illustrated in FIG. 6 is exemplary and numerous other configurations and geometries may be employed, as the aspects are not limited in this respect. For example, while the exemplary EFD 650 illustrated in FIG. 6 employs three conductive ribbons 654a-654c, any number of conductors in any configuration and/or geometry may be used. In particular, a single conductor may be used to detect electromagnetic radiation introduced by the patient or multiple conductors may be used in different configurations, as illustrated in FIGS. 8A-8C described in further detail below. In embodiments that employ a plurality of conductors, the respective conductors may be electrically connected to each other or may be electrically separate and/or isolated from each other. In particular, the conductors of an EFD may be electrically connected to each other (e.g., as shown by conductive ribbons 654a-654c of EFD 650 in FIG. 6) or the conductors of an EFD may each be electrically separated from the other conductors of the EFD, as described in further detail below in connection with the exemplary embodiments illustrated in FIGS. 7A and 7B. In some embodiments, conductors of an EFD may include electromagnetic shielding, as described in further detail in connection with the exemplary embodiments illustrated in FIGS. 9C-9D. Additional examples of electrical conductors that may be included in an EFD, alternatively or in addition to conductive ribbons, are described further herein including with reference to FIGS. 8A-8D and 11A-14.

When conductive ribbons 654a-654c capacitively couple to the patient, electromagnetic radiation conducted by the patient induces current in conductors of conductive ribbons 654a-654c indicative of the electromagnetic radiation, which can be used as a measure of the electromagnetic noise introduced into the MRI system by the patient. To capture the detected electromagnetic noise (e.g., currents induced in conductive ribbons 654a-654c in the embodiment illustrated in FIG. 6), EFD 650 includes a cable 656 connected to conductive ribbons 654a-654c to receive current induced in conductive ribbons 654a-654c indicative of electromagnetic radiation and transmit this detected electromagnetic noise to circuitry 652, which may include any circuitry needed to process the detected electromagnetic noise so that it can be suppressed and/or compensated for by a noise reduction component of the MRI system, including, for example, any needed or desired signal conversion (e.g., analog to digital conversion), any needed or desired amplification, any needed or desired filtering, etc. In the embodiment illustrated in FIG. 6, circuitry 652 comprises a printed circuit board that processes the detected electromagnetic noise from conductive ribbons 654a-654c (e.g., induced currents in the conductors) and provides the processed electromagnetic noise to a noise reduction system via connector 653. It should be appreciated that electromagnetic noise detected by an EFD may be captured and conveyed using other techniques, as the aspects are not limited in this respect.

Figure 7B:
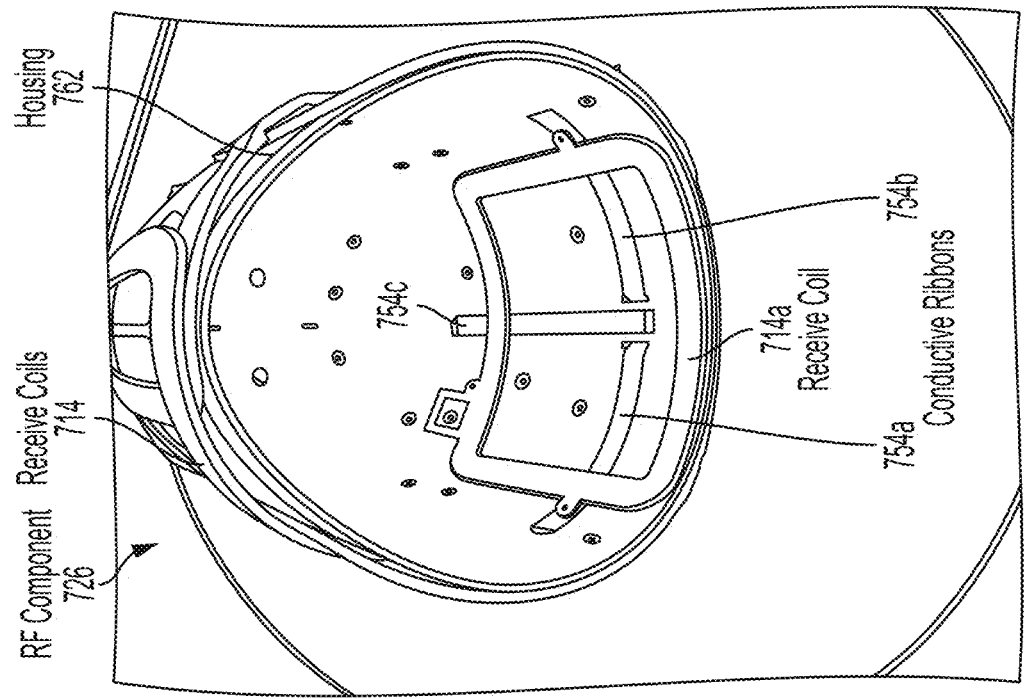
FIGS. 7A and 7B are drawings of illustrative components of an EFD for an MRI system configured to detect electromagnetic noise conducted by a patient, in accordance with some embodiments of the technology described herein.
Figure 7A:
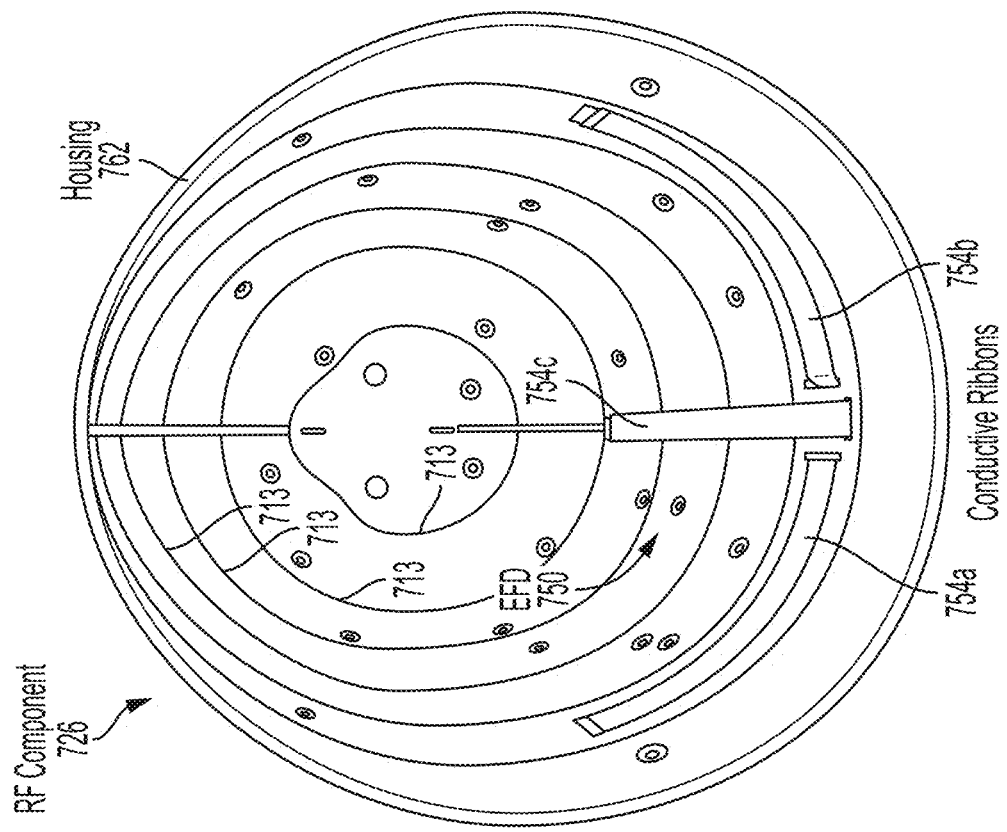
Figure 8A:
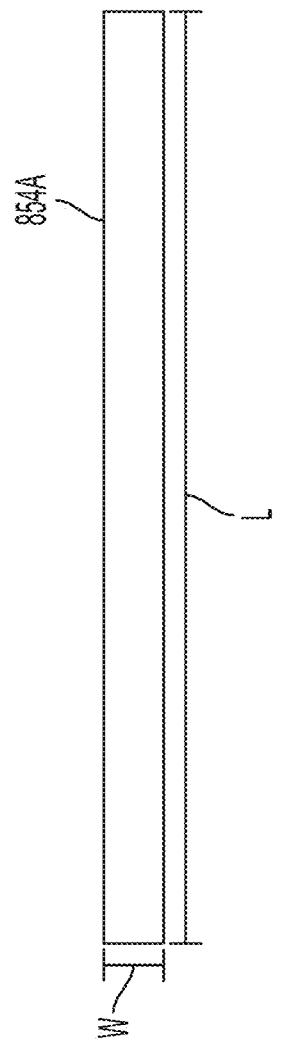
FIGS. 8A-8D illustrate exemplary geometries and arrangement for conductors of an EFD, in accordance with some embodiments.
Figure 8B:
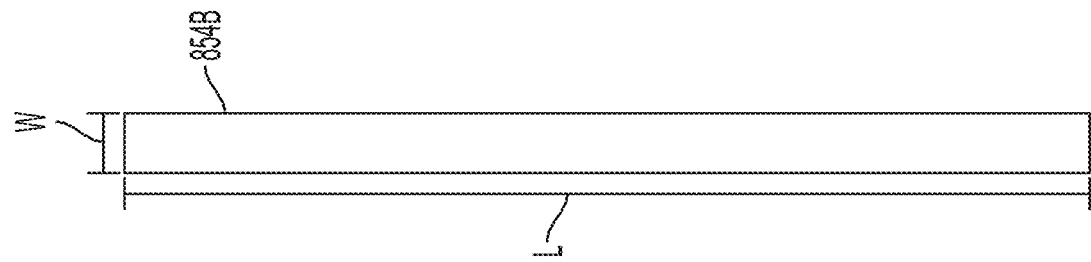

FIGS. 7A and 7B illustrate an embodiment of an EFD configured to detect electromagnetic energy introduced by a patient from the environment, in accordance with some embodiments. Exemplary EFD 750 comprises three conductive ribbons 754a, 754b and 754c as conductors of the EFD arranged within housing 762 of RF component 726 configured to accommodate a patient's head during MRI. In FIGS. 7A and 7B, RF component 726 is illustrated at different stages of manufacture to show one exemplary arrangement of an EFD. In the embodiment illustrated in FIG. 7A, conductive ribbons 754a-754c each include conductive strips of material and are attached, affixed or otherwise positioned within housing 762 so as to capacitively couple to a patient when the patient's head is positioned within housing 762. Contours in which one or more transmit coils are positioned are shown on housing 762, of which several examples contours are labeled as contours 713. The configuration of contours may be determined using techniques described, for example, in Patent Application Publication US 2016/0334479 ('479 Publication), entitled "Radio Frequency Coil Methods and Apparatus," which is herein incorporated by reference in its entirety. Thus, RF component 726 may include any of the exemplary RF transmit/receive coils described in the '479 Publication, or may include any suitable type of transmit/receive coils.

According to some embodiments, circuitry connected conductive ribbon 754a-754c (e.g., amplification circuitry, conversion circuitry, etc.) is configured to electrically isolate the conductors during transmission of RF pulses produced by the transmit coils to avoid detecting RF transmissions and/or to protect sensitive components of the sensor (e.g., sensitive electronics of the EFD). For example, one or more PIN diodes or gallium nitride field effect transistors (GaN-FETs) may be used to isolate the conductors during RF transmission in much the same way that receive coils are isolated during periods in which transmit coils are producing RF pulses. FIG. 7B illustrates RF component 726 with receive coils 714 positioned about housing 762. In the exemplary embodiment illustrated in FIG. 7B, RF component 726 comprises a plurality of overlapping receive coils 714 (e.g., an array of eight receive coils) configured to detect magnetic resonance signals emitted from the patient in response to RF pulses produced by the transmit coil(s) of RF component 726. An example of a receive coil 714a is shown positioned within housing 762 to illustrate the relative arrangement between the conductors of EFD 750 and receive coils 714 of exemplary RF component 726, not as an example of coil placement in the illustrated embodiment, though one or more receive coils could be positioned on the interior of the housing, as the aspects are not limited in this respect.

In exemplary embodiments illustrated above, an EFD is formed using a plurality of conductors, either electrically connected (e.g., by providing conductors in direct contact with one another), indirectly connected via a connection circuitry, or electrically isolated from each other. FIGS. 8A-D illustrate embodiments of EFDs formed using a single conductor. For example, FIG. 8A illustrates an embodiment using a single horizontally oriented conductor 854A that may, for example, be positioned circumferentially within an RF component adapted to accommodate a patient's head and/or about the perimeter or aligned with the podal axis of an RF component adapted to accommodate a patient's foot. FIG. 8B illustrates an embodiment using a single vertically oriented conductor 854B that may, for example, be positioned longitudinally within an RF component adapted to accommodate a patient's head and/or configured to accommodate a patient's foot. Some of the embodiments described herein conductors are formed by conductive strips, which refers generally to conductors that have one dimension (e.g., a length L) that is substantially greater than another dimension (e.g., a width W). For example, a strip will have a first dimension that is at least 3 times length of a second dimension. More typically, a strip will have a first dimension that is at least 4 times a second dimension, and more usually at least 5 times a second dimension (e.g., exemplary conductive strips may have a length that is 5, 6, 7, 8, 9, 10 or more times its width). Such conductors may be formed from conductive tape, conductive sheets, flexible PCBs, etc.

Figure 8D:
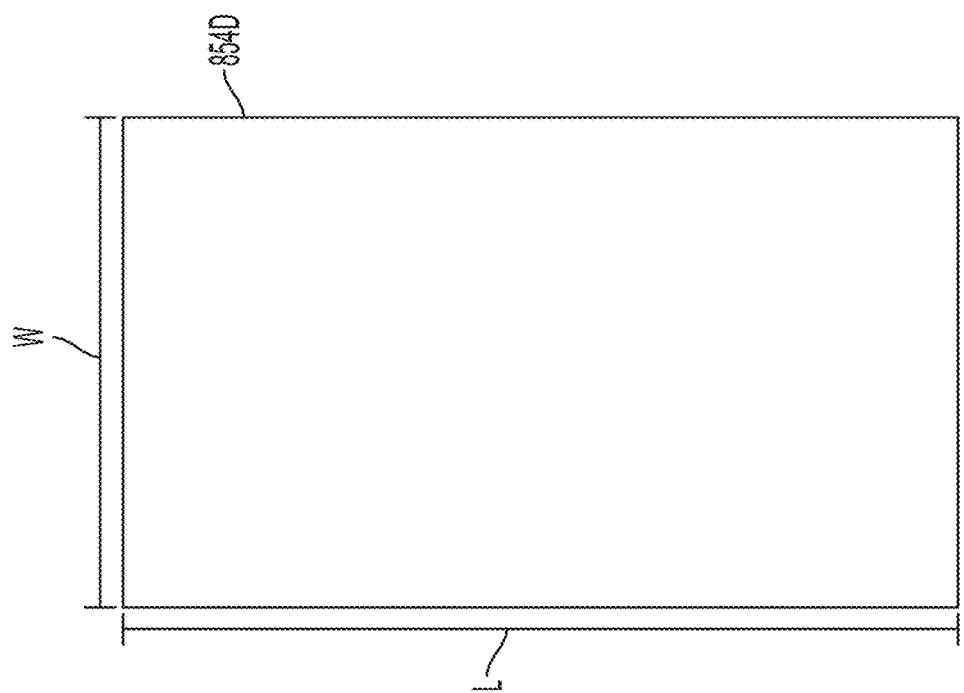
Figure 8C:
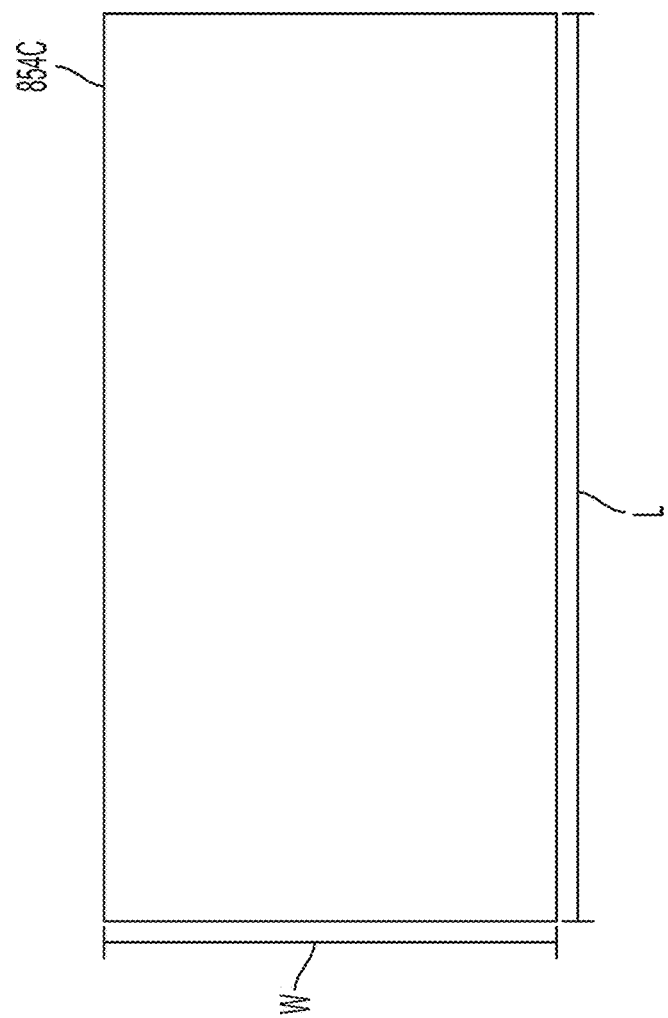

It should be appreciated, however, that EFDs may be formed from geometries other than conductive strips. For example, FIGS. 8C and 8D illustrate rectangular shaped conductors 854C and 854D, respectively, that can be provided on, in, or proximate to a housing of an RF component to detect electromagnetic radiation that couples to the patient from the environment and is introduced by the patient as electromagnetic noise. Exemplary conductors 8C and 8D, for example, may take the form of a conductive pad, plate or sheet positioned so as to couple to a patient when the patient is positioned for imaging. It should be appreciated that other geometries are possible, including circular or spiral geometries or any other configuration capable of detecting electromagnetic noise that couples to the patient from the environment, as the aspects are not limited in this respect. Moreover, an EFD may be formed using different combinations of different conductor geometries to detect electromagnetic noise for suppression and/or compensation, as described in further detail below.

Figure 9B:
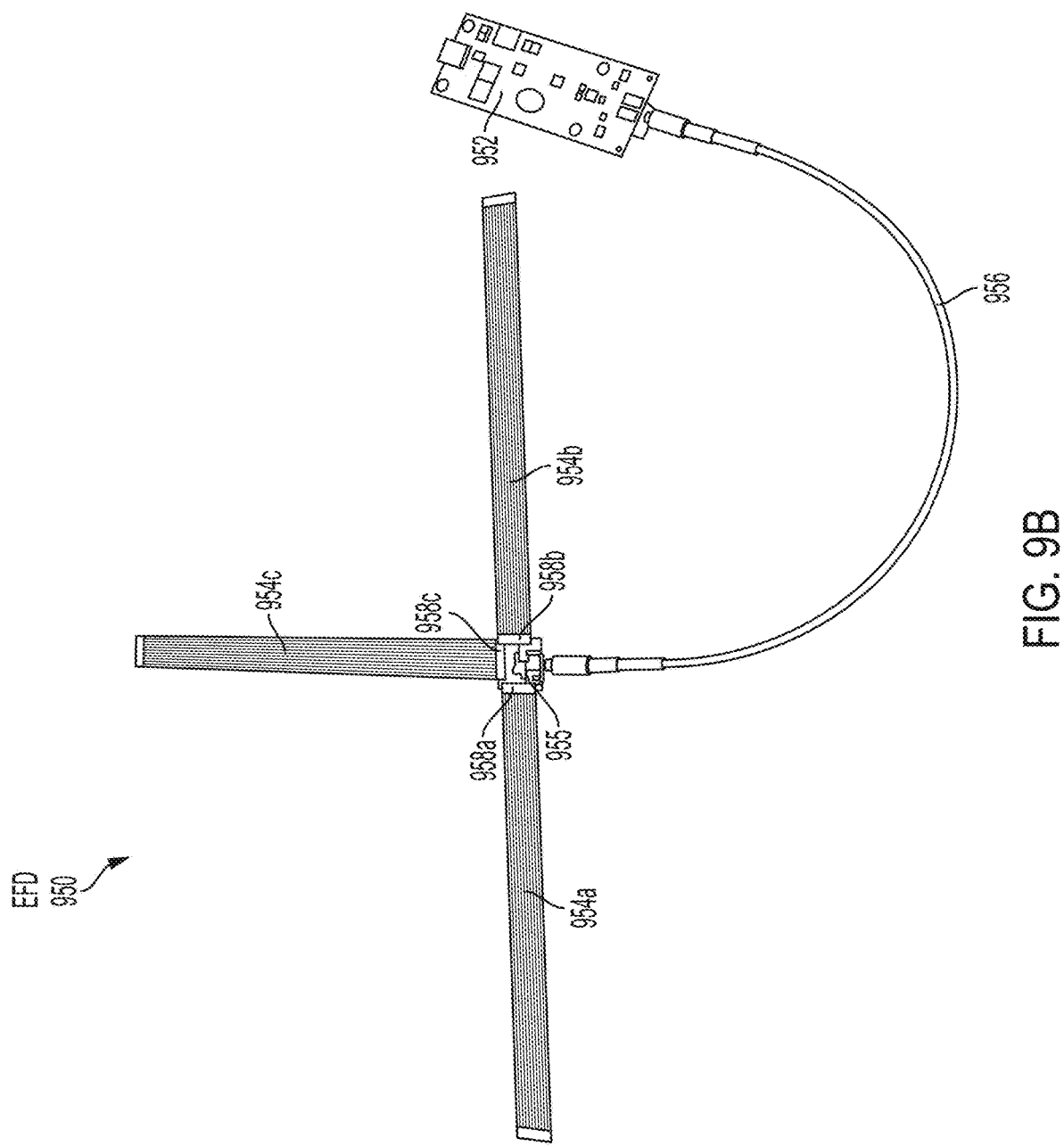
FIG. 9B is a drawing of an illustrative EFD comprising a plurality of conductive ribbons for an MRI system configured to detect electromagnetic noise conducted by a patient, in accordance with some embodiments of the technology described herein.

Conductors used to couple to a patient to detect electromagnetic noise introduced by the patient may be constructed in any suitable manner. For example, conductors may be formed from a sheet of conductive material manufactured according to a desired geometry (e.g., as a rectangular or circular conductor or as a conductive strip) or from conductive tape or the like. According to some embodiments, one or more conductors forming an EFD for a noise reduction system is comprised of printed circuit board (PCB) material, for example, a flexible PCB strip or ribbon material. FIG. 9A illustrates a flexible PCB suitable for use as a conductor for an EFD, in accordance with some embodiments. Conductive ribbon 954 is formed from a strip of flexible PCB material comprising a plurality of individual conductors, each terminating at a respective connector that, together provide electrical connector 958, which allows ribbon 954 to be coupled to the next level of interconnection (e.g., electrical connector 955 illustrated in FIG. 9B described below) so that the electrical signals indicative of electromagnetic radiation conducted by the patient (detected electromagnetic noise) can be provided to the noise reduction component of the MRI system. In some embodiments, a layer of the flexible PCB (e.g., a back side of the illustrated flexible PCB, not shown) may include a ground plane for coupling to the ground plane of the next level of interconnection. The individual conductors of ribbon 954 may be formed in any suitable way, for example, using any suitable technique for fabricating conductive traces on a PCB. In accordance with various embodiments, flexible PCBs may be formed using a plastic substrate such as polyimide, polyether ether ketone (PEEK), and/or transparent conductive polyester film. A flexible PCB conductor may be used as a single conductor or multiple flexible PCBs may be arranged in a desired geometry to provide an EFD.

FIG. 9B illustrates an EFD 950 formed from three flexible PCB ribbons 954a, 954b and 954c, each with their respective connectors 958a, 958b and 958c connected to a connector interface 955 which, in turn, is configured to couple to cable 956. According to some embodiments, connector interface 955 is a printed circuit board, but the connector interface 955 may be any suitable electronic connector configured to electrically couple to connectors of the conductors (e.g., connectors 958 of conductive ribbons 954*a-c* in FIG. 9B). In the illustrative embodiment illustrated in FIG. 9B, cable 956 is a coaxial cable which provides desirable transmission characteristics and a measure of shielding from other electrical and/or electromagnetic signals or noise produced by the MRI system or present in the environment. However, cable 956 may be any suitable connection and/or transmission medium capable of providing high frequency (e.g., the operating frequency of the MRI system) electrical signals from the conductors to further circuitry of the EFD 950 and/or noise reduction component. For example, in the embodiment illustrated in FIG. 9B, cable 956 receives the electrical signals from conductors 954*a-c* indicative of electromagnetic noise via connector interface 958 and transmits the signals (detected electromagnetic noise) to circuitry 952, which may amplify the signals for further processing and/or prepare the signals to facilitate suppression and/or compensation of the electromagnetic noise characterized by the electrical signals received from the conductors. In the embodiment illustrated in FIG. 9B, electrical connector interface 955 receives electrical signals from each of conductors 954*a-c* and provides the combined electrical signals to cable 956 for transmission to downstream circuitry and processing. According to some embodiments, electrical signals from the different conductors of the EFD may be received and/or transmitted separately to downstream circuitry, making it possible to evaluate the electromagnetic noise detected by each conductor independently of electromagnetic noise detected by other conductors of the EFD. Thus, circuitry 952 may be configured to receive, convert, filter, amplify and/or otherwise process combined signals from conductors 954*a-c* or may be configured to receive, convert, filter, amplify and/or otherwise process signals from conductors 954*a-c* individually (e.g., independent of one another), as the aspects are not limited in this respect.

FIG. 9C is a drawing of conductive ribbon 954 and electromagnetic (EM) shielding 960, which may be disposed between conductive ribbon 954 and one or more components of an MRI system, in accordance with some embodiments. The inventors recognized that it is desirable to position an EFD including conductive ribbon 954 close to the RF receive coil(s) of an MRI system so that electromagnetic noise detected by the EFD is similar to the noise present in MR signals emitted by the patient and detected by the RF receive coil(s), which facilitates suppressing the noise from the detected MR signals based on the noise detected by the EFD. In some cases, however, the EFD may be positioned close enough to the RF receive coil(s) that the EFD detects MR signals (e.g., by electrically coupling to the RF receive coil(s)), which can cause portions of the MR signals to be mischaracterized by the MRI system as noise, resulting in the MRI system suppressing portions of the MR signals and degrading the signal to noise ratio of the MRI system.

In some embodiments, this problem is addressed by including electromagnetic shielding for conductors of the EFD. For example, by configuring the EFD such that the electromagnetic shielding is positioned between a component of the MRI system (e.g., the RF receive coil) and the conductors of the EFD, the electromagnetic shielding may be configured to block the EFD from detecting MR signals emitted by the patient that are also detected by the MRI system component, thereby preventing the detected MR signals from being mischaracterized as noise. For example, the electromagnetic shielding may be configured to prevent the EFD from electrically coupling to the RF receive coil(s) of the MRI system in the operating frequency range of the MRI system, as described herein.

In some embodiments, electromagnetic shielding may be provided for conductive ribbons of an EFD to shield the conductive ribbons from at least some electromagnetic radiation incident on the conductive ribbons from at least one direction. In some embodiments, the electromagnetic shielding may include a plurality of conductive strips. In FIG. 9C, for example, electromagnetic shielding 960 is disposed on one side of conductive ribbon 954 and includes a plurality of interdigitated fingers 962 elongated in a direction perpendicular to the direction of elongation of conductive ribbon 954 and spaced from one another in the direction of elongation of conductive ribbon 954. In this example, electromagnetic shielding 960 is configured to shield conductive ribbon 954 from electromagnetic radiation incident on conductive ribbon 954 from the side of conductive ribbon 954 on which electromagnetic shielding 960 is disposed. In some embodiments, interdigitated fingers 962 may be configured to shield electromagnetic radiation in the operating frequency range of the MRI system. For example, interdigitated fingers 962 may be spaced from one another by a distance that is electrically small in the operating frequency range of the MRI system, such that electromagnetic shielding 960 acts like an uninterrupted conductive sheet for electromagnetic radiation in the operating frequency range of the MRI system. In some embodiments, interdigitated fingers 962 may reduce or minimize coupling between the RF coil(s) of the MRI system and electromagnetic shielding 960. For example, interdigitated fingers 962 may reduce or minimize eddy currents from coupling to the RF coil(s) that would otherwise introduce losses to MRI signals received by the RF coil(s), while also reducing or eliminating coupling between the RF coil(s) and the EFD.

In some embodiments, electromagnetic shielding 960 may be disposed on a same flexible PCB as the conductors of conductive ribbon 954, such that conductive ribbon 954 includes electromagnetic shielding 960 on a separate layer from the conductors. In some embodiments, electromagnetic shielding 960 may be disposed on a separate flexible PCB from conductive ribbon 954. For example, conductive ribbon 954 and the flexible PCB including electromagnetic shielding 960 may be disposed next to and/or attached to one another.

In some embodiments, an EFD including conductive ribbon 954 and electromagnetic shielding 960 may be positioned next to an RF component of an MRI system. For example, referring back to FIGS. 7A-7B, electromagnetic shielding 960 may be disposed between conductive ribbon 954 and receive coils 714 of RF component 726. In this example, housing 762 of RF component 726 may be disposed between electromagnetic shielding 960 and receive coils 714, with electromagnetic shielding 960' disposed on an interior surface of housing 762 and receive coils 714 disposed on an exterior surface of housing 762. When a portion of a patient's body is inserted into RF component 726, conductive ribbon 954 may electrically couple noise from the patient to a noise reduction system of the MRI system. During imaging, MR signals emitted by the patient may be detected by receive coils 714, with electromagnetic shielding 960 preventing conductive ribbon 954 from coupling to receive coils 714 and detecting the MR signals received by receive coils 714.

In some embodiments, it may be desirable to position electromagnetic shielding 960 on one side of conductive ribbon 954, such as shown in FIG. 9C, such that electromagnetic shielding 960 is configured to block electromagnetic radiation from the MRI system component(s) disposed on an opposite side of electromagnetic shielding 960 from conductive ribbon 954 and also configured to detect electromagnetic noise from the patient that is incident on conductive ribbon 954 from other directions. It should be appreciated, however, that electromagnetic shielding 960 may be disposed on any side or sides of conductive ribbon 954, in accordance with various embodiments.

While electromagnetic shielding 960 is shown for conductive ribbon 954, it should be appreciated that electromagnetic shielding may be provided for other types of EFDs and/or sensors described herein, such as for a conductive patch or pad configured for capacitively coupling to a patient.

Figure 9D:
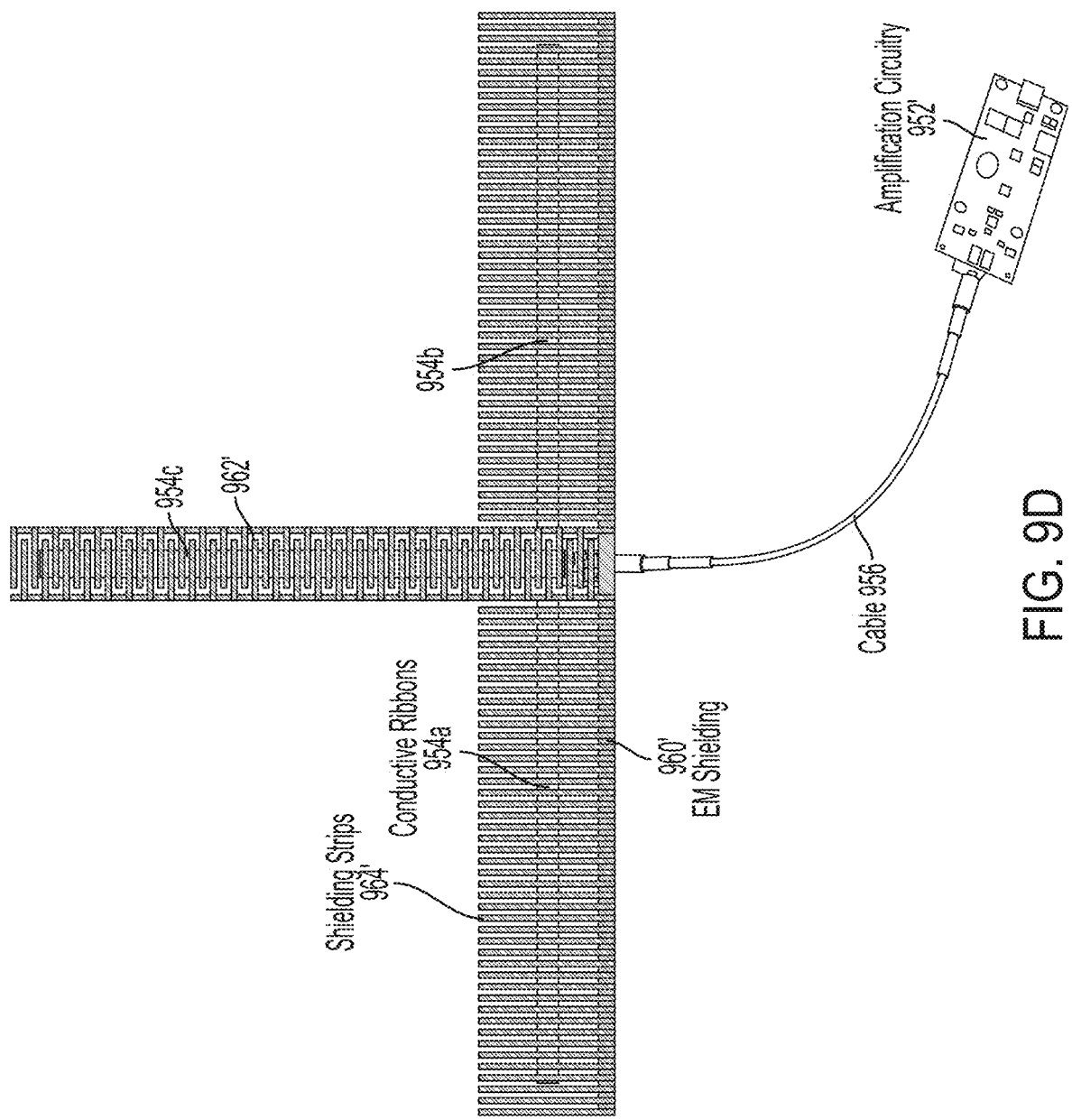
FIG. 9D is a drawing of the EFD of FIG. 9B and electromagnetic shielding for the conductors of the EFD, in accordance with some embodiments of the technology described herein.

FIG. 9D is a drawing of an EFD 950' that includes conductive ribbons 954a-954c and electromagnetic shielding 960' coupled to circuitry 952' by cable 256, in accordance with some embodiments. Electromagnetic shielding 960' includes three shield portions respectively disposed adjacent conductive ribbons 954a-954c. In some embodiments, each shield portion may be electrically coupled shielding of cable 256 via a connector interface (e.g., connector interface 955) that also electrically couples conductive ribbons 954a-954c to a signal conductor of cable 256. The shield portion disposed next to conductive ribbon 954c is configured in the manner described for electromagnetic shielding 960, such as including interdigitated fingers 962' configured in the manner described for interdigitated fingers 962. The other two shielding portions include shielding strips 964' elongated in a direction perpendicular to the direction of elongation of the respective conductive ribbon 954a or 954b and spaced from one another in the direction of elongation of the respective conductive ribbon. In some embodiments, shielding strips 964' may be configured to shield conductive ribbons 954a and 954b in the operating frequency range of the MRI system, as described herein for interdigitated fingers 962. For example, shielding strips 964' may be spaced from one another by a distance that is electrically small in the operating frequency range of the MRI system.

In some embodiments, it may be desirable to position the shield portions having shielding strips 964' about a circumference of an RF component of the MRI system (e.g., an RF coil), and to position the shield portion having interdigitated fingers 962' along a direction perpendicular to the circumference of the RF component. For example, electromagnetic shielding 960' may be disposed between conductive ribbons 954a-954c and an RF receive coil of the MRI system. In some embodiments, an RF coil housing may be disposed between the RF component and electromagnetic shielding 960'. Referring back to FIGS. 7A-7B, electromagnetic shielding 960' may be disposed between conductive strips 754a-754c and an interior surface of housing 762, with receive coils 714 disposed on an exterior surface of housing 762. During noise detection and/or imaging periods, electromagnetic shielding 960' may be configured to operate in the manner described for electromagnetic shielding 960 in connection with FIG. 9C.

While the three shielding portions of electromagnetic shielding 960' in FIG. 9D have different configurations, it should be appreciated that the shielding portions may each have a same configuration, such as each having interdigitated fingers 962' or each having shielding strips 964'.

Figure 10A:
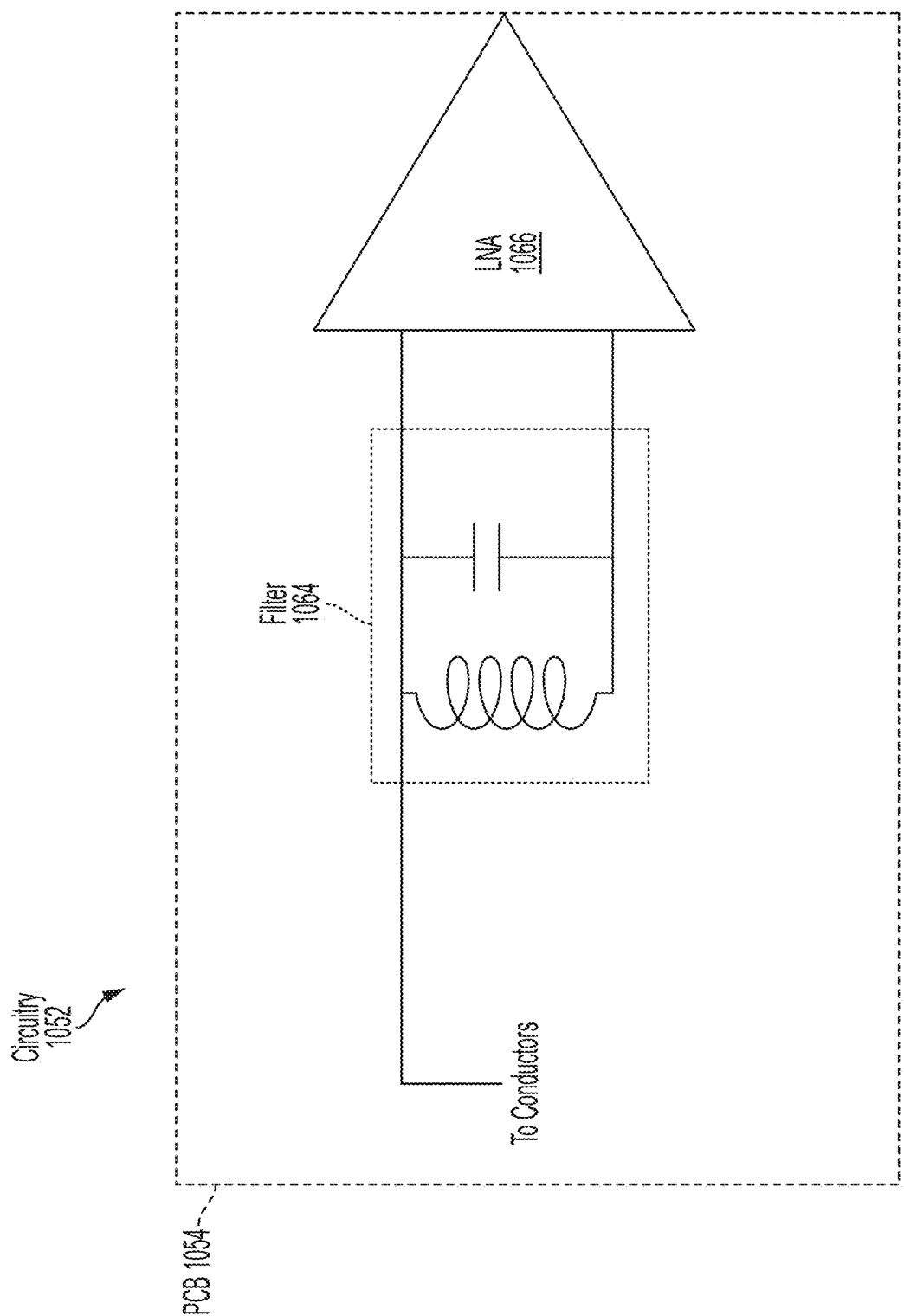
FIG. 10A illustrates circuitry for receiving and processing detected electromagnetic noise, in accordance with some embodiments.

FIG. 10A is a circuit diagram illustrating exemplary amplification circuitry 1052 configured to receive, convert, filter, amplify and/or otherwise process signals received from conductors of an EFD. Exemplary amplification circuitry 1052 includes filter 1064 and low noise amplifier (LNA) 1066 disposed on PCB 1054. Filter 1064 may be an inductor-capacitor (LC) filter having a resonant frequency range that overlaps with the operational frequency range of the MRI system (e.g., exemplary MRI system 400 illustrated in FIG. 4). For example, filter 1064 may be a passband filter having a passband centered on or near the nominal operating frequency and having a bandwidth on the same order as the imaging bandwidth of the MRI system. According to some embodiments, the output of filter 1064 is provided to LNA 1066 as an indication of electromagnetic interference or noise that may also be present in MRI signals detected by the MRI system in the operational frequency range. LNA 1066 may be a differential amplifier having a level of gain selected based on sensitivity requirements of the noise reduction component of the MRI system. The embodiment of amplification circuitry 1052 illustrated in FIG. 10A may be included in other types of sensors other than an EFD, as described further herein.

Figure 10B:
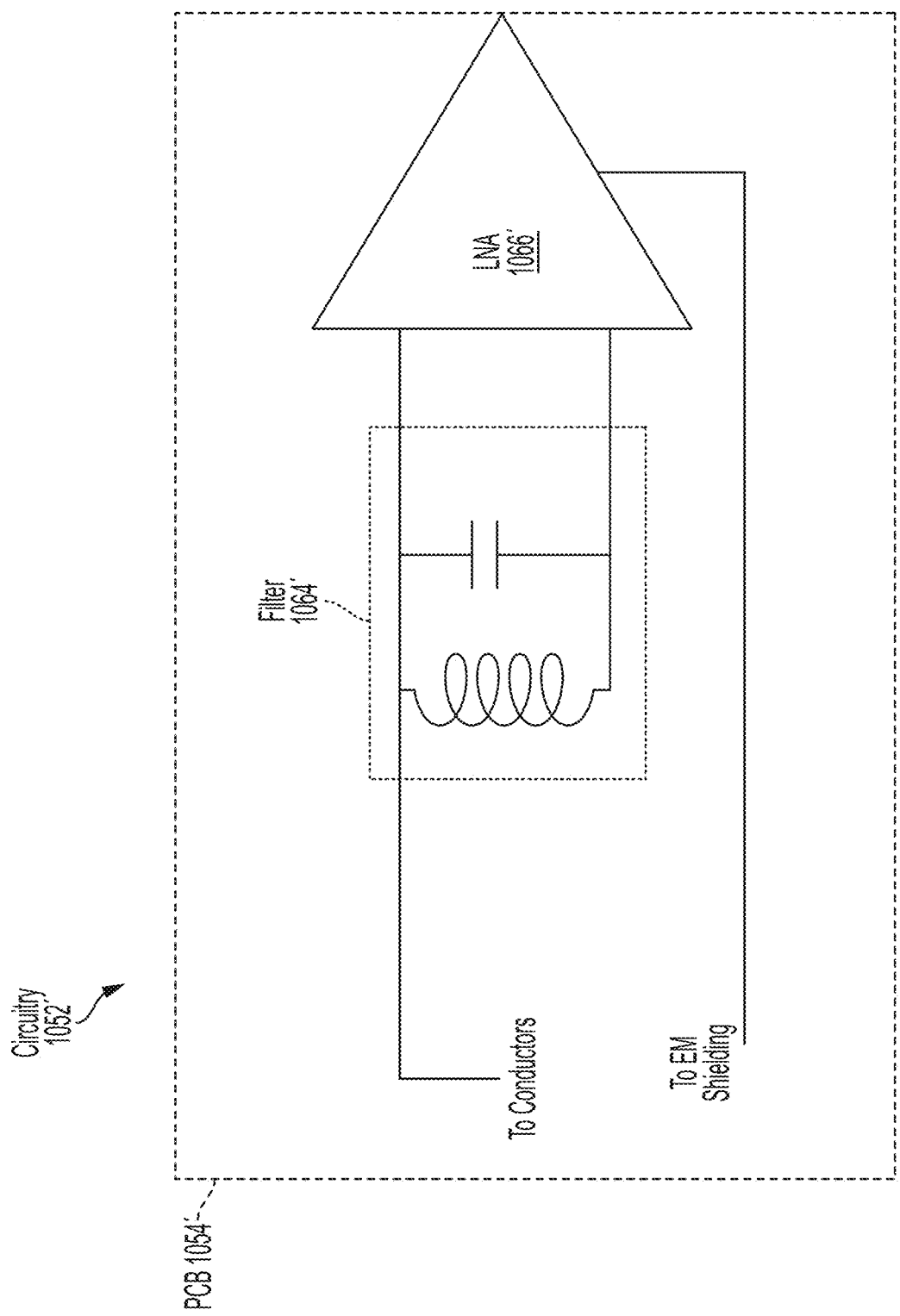
FIG. 10B illustrates alternative circuitry for receiving and processing detected electromagnetic noise, in accordance with some embodiments of the technology described herein.

FIG. 10B is a circuit diagram of alternative exemplary amplification circuitry 1052', which may be configured to process signals received from conductors of an EFD in the manner described for amplification circuitry 1052. For example, in FIG. 10B, amplification circuitry 1052 includes filter 1064' and LNA 1066', which may be configured in the manner described for filter 1064 and LNA 1066 in connection with FIG. 10A. In FIG. 10B, however, LNA 1066' is further configured for coupling to electromagnetic shielding. For example, referring back to FIG. 9D, differential inputs of LNA 1066' may be configured for coupling to conductive ribbons 954a-954c and a ground or reference input of LNA 1066' may be configured for coupling to electromagnetic shielding 960'. The inventors recognized that coupling electromagnetic shielding 960' to a ground or reference input of LNA 1066' improves detection of noise via an EFD. For example, a voltage level of the detected noise may be determined with reference to the voltage level of electromagnetic shielding 960', and the voltage difference may be amplified by LNA 1066', thereby isolating the detected noise from other sources of electromagnetic radiation (e.g., detected MR signals).

Figure 11A:
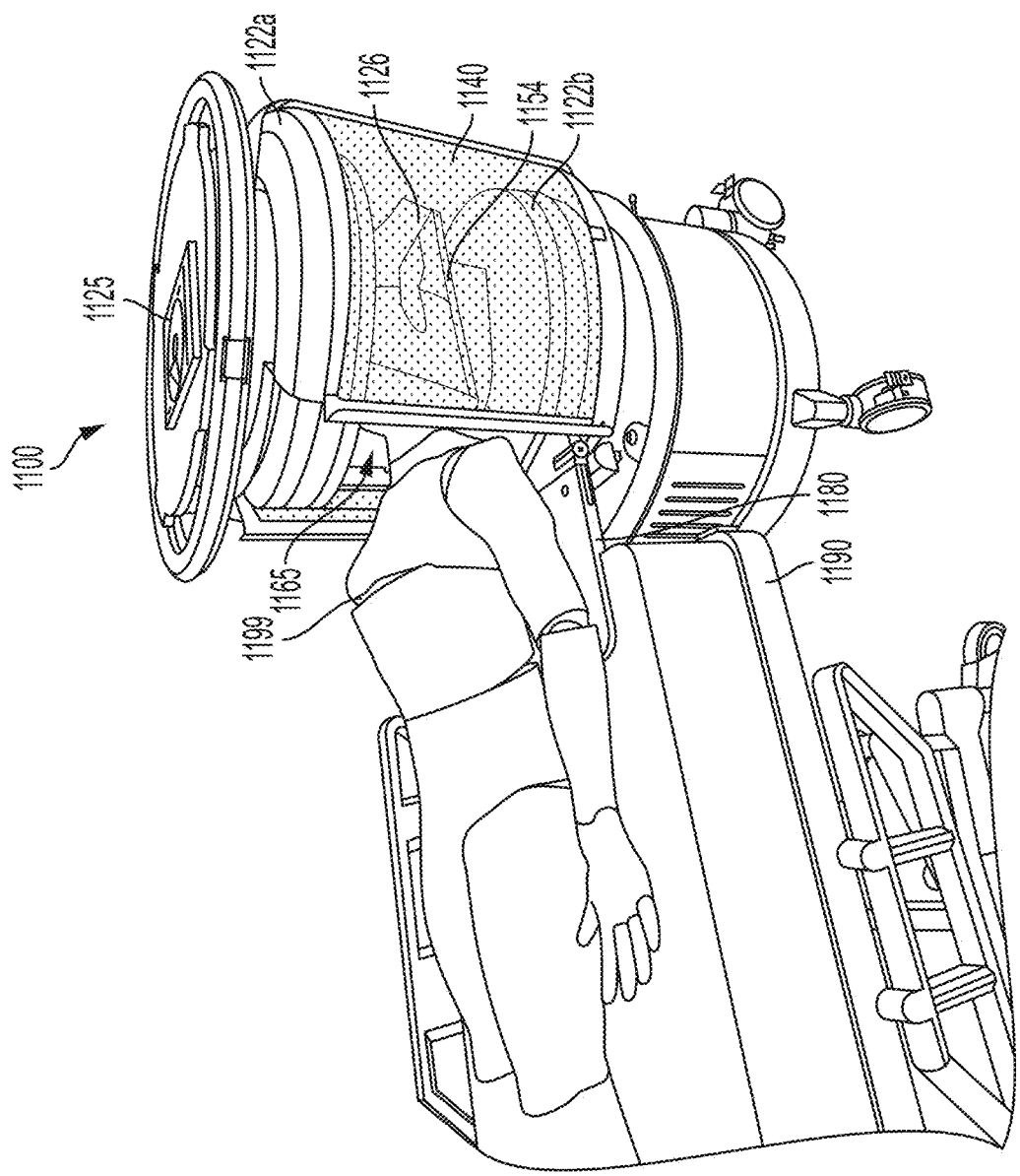
FIGS. 11A and 11B are drawings of an illustrative MRI system configured to detect electromagnetic noise conducted by a patient, in accordance with some embodiments of the technology described herein.

FIG. 11A illustrates an exemplary MRI system 1100 comprising a noise component configured to detect and suppress electromagnetic noise conducted by a patient, in accordance with some embodiments of the technology described herein. Components of MRI system 1100 may be configured in the manner described for the exemplary MRI systems described above. In the embodiment illustrated in FIG. 11A, the noise component comprises an EFD including an electrically conductive pad 1154 configured to conductively couple electromagnetic noise introduced into imaging region 1165 between upper $B_0$ magnet 1122a and lower $B_0$ magnet 1122b by patient 1199 as a result of electromagnetic energy coupling to the patient's body. Electromagnetic noise detected by pad 1154 may then be provided to the noise reduction system (e.g., a noise reduction system such as noise reduction system 1630 illustrated in connection with FIG. 16) during imaging to suppress and/or compensate for the electromagnetic noise introduced by the patient. For instance, electrically conductive pad 1154 may be coupled to the noise reduction system via a cable (not shown) directly or indirectly through amplification circuitry or other circuitry configured to process or transmit signals indicative of electromagnetic noise detected via pad 1154 that are conducted into imaging region 1165 by the patient, thus bypassing electromagnetic shields 1140.

In the illustrative embodiment of FIG. 11A, electrically conductive pad 1154 is disposed so that the patient physically contacts electrically conductive pad 1154 during imaging. For example, electrically conductive pad 1154 may be positioned in the imaging region of MRI system 1100 in a location where portions of the patient (e.g., neck, head, leg, etc.) may rest during imaging of the patient's appendage. Accordingly, the portions which rest on electrically conductive pad 1154 may conductively couple electromagnetic noise from the patient. Electrically conductive pad 1154 may provide the electromagnetic noise to the noise reduction system for suppression. For example, amplification circuitry may amplify the signals from conductive pad 1154 indicative of electromagnetic noise introduced by the patient and/or may process the signals to facilitate noise suppression prior to transmission to the noise reduction system.

Figure 11B:
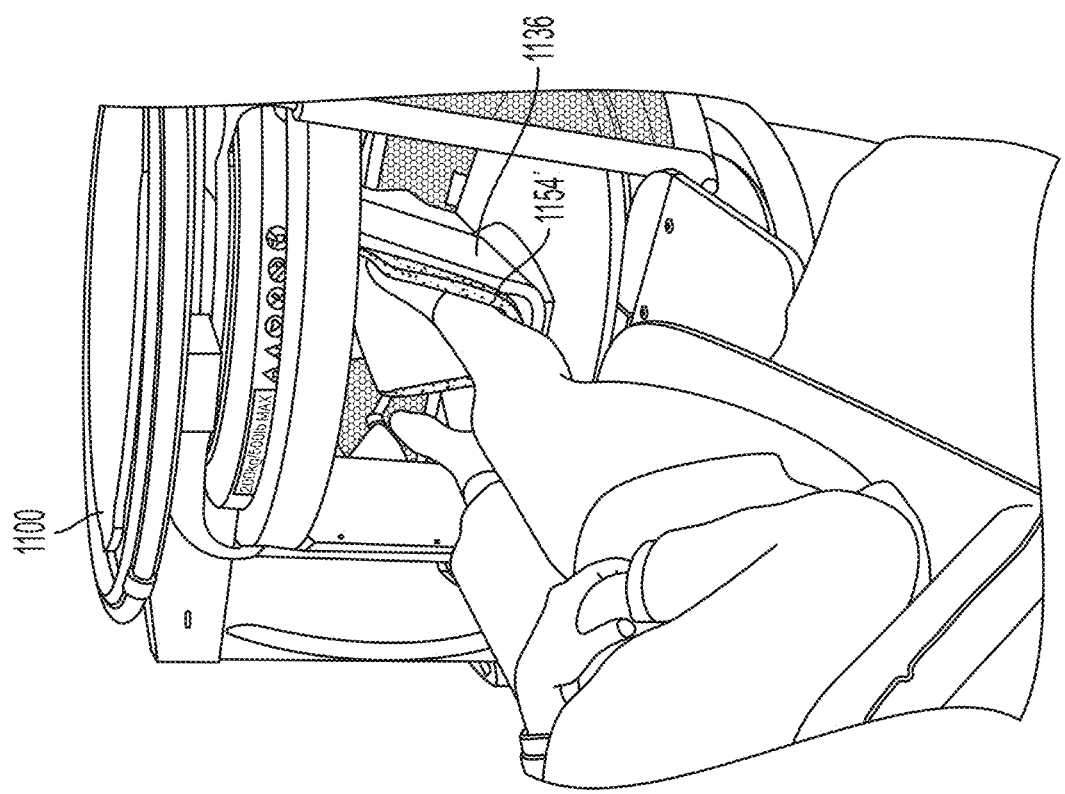

In some embodiments, electrically conductive pad 1154 may be configured for capacitively coupling electromagnetic noise from the patient rather than conductively. For example, in some embodiments, an electrically insulative layer may be disposed on electrically conductive pad 1154, providing cushioning support for the patient as well providing a dielectric layer between the two terminals of the capacitor (i.e., pad 1154 and the patient's body). The electrically insulative layer may be formed using any suitable insulative material such as foam or plastic, and may be soft or hard, with softness having the benefit of providing added comfort for the patient. FIG. 11B illustrates MRI system 1100 employed to image a foot. In this embodiment, an electrically conductive pad 1154' may be positioned with RF component 1136 to detect electromagnetic noise introduced by the patient.

In some embodiments, an electrically conductive pad configured in the manner described for electrically conductive pad 1154 may be alternatively or additionally configured to be worn by the patient. For example, the electrically conductive pad may wrap around the patient's neck, leg, or other suitable portions of the patient. Accordingly, the electrically conductive pad may conductively couple electromagnetic noise from the patient when an electrically conductive portion of the pad physically contacts the patient. Alternatively or additionally, the electrically conductive pad may capacitively couple electromagnetic noise from the patient when an electrically conductive portion of the pad is positioned close to the patient, without necessarily physically contacting the patient. One or more insulative layers (e.g., as described for electrically conductive pad 1154) may separate the patient from the electrically conductive portion.

Figure 12:
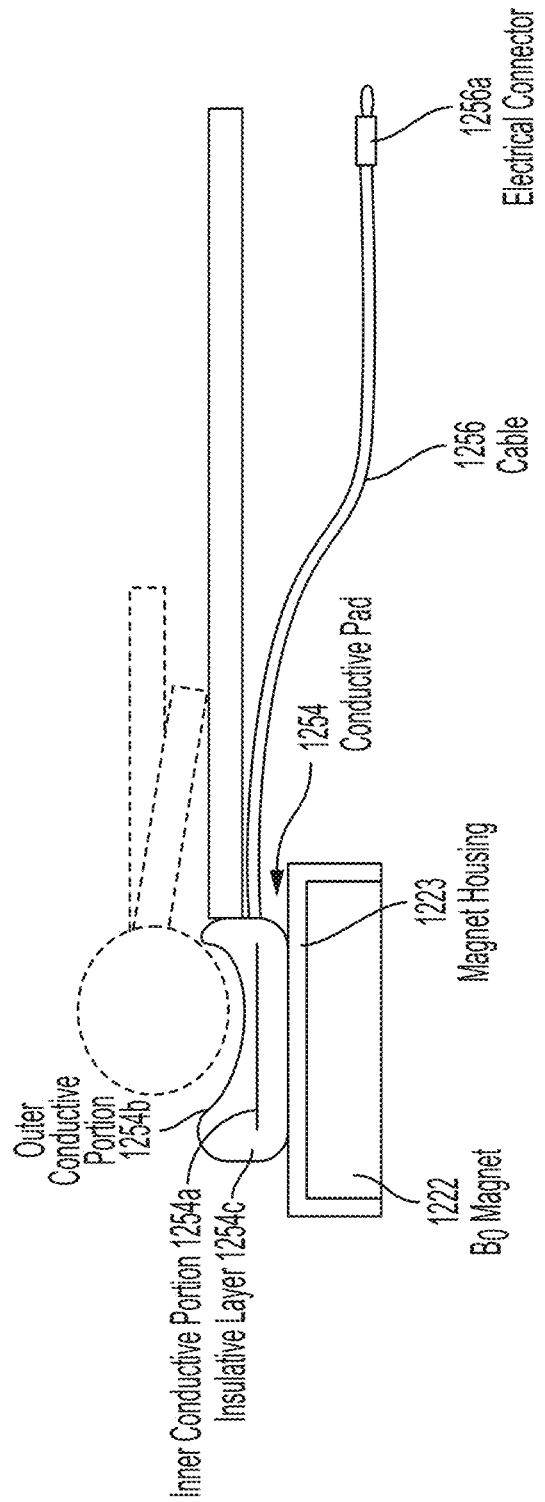
FIG. 12 is a drawing of an electrically conductive pad for an MRI system configured to detect electromagnetic noise conducted by a patient, in accordance with some embodiments of the technology described herein.

FIG. 12 further illustrates electrically conductive pad 1254, including one or more conductive portions 1254a and 1254b, and insulative layer 1254c. One or each of conductive portions 1254a and 1254b may be coupled to the noise reduction system of the MRI system via cable 1256 and electrical connector 1256a. In some embodiments, electrical connector 1256a may be configured for removably coupling to processing circuitry of the MRI system. In the illustrated embodiment in FIG. 12, electrically conductive pad 1254 is positioned above (lower) $B_0$ magnet 1222 and supported by an upper surface of magnet housing 1223.

According to some embodiments, electrically conductive pad 1254 may include inner conductive portion 1254a. As illustrated, inner conductive portion 1254a is disposed within insulative layer 1254c and configured for capacitively coupling to the patient through insulative layer 1254c. For example, during imaging, the patient's head, foot, and/or another portion of the patient may be positioned in the imaging region above and/or below $B_0$ magnet 1222, and electrically conductive pad 1254 may be positioned as shown with inner conductive portion 1254a separated from the patient by insulative layer 1254c. The patient's head may be within capacitive coupling range of inner conductive portion 1254a, allowing electromagnetic noise to couple through insulative layer 1254c. Cable 1256 (e.g., coaxial cable, plastic coated copper wire, etc.) and electrical connector 1256a (e.g., coaxial cable connector, banana jack, etc.) may provide the electromagnetic noise to the noise reduction system for suppression. It should be appreciated that electrically conductive pad 1254 (e.g., insulative layer 1254c) does not need to physically contact the patient for capacitive coupling to be effected. In some embodiments, multiple inner conductive portions 1254a and/or insulative layers 1254c may be included. Moreover, in some embodiments, electrically conductive pad 1254 may be positioned above or otherwise adjacent the patient for capacitively coupling thereto.

Alternatively or additionally, in some embodiments, electrically conductive pad 1254 may include outer conductive portion 1254b which is positioned on an outer surface of electrically conductive pad 1254 for conductively coupling to the patient. In some embodiments, insulative layer 1254c may be coated and/or attached to, or otherwise support outer conductive portion 1254b for conductively coupling to the patient during imaging. For example, during imaging, the patient's head, foot, and/or another portion of the patient may be positioned in the imaging region and outer conductive portion 1254b may physically contact the patient to conductively couple electromagnetic noise from the patient. It should be appreciated that outer conductive portion 1254b may capacitively couple electromagnetic noise from the patient, such as in embodiments in which outer conductive portion 1254b does not physically contact the patient. Moreover, some embodiments may include both inner and outer conductive portions 1254a and 1254b.

Figure 13:
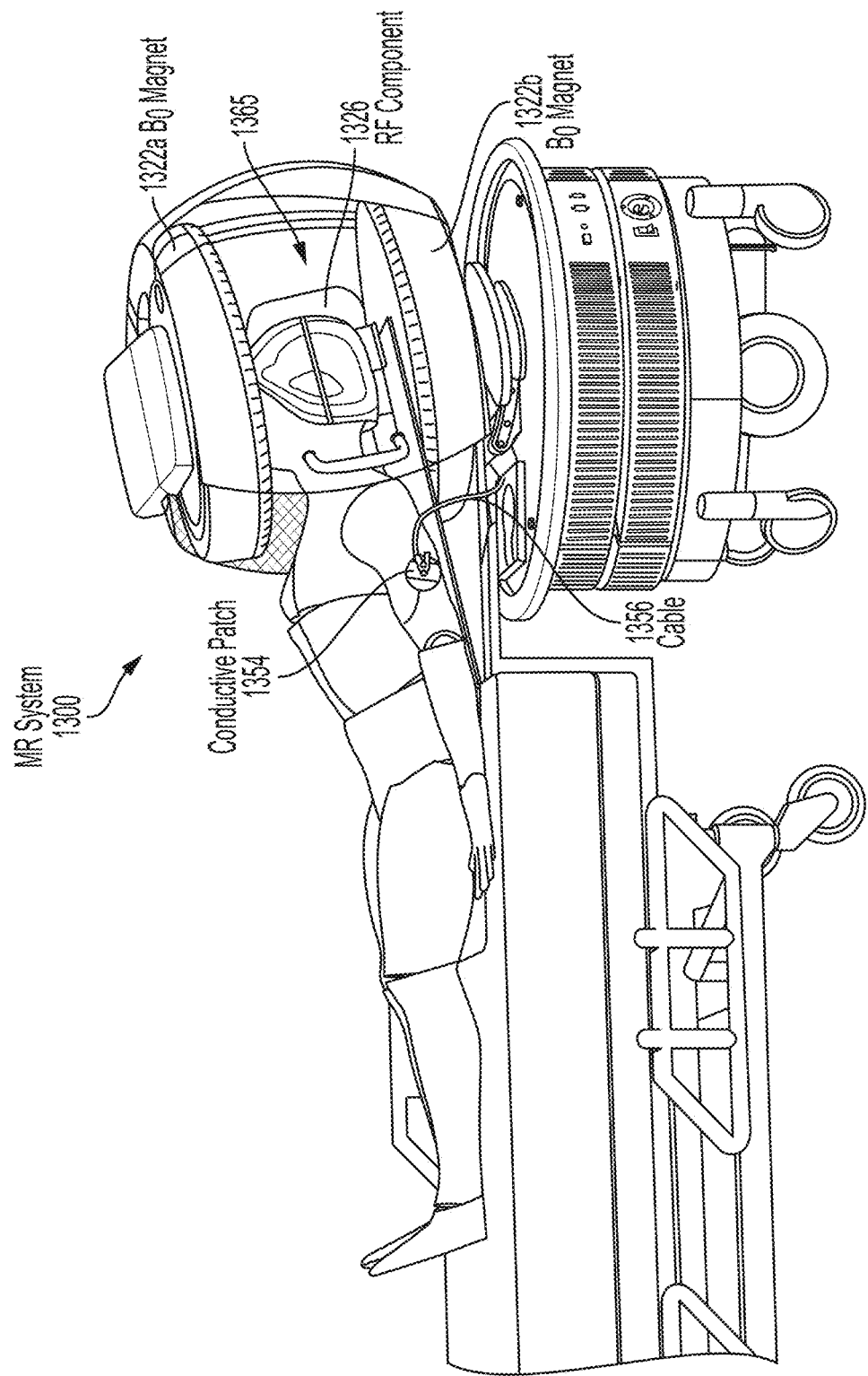
FIG. 13 is a drawing of an illustrative MRI system configured to detect electromagnetic noise conducted by a patient, in accordance with some embodiments of the technology described herein.

FIG. 13 shows an illustrative embodiment of an MRI system 1300 comprising a noise reduction component configured to detect and suppress electromagnetic noise conducted by a patient during imaging, in accordance with some embodiments. For example, MR system 1300 is configured to image the patient's head by utilizing RF component 1326 positioned within imaging region 1365 formed by upper $B_0$ magnet 1322a and lower $B_0$ magnet 1322b and adapted to accommodate the patient's head during imaging. As described above, the patient may introduce electromagnetic noise into imaging region 1365 from the environment that is detected by one or more receive coils of RF component 1326. To detect at least some of the electromagnetic noise that couples to the patient, conductive patch 1354 is attached to the patient (e.g., the patient's arm) at a location outside of imaging region 1365 of MRI system 1300. Electrically conductive patch 1354 is configured for attaching to the patient to conductively couple electromagnetic noise from the patient to the noise reduction system, such as via amplification circuitry or other circuitry configured to receive signals from patch 1354 indicative of electromagnetic noise that has coupled to the patient. For instance, cable 1356 may couple electrically conductive patch 1354 to the noise reduction system either directly or indirectly.

Figure 14:
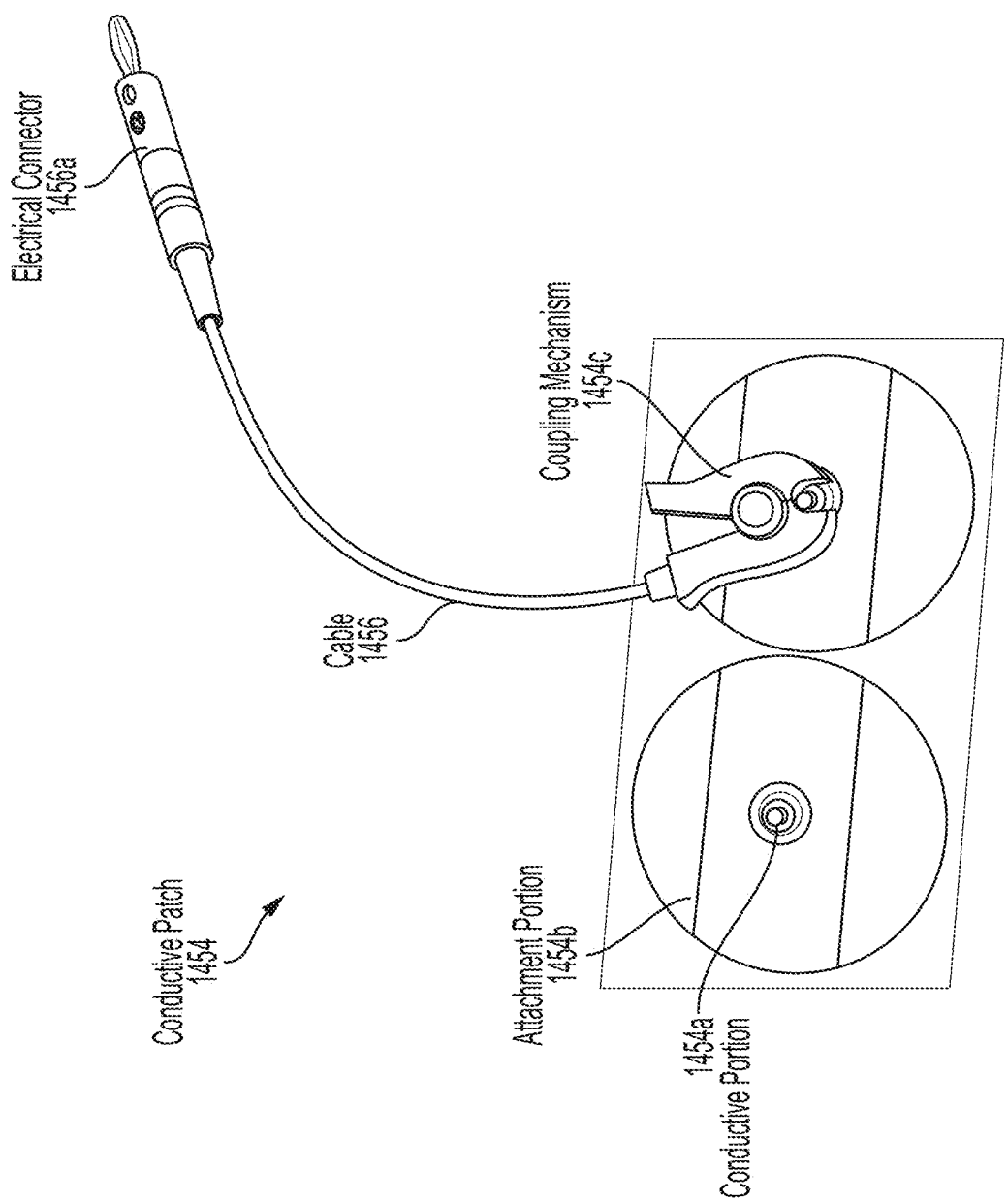
FIG. 14 is a drawing of an electrically conductive patch for an MRI system configured to detect electromagnetic noise conducted by a patient, in accordance with some embodiments of the technology described herein.

FIG. 14 further illustrates electrically conductive patch 1454. In the illustrated embodiment, electrically conductive patch 1454 is an adhesive electrode. For example, electrically conductive patch 1454 may include conductive portion 1454a for conductively coupling to the patient and attachment portion 1454b that adheres to the patient, such as to the patient's skin. Attachment portion may be formed using an insulative rather than conductive material. In some embodiments, the electrode may alternatively or additionally include an at least partially conductive adhesive layer (not shown) to attach conductive portion 1454a to the patient. By attaching conductive portion 1454a to the patient, electromagnetic noise conducted by the patient may be conductively coupled from the patient to electrically conductive patch 1454, facilitating suppression by the noise reduction system.

In some embodiments, electrically conductive patch 1454 may be configured for capacitively coupling electromagnetic noise from the patient rather than conductively. For example, in some embodiments, an electrically insulative layer (not shown) may be disposed on a side of electrically conductive pad 1454, such as to adhere conductive pad 1454 to the patient. The electrically insulative layer may be formed using any suitable insulative and/or adhesive material such as foam, plastic, and/or glue, and may be soft or hard, with softness having the benefit of providing added comfort for the patient.

In some embodiments, cable 1456 may releasably attach to conductive patch 1454, such as by clipping or plugging to conductive portion 454a via coupling mechanism 1454c. Cable 1456 may be a copper wire in a plastic jacket. In this illustrated embodiment, coupling mechanism 1454c is a spring clip. In addition, cable 1456 may terminate in electrical connector 1456 for removably coupling to a complementary electrical connector of the MRI system (e.g., to amplification circuitry and/or the noise reduction system). In the illustrated embodiment, electrical connector 1456 is a banana jack. The inventors have recognized that, by removably coupling cable 1456 to other portions of the MRI system, damage to electrically conductive patch 1454, cable 1456 and/or other components of the system may be avoided in the event that force is exerted on cable 1456, such as if the patient were to move away from the MRI system prior to detaching electrically conductive patch 1454 from the patient. For example, electrical connector 456a may be removed from a complementary electrical connector responsive to a pulling force, preventing such damage from occurring.

It should be appreciated that, in some embodiments, electrically conductive pad 1454 may be coupled to other portions of the MRI system by a coaxial cable (e.g., as cable 1456), as described herein for EFD 950. Accordingly, electrical connectors and/or coupling mechanisms described for electrically conductive pad 1454 may be coaxial cable connectors. Such coaxial cable connectors may facilitate coupling of electromagnetic noise at high frequencies not supported by copper wire cables.

Figure 15A:
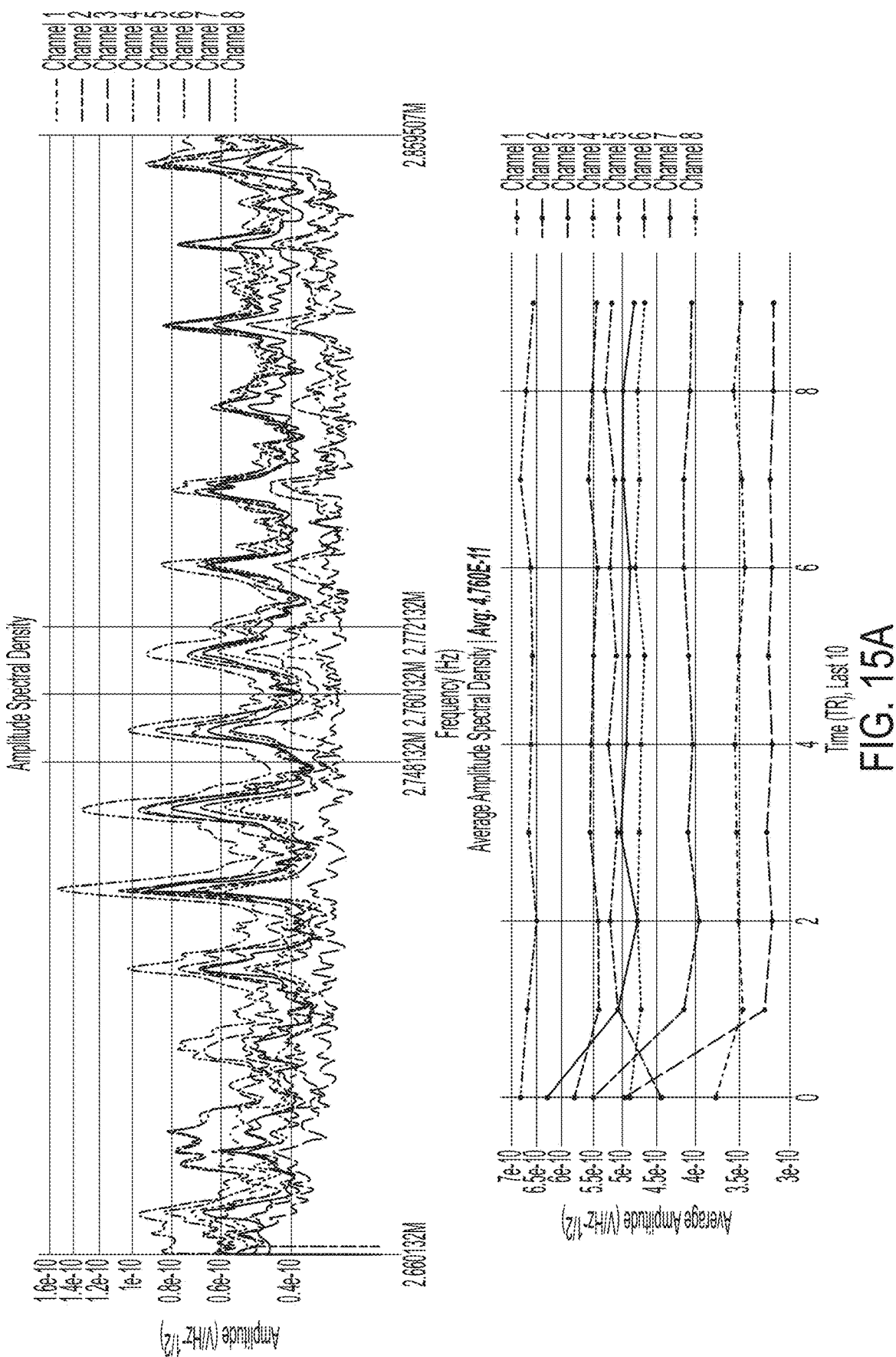
FIGS. 15A-B illustrate detected signals and images acquired by an MRI system with an ECG device present and operating using a patient grounding technique.
Figure 15B:
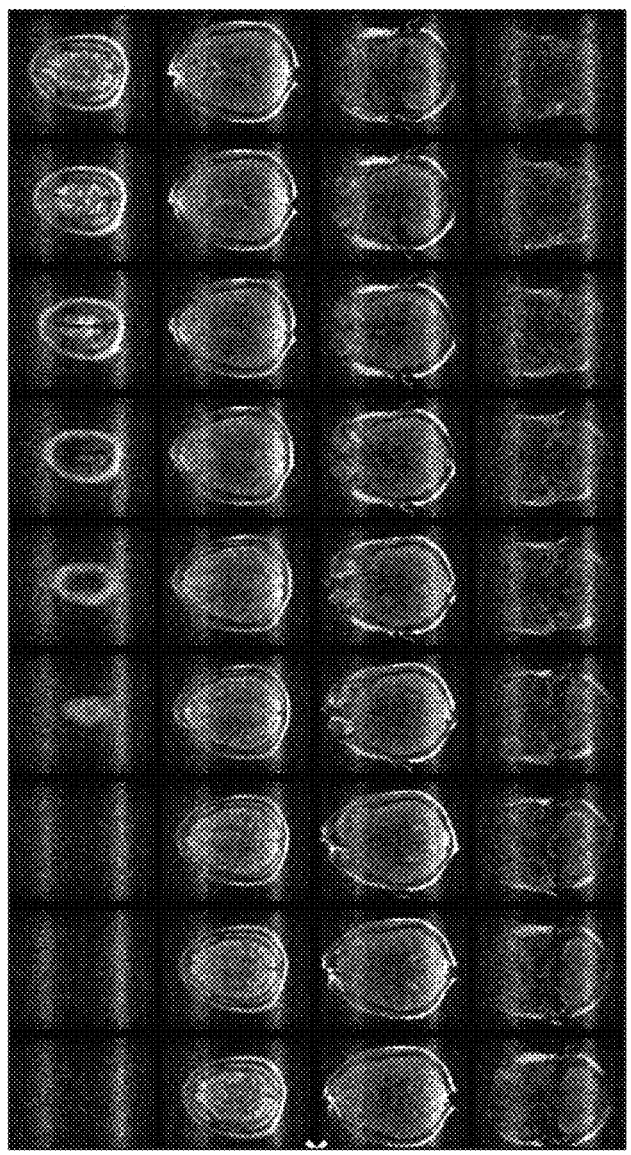
Figure 15C:
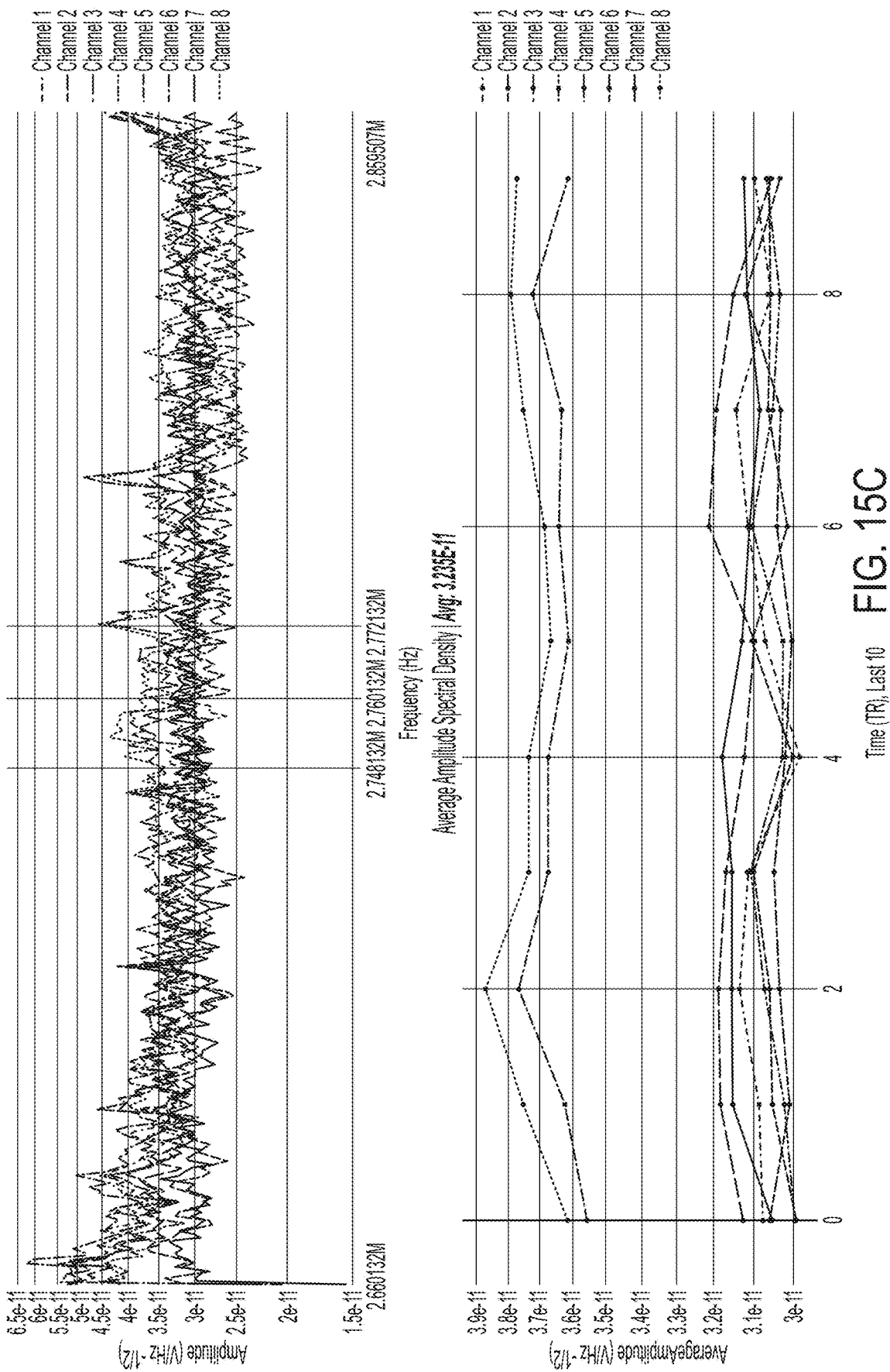
FIGS. 15C-D illustrate detected signals and images acquired by an MRI system with an ECG device present and operating using noise detection and suppression techniques, in accordance with some embodiments.
Figure 15D:
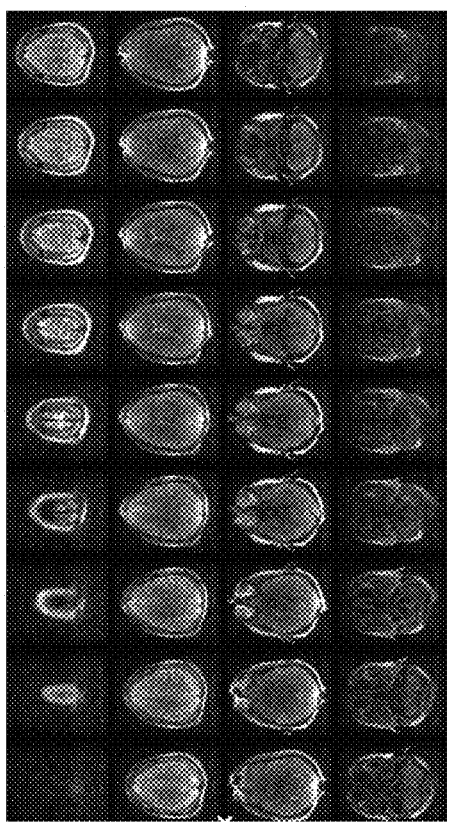

Significant electromagnetic radiation may couple to a patient who is connected to other medical equipment during MRI. For example, when a patient is connected to ECG equipment, additional noise may be injected into the MRI system that is difficult to suppress. FIG. 15A illustrates the amplitude spectral density and average amplitude spectral density of the signal detected on each of 8 channels of an array of eight receive coils when the patient is connected to an ECG during imaging using the technique of grounding the patient to suppress electromagnetic noise conducted by the patient. FIG. 15B illustrates the images reconstructed from the signals detected by the receive coil array illustrated in FIG. 15A where the noise from the ECG is clearly visible as artifacts in the images. FIG. 15C the amplitude spectral density and average amplitude spectral density of the signal detected on each of 8 channels of an array of eight receive coils when the patient is connected to an ECG during imaging using the electromagnetic noise detection and suppression techniques described herein. FIG. 15D illustrates the images reconstructed from the signals detected by the receive coil array illustrated in FIG. 15C, showing improvement in suppressing noise from the ECG device introduced by the patient.

Figure 16:
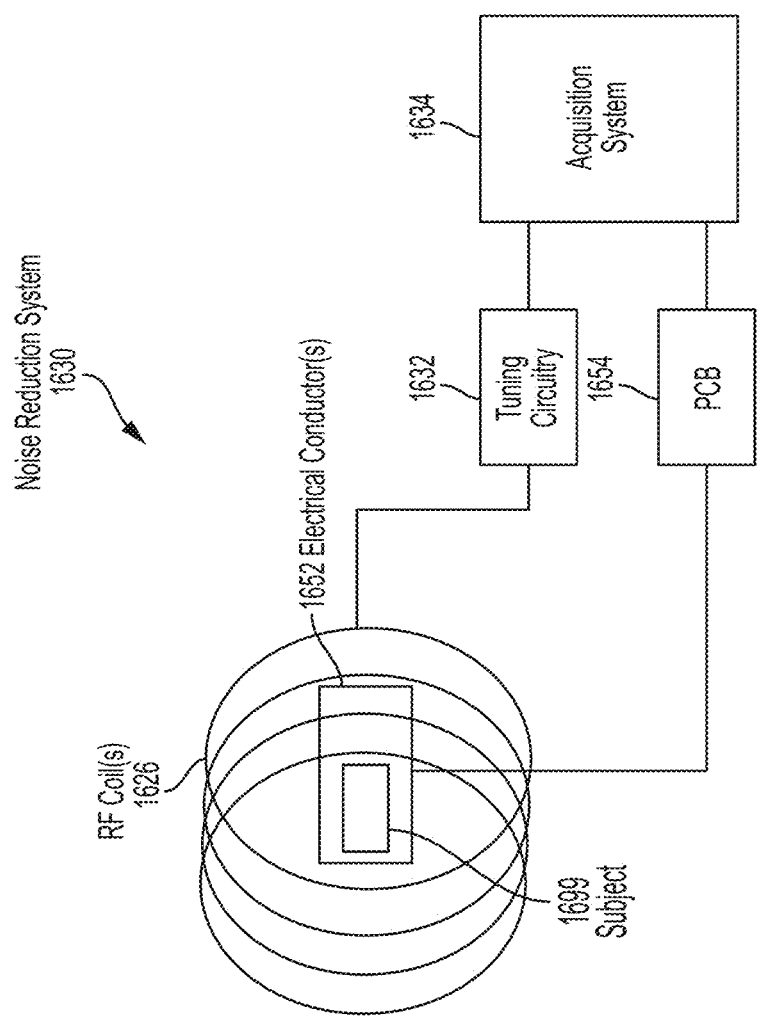
FIG. 16 is a drawing of an illustrative noise reduction system for an MRI system configured to isolate electromagnetic noise conducted by a patient, in accordance with some embodiments of the technology described herein.

FIG. 16 is a drawing of illustrative noise reduction system 1630 for an MRI system configured to isolate electromagnetic noise conducted by a patient, in accordance with some embodiments of the technology described herein. In the illustrative embodiment of FIG. 16, noise reduction system 1630 is configured to detect MR signals emitted from excited atoms of a subject 1699 being imaged, and to characterize electromagnetic noise conducted by a patient and detected by a sensor of the MRI system, the sensor including electrical conductor(s) 1652 and circuitry 1654 (e.g., amplification circuitry), which is shown in FIG. 16 on a PCB. Noise reduction system 1630 may suppress or remove the detected noise from the detected MR signals, as described in further detail below.

In the illustrative embodiment of FIG. 16, noise reduction system 1630 includes primary RF receive coil 1626 configured to measure MR signals emitted by a patient in response to an excitation pulse sequence (e.g., a pulse sequence selected from pulse sequence repository 108 and executed by controller 106). The excitation pulse sequence may be produced by primary RF receive coil 1626 and/or by one or more other transmit RF coils arranged proximate the patient and configured to produce suitable MR pulse sequences when operated. Primary receive coil 1626 may be a single coil or may be a plurality of coils, which, in the latter case, may be used to perform parallel MRI. Tuning circuitry 1632 facilitates operation of primary receive coil 1626 and signals detected by RF coil(s) 1626 are provided to acquisition system 1634, which may amplify the detected MR signals, digitize the detected signals, and/or perform any other suitable type of processing.

Noise reduction system 1630 also interfaces with electrical conductor(s) 1652, which may be configured to conductively and/or capacitively couple electromagnetic noise from the patient. For example, the sensor may be EFD 950, and electrical conductor(s) 1652 may be electrical conductor(s) 954a-954c or the like. Alternatively or additionally, electrical conductor(s) may include electrically conductive pad 1254 and/or electrically conductive patch 1454, in accordance with various embodiments. In any case, the noise detected by the sensor may be characterized and used to suppress noise in the MR signal detected by primary RF coil(s) 1626 using techniques described in further detail below. After acquisition system 1634 processes the signals detected by RF coil(s) 1626 and electromagnetic noise detected by the sensor, acquisition system 1634 may provide the processed signals to one or more other components of the MRI system for further processing (e.g., for use in forming one or more MR images of the patient). Acquisition system 1634 may include any suitable circuitry and may include, for example, one or more controllers and/or processors configured to control the MRI system to perform noise suppression.

Additionally, in some embodiments, one or more auxiliary sensors may be included to detect electromagnetic noise in an operating environment of the MRI system. In some embodiments, the auxiliary sensor(s) may include one or more auxiliary coils configured to measure noise from one or more noise sources in the environment in which the MRI system is operating. In some instances, the auxiliary RF coil(s) may be constructed to be substantially more sensitive to ambient noise than to any noise generated by the coil itself. For example, the auxiliary RF coil may have a sufficiently large aperture and/or a number of turns such that the auxiliary coil is more sensitive to noise from the environment than to noise generated by the auxiliary coil itself. In some embodiments, auxiliary RF coil(s) may have a larger aperture and/or a greater number of turns than primary RF coil(s) 1626. However, auxiliary RF coil(s) may be the same as primary RF coil in this respect and/or may differ from primary RF coil(s) 1626 in other respects, as the techniques described herein are not limited to any particular choice of coils. For example, in some embodiments, an auxiliary sensor of a different type is used in place of an RF coil type sensor. Further aspects of noise reduction systems, such as noise reduction system 1630, are described in U.S. Pat. Application Publication No.: 2016/0069970, which is herein incorporated by reference in its entirety.

Figure 17:
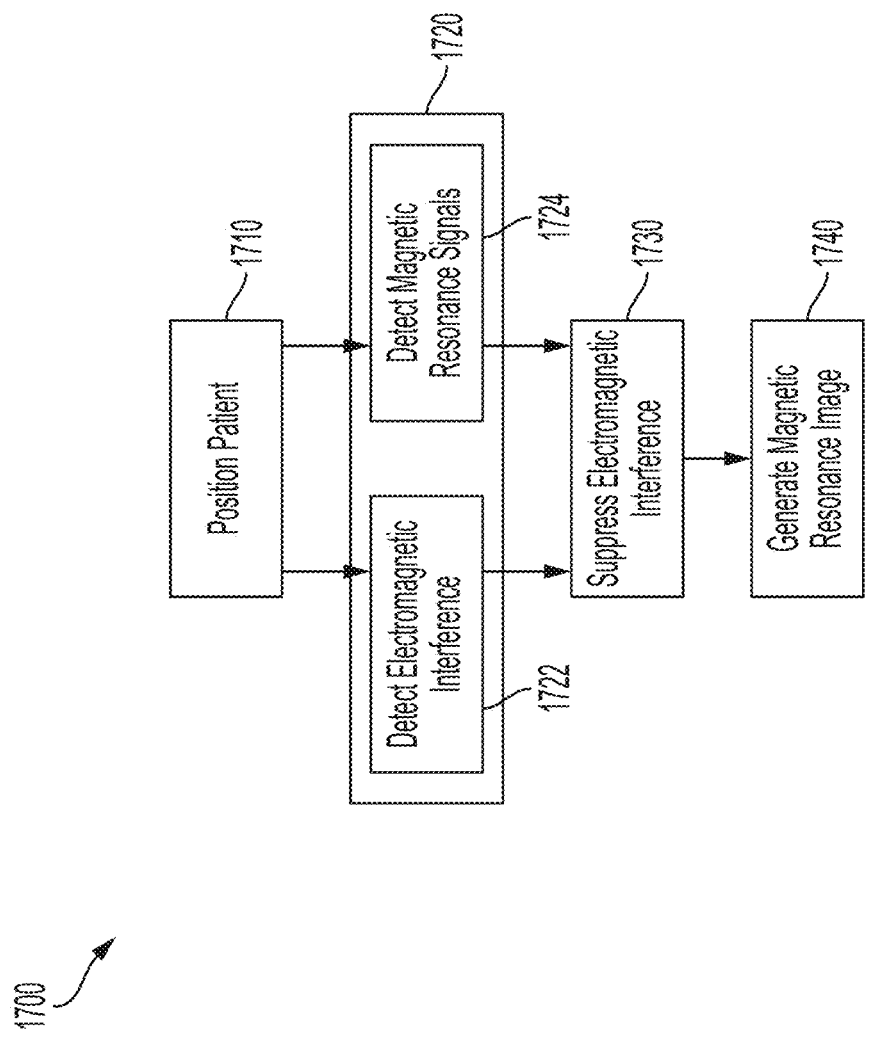
FIG. 17 is a drawing of an illustrative method for operating an MRI system configured to detect electromagnetic noise conducted by a patient, in accordance with some embodiments of the technology described herein.

FIG. 17 is a drawing of illustrative method 1700 for operating an MRI system configured to configured to detect electromagnetic noise conducted by a patient, in accordance with some embodiments of the technology described herein. In act 1710, a patient is positioned for imaging by an MRI system, for example, a point-of-care MRI system capable of being operated outside of specially shielded rooms. For example, the MRI system may be transported next to the hospital bed of the patient (or the hospital bed may be moved to the MRI system) and the anatomy or portion of the anatomy to be imaged may be positioned within the imaging region of the MRI system. After the patient is properly positioned, the MRI system may be operated in act 1720. In particular, a radio frequency component of the MRI system may be operated to transmit RF pulses configured to cause a magnetic resonance response in the portion of the patient being imaged. For example, one or more transmit coils may be operated to generate an RF pulse sequence that results in MR signals being emitted from the portion of the patient's anatomy positioned within the imaging region of the MRI system. In addition, one or more other magnetics components (e.g., one or more gradient coils, one or more shim coils and/or one or more $B_0$ electromagnets in embodiments that utilize electromagnets to produce or contribute to the $B_0$ magnetic field) may be operated to generate magnetic fields used in MRI.

During operation of the MRI system (e.g., interleaved with repeated RF pulse transmissions), acts 1722 and 1724 may be performed. In particular, components of the MRI system may be operated to detect electromagnetic interference, including electromagnetic radiation introduced from the environment by the patient (act 1722). Additionally, MR signals emitted from the patient may be detected by one or more receive coils arranged proximate the portion of the anatomy of the patient being imaged (act 1724). As described above, the MRI system's receive coil(s) may also detect electromagnetic interference, including electromagnetic radiation that couples to the patient from the environment and is introduced into the MRI system (e.g., via the opening in electromagnetic shielding through which the patient is positioned within the imaging region of the MRI system). As a result, the signal detected by the one or more receive coils will typically include both MR signal and electromagnetic interference, thereby reducing SNR and, ultimately, image quality.

Detecting electromagnetic interference conducted by the patient in act 1722 may be performed by using any of the techniques described herein, for example, using a sensor positioned proximate the anatomy of the patient being imaged. In some embodiments, the sensor may be an electrical field detector (e.g., any of the exemplary EFDs described herein). Accordingly, during act 1710, the patient may be positioned within capacitive coupling range of one or more electrical conductors of the EFD, at least some of which are positioned in the imaging region of the MRI system (e.g., affixed to a radio frequency component of the MRI system). For example, one or more electrical conductors of the EFD may be positioned on or within a housing of a radio frequency component configured to accommodate the portion of the patient's anatomy being imaged such that positioning the patient's anatomy within the housing effects capacitive coupling between the EFD and the patient. In some embodiments, the EFD may include electromagnetic shielding positioned between the conductor(s) of the EFD and the radio frequency component of the MRI system. For example, the electromagnetic shielding may prevent the conductor(s) of the EFD from coupling to one or more RF receive coil(s) of the MRI system.

In some embodiments, detecting electromagnetic interference may include using a sensor that includes an electrically conductive pad. In some embodiments, the patient is positioned in act 1710 to physically contact the electrically conductive pad, causing electromagnetic interference to conductively couple from the patient to the electrically conductive pad. For example, prior to imaging, the patient may be positioned on top of an electrically conductive pad. Alternatively or additionally, an electrically conductive pad may be positioned over the patient or otherwise placed into physical contact with the patient. In some embodiments, the patient may be brought into physical contact with an electrically conductive portion on an outer surface of the electrically conductive pad. For example, the electrically conductive pad may be positioned with the outer surface facing the patient, bringing the patient into physical contact with the electrically conductive portion on the outer surface.

Alternatively or additionally, in some embodiments, the patient may be positioned within a capacitive coupling range of the electrically conductive pad. For example, prior to imaging (e.g., during performance of act 1710), the patient may be positioned on top of the electrically conductive pad and close enough to the pad to effect capacitive coupling without necessarily making physical contact with the pad. In some embodiments, the patient may be positioned within a capacitive coupling range of an electrically conductive portion of the electrically conductive pad. For example, the patient may be positioned over an electrically conductive portion of the electrically conductive pad with one or more insulative layers, such as cushioning layers, separating the patient from the electrically conductive portion and providing the dielectric of the capacitive coupling between the conductive pad and the patient. The insulative layer(s) may also provide comfort to the patient.

In some embodiments, an electrically conductive pad may be positioned on or over a portion of the patient, such that the patient may wear the electrically conductive pad during imaging. For example, an electrically conductive pad may be wrapped around the patient's neck, leg, or other suitable portions of the patient. Accordingly, the electrically conductive pad may be positioned to conductively couple electromagnetic noise from the patient when an electrically conductive portion of the pad physically contacts the patient. Alternatively or additionally, an electrically conductive pad may be positioned to capacitively couple electromagnetic interference from the patient when an electrically conductive portion of the pad is positioned close to the patient, without necessarily physically contacting the patient. The patient may be separated from the electrically conductive portion by one or more insulative layers.

In some embodiments, the sensor may include an electrically conductive patch attached (e.g., adhered, affixed, etc.) to the patient. For example, prior to imaging, an electrically conductive patch may be attached to the patient's arm, leg, or any portion of the patient. It should be appreciated that more than one electrically conductive patch may be attached to the patient in the same or different locations on the patient's body. In some embodiments, an electrically conductive patch may be adhered to the patient's skin. For example, the electrically conductive patch may include an adhesive layer and/or an adhesive layer may be applied to the electrically conductive patch prior to attachment to the patient. Accordingly, in some embodiments, an electrically conductive portion of the electrically conductive patch may be placed in physical contact with the patient. Alternatively or additionally, an electrically conductive portion of the electrically conductive patch may be positioned in capacitive coupling range of the patient. For example, when an electrically conductive patch is attached to the patient, the patient may not physically contact the electrically conductive portion, as it may be separated from the patient by one or more insulative layers, but the electrically conductive portion may be close enough to capacitively couple to the patient. The insulative layer(s) may provide comfort to the patient, and/or may include an attaching (e.g., adhesive) layer which facilitates attachment of the electrically conductive patch to the patient.

As described above, the capacitive coupling range described herein refers to a range at which electrical energy may be coupled efficiently among two or more conductive objects. In general, capacitive coupling depends on multiple factors. Typically, two or more electrically conductive objects (e.g., plates, sheets or any other suitable object) capacitively couple electrical energy to and from one another at a range of frequencies dependent on the capacitance among the conductive objects. The capacitance is determined based on a surface area of each object, a dielectric constant of the material(s) separating the objects, and the spacing among the objects. Larger surface areas of the objects, materials having a higher dielectric constant separating the objects, and closer spacing among the objects may increase the capacitance. Given a capacitance, electrical energy may be capacitively coupled efficiently due to very little impedance at a certain frequency range and electrical energy may not be capacitively coupled efficiently due to large impedance at another frequency range. For example, a capacitance of 1 nF between two objects may result in a low impedance (e.g., approximately 60Ω) at 2.6 MHz, and a high impedance (e.g. approximately 2.6 MΩ) at 60 Hz. Efficient capacitive coupling as described herein may occur for a particular capacitance at a frequency range in which the impedance is below 250Ω.

In act 1730, electromagnetic interference detected in act 1722 is suppressed, compensated for, or otherwise mitigated in MR signals detected in act 1724. For example, electromagnetic interference detected by an EFD that is capacitively and/or conductively coupled to the patient may be coupled directly or indirectly (e.g., via amplification circuitry) to a noise reduction system of the MRI system, facilitating suppression of electromagnetic noise detected by the EFD during act 1772 in MR signals detected by the MRI system in act 1724. In some embodiments, the electromagnetic interference may be sampled, such as using an analog to digital converter (ADC) electrically coupled to amplification circuitry that receives the electromagnetic interference from the EFD. In some embodiments, the noise reduction system may subtract a version of the electromagnetic noise sampled during act 1772 from the MR signals received during act 1724. For example, the noise reduction system may apply a transfer function to the sampled electromagnetic interference and subtract transformed versions of the sampled electromagnetic interference from the received MR signals.

In act 1740, the MR signals for which electromagnetic interference has been suppressed or compensated for are than used to generate one or more magnetic resonance images. Because the SNR of the detected MR signals is increased upon suppression of electromagnetic interference, the quality of images produced by the MRI system may be improved.

Figure 18:
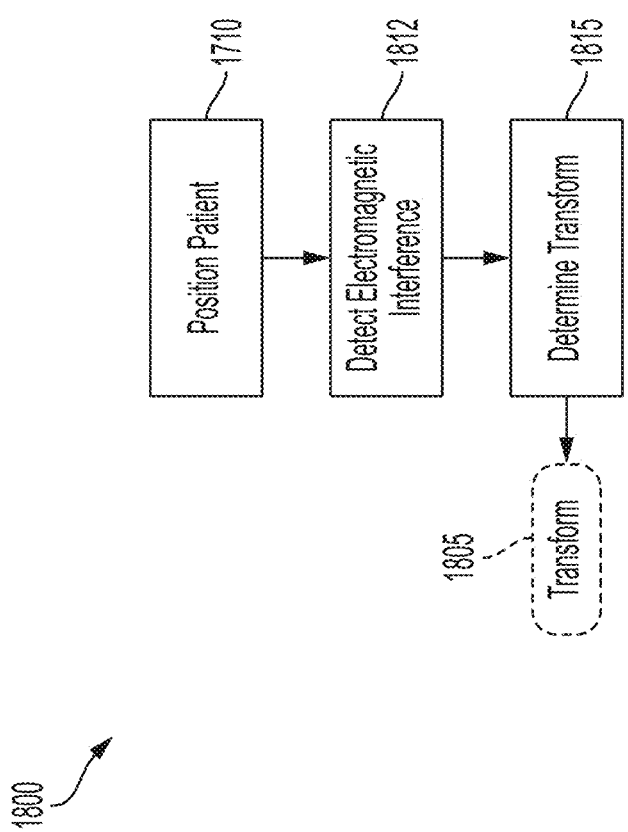
FIG. 18 illustrates a method of determining a transform to facilitate noise suppression, in accordance with some embodiments.

FIG. 18 illustrates a method 1800 of calibrating a noise reduction system prior to imaging, in accordance with some embodiments. In act 1710, a patient to be imaged is positioned within the MRI system so that the anatomy or portion of the anatomy to be imaged is arranged within a field of view of the MRI system (e.g., act 1710 may be similar or the same as described above in connection with the method illustrated in FIG. 17). In act 1812, after the patient has been positioned, electromagnetic interference may be detected, including electromagnetic radiation introduced into the imaging region of the MRI system from the environment via the patient. Unlike act 1722 described in connection with FIG. 17, act 1812 may performed in the absence of MR excitation. In particular, electromagnetic interference may be detected without transmitting RF pulse sequences to the imaging region. As a result, detected electromagnetic radiation can be attributed to noise and not signal since no MR signal is present. The detected electromagnetic interference can be used as calibration measurements to compute a transform that facilitates noise suppression during subsequent operation of the MRI system.

For example, any of the techniques described in U.S. Pat. Application Publication No.: 2016/0069970 may be used to obtain a plurality of calibration measurements from one or more channels of potential electromagnetic interference, wherein at least one channel corresponds electromagnetic radiation from the environment introduced to the MRI system by the patient. That is, any of the sensors described herein may be used to detect electromagnetic radiation from the patient to provide calibration measurements for a transform that characterizes the corresponding noise channel. During performance of act 1812, the receive coil(s) of the MRI system may also be operated to detect electromagnetic radiation which, given that no MR excitation has occurred, provides an indication of the noise environment at the receive coil(s). As described above and in further detail in U.S. Pat. Application Publication No.: 2016/0069970, calibration measurements may be obtained from any number of different sensors (e.g., to provide a relatively comprehensive characterization of the noise environment external to and within the imaging region of the MRI system) so that a transform from each channel (e.g., each different sensor that acquires calibration measurements) to the receive coil(s) of the MRI system may be computed.

In act 1815, the calibration measurements obtained by performing act 1812 are used to compute a transform 1805 to be used by the noise reduction system during operation of the MRI system. For example, the calibration measurements may be used to compute a time domain or frequency domain transform similar or the same as the transforms described in U.S. Pat. Application Publication No.: 2016/0069970. For example, a transform similar to the exemplary transfer functions described in U.S. Pat. Application Publication No.: 2016/0069970 may be computed that include at least one channel that characterizes the electromagnetic interference detected from the patient using any one or combination of sensors described herein. Transform 1805 determined in act 1815 may then be used by the noise reduction system to suppress, mitigate and/or compensate for electromagnetic interference (electromagnetic noise) in MR signals detected during operation of the MRI system to image the patient, for example, as described in further detail below in connection with FIG. 19. In some embodiments, the noise reduction system may estimate an amplitude and phase of the transfer function for each of a plurality of frequency bins of the transfer function using the calibration measurements. In particular, by performing acts 1812 and 1815 prior to operating the MRI system to produce an MR response in the patient, the noise environment external and internal to the MRI system may be characterized to facilitate noise suppression.

Figure 19:
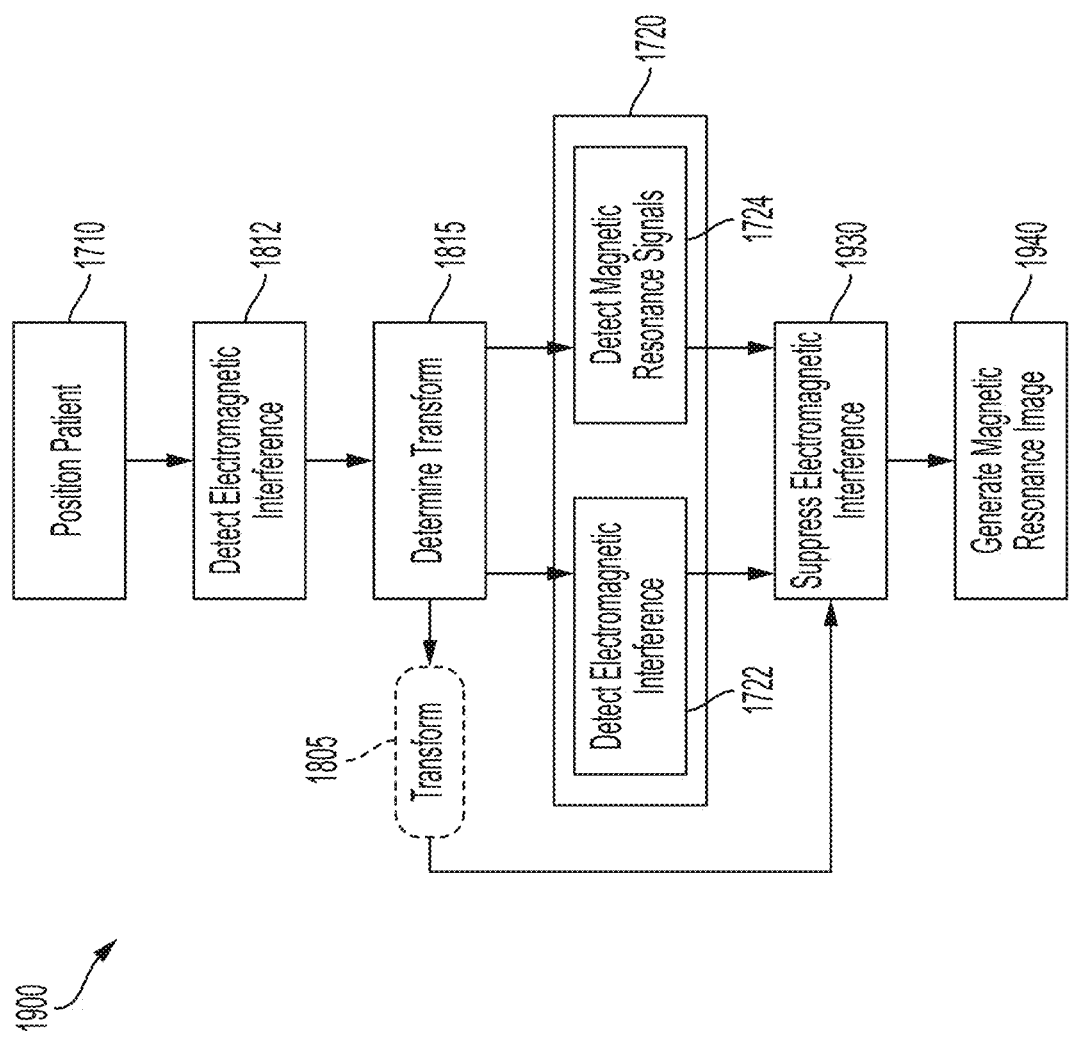
FIG. 19 illustrates a method of suppressing electromagnetic interference, including electromagnetic noise introduced into an MRI system by the patient, in accordance with some embodiments.

FIG. 19 illustrates a method 1900 of performing MRI comprising techniques of detecting electromagnetic interference introduced by the patient into the MRI system and suppressing at least some electromagnetic interference using a transform computed from a plurality of calibration measurements. Initially, a patient is positioned with at least a portion of anatomy to be imaged arranged within an imaging region of the MRI system (e.g., by performing act 1710 described in connection with FIGS. 17 and 18). Once the patient is positioned, electromagnetic interference may be detected in the absence of MR signals to obtain a plurality of calibration measurements (e.g., by performing act 1812 described in connection with method 1800 illustrated in FIG. 18). The plurality of calibration measurements may be used to determine a transform 1805 that, for example, characterizes the noise environment and describes the relationship between how the electromagnetic interference is experienced between each of the sensors and receive coils(s) of the MRI system (e.g., by performing act 1815 described in connection with method 1800 illustrated in FIG. 18 to produce a transform 1805).

Subsequent to obtaining transform 1805, the MRI system may be operated to generate magnetic fields in accordance with a desired pulse sequence to produce an MR response from the patient's anatomy was positioned within the imaging region of the MRI system (e.g., by performing act 1720 described in connection with method 1700 illustrated in FIG. 17). During transmission of a desired pulse sequence, electromagnetic interference and MR signals may be detected by one or more sensors and receive coil(s) of the MRI system (e.g., by performing acts 1722 and 1724 described in connection with method 1700 illustrated in FIG. 17). Detected electromagnetic interference and detected MR signals (which will typically also include electromagnetic interference) may be provided to a noise reduction system to suppress, mitigate or compensate for electromagnetic interference in the detected MR signals.

In particular, in act 1930, transform 1805 determined in act 1815 may be used to transform the electromagnetic interference detected in act 1722 and suppress the transformed electromagnetic interference from the MR signals detected in act 1724. For example, any of the techniques for transforming and suppressing electromagnetic noise described in U.S. Pat. Application Publication No.: 2016/0069970, or any other suitable technique, may be applied in performing act 1930. Subsequent to suppressing electromagnetic interference, one or more magnetic resonance images may be generated. Because the suppression of electromagnetic interference increases the SNR of the detected MR signals, the quality of the resulting magnetic resonance images is improved.

Having thus described several aspects and embodiments of the technology set forth in the disclosure, it is to be appreciated that various alterations, modifications, and improvements will readily occur to those skilled in the art. Such alterations, modifications, and improvements are intended to be within the spirit and scope of the technology described herein. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, and/or methods described herein, if such features, systems, articles, materials, and/or methods are not mutually inconsistent, is included within the scope of the present disclosure.

The above-described embodiments can be implemented in any of numerous ways. One or more aspects and embodiments of the present disclosure involving the performance of processes or methods may utilize program instructions executable by a device (e.g., a computer, a processor, or other device) to perform, or control performance of, the processes or methods. In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above. The computer readable medium or media can be transportable, such that the program or programs stored thereon can be loaded onto one or more different computers or other processors to implement various ones of the aspects described above. In some embodiments, computer readable media may be non-transitory media.

The terms "program" or "software" are used herein in a generic sense to refer to any type of computer code or set of computer-executable instructions that can be employed to program a computer or other processor to implement various aspects as described above. Additionally, it should be appreciated that according to one aspect, one or more computer programs that when executed perform methods of the present disclosure need not reside on a single computer or processor, but may be distributed in a modular fashion among a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

The above-described embodiments of the present disclosure can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as a controller that controls the above-described function. A controller can be implemented in numerous ways, such as with dedicated hardware, or with general purpose hardware (e.g., one or more processor) that is programmed using microcode or software to perform the functions recited above, and may be implemented in a combination of ways when the controller corresponds to multiple components of a system.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smartphone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

Also, as described, some aspects may be embodied as one or more methods (e.g., method 1700). The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

The terms "approximately", "substantially", and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

What is claimed is:

1. A magnetic resonance (MR) imaging system, comprising:
   a magnetics system having a plurality of magnetics components configured to produce magnetic fields for performing magnetic resonance imaging;
   a noise reduction system configured to receive electromagnetic interference electrically coupled from a patient and compensate for the electromagnetic interference during imaging of the patient; and
   a sensor configured to, when the patient is within capacitive coupling range of the sensor, capacitively couple the electromagnetic interference from the patient to the sensor and to provide the electromagnetic interference to the noise reduction system.

2. The MR imaging system of claim 1, wherein:
   the plurality of magnetics components include at least one radio frequency (RF) coil configured to, when operated, receive magnetic resonance signals emitted from a field of view of the MR imaging system; and
   the noise reduction system is configured to reduce an impact of the electromagnetic interference on the magnetic resonance signals.

3. The MR imaging system of claim 1, wherein the noise reduction system is configured to obtain samples of the electromagnetic interference and subtract a version of the samples from MR signals received via the magnetics system.

4. The MR imaging system of claim 3, wherein the noise reduction system is configured to apply a transfer function to the samples and subtract transformed versions of the samples from the MR signals.

5. The MR imaging system of claim 4, wherein the noise reduction system is configured to obtain calibration noise measurements of the electromagnetic interference and determine the transfer function using the calibration noise measurements.

6. The MR imaging system of claim 5, wherein the noise reduction system is configured to estimate an amplitude and phase of the transfer function for each of a plurality of frequency bins of the transfer function using the calibration noise measurements.

7. An electric field detector (EFD) for a magnetic resonance (MR) imaging system, the EFD comprising:
   at least one electrical conductor configured to, when positioned within capactive coupling range of a patient, capacitively couple electromagnetic interference from the patient to the at least one electrical conductor,
   wherein the at least one electrical conductor is further configured to provide the electromagnetic interference to a noise reduction system of the MR imaging system.

8. The EFD of claim 7, wherein the at least one electrical conductor is configured for placement proximate an imaging region that is within a magnetic component of the MR imaging system to capacitively couple to the patient when at least a portion of the patient's anatomy is positioned in the imaging region.

9. The EFD of claim 8, wherein the EFD further comprises one or more flexible printed circuit boards (PCBs) having the at least one electrical conductor thereon.

10. The EFD of claim 9, wherein the one or more flexible PCBs are configured for coupling to the noise reduction system of the MR imaging system via at least one electrical connector.

11. The EFD of claim 8, wherein:
   the at least one electrical conductor is configured for attaching to a surface of the magnetic component of the MR imaging system proximate the imaging region.

12. The EFD of claim 11, further comprising:
   electromagnetic shielding configured to be positioned between the magnetic component and the at least one electrical conductor,
   wherein the magnetic component comprises at least one radio frequency coil, and the electromagnetic shielding is configured to be positioned between the at least one radio frequency coil and the at least one electrical conductor.

13. The EFD of claim 11, wherein the magnetic component is a radio frequency (RF) component comprising a housing formed to accommodate a portion of the patient's anatomy in the imaging region, and the at least one electrical conductor is configured for attaching to at least one interior surface of the housing proximate the imaging region.

14. A method of compensating for electromagnetic interference introduced by a patient into an imaging region of a magnetic resonance (MR) imaging system, the method comprising:
   using at least one electrical conductor of an electric field detector (EFD), when the at least one electrical conductor is positioned within capacitive coupling range of the patient, to capacitively couple the electromagnetic interference from the patient to the at least one electrical conductor; and
   providing the electromagnetic interference from the sensor to a noise reduction system of the MR imaging system.

15. The method of claim 14, wherein the at least one electrical conductor is placed proximate at least a portion of the imaging region that is within a magnetic component of the MR imaging system and capacitively couples to at least a portion of the patient's anatomy while the portion of the patient's anatomy is positioned in the portion of the imaging region.

16. The method of claim 15, wherein:
   the at least one electrical conductor is attached to a magnetic component of the MR imaging system; and
   the method further comprises blocking at least some electrical coupling between the magnetic component and the at least one electrical conductor using electromagnetic shielding.

17. The method of claim 12, further comprising:
   obtaining samples of the electromagnetic interference from the EFD;
   applying a transfer function to the samples; and
   subtracting transformed versions of the samples from MR signals received via a magnetics system of the MR imaging system.

18. The method of claim 17, further comprising obtaining calibration noise measurements of the electromagnetic interference and determining the transfer function using the calibration noise measurements.

19. The method of claim 18, further comprising estimating an amplitude and phase of the transfer function for each of a plurality of frequency bins of the transfer function using the calibration noise measurements.

20. The MR imaging system of claim 1, further comprising:
   a magnetic component having a housing with an imaging region of the MR imaging system within the housing, wherein the sensor is positioned proximate the imaging region within the housing of the magnetic component.

* * * * *